United States Patent
Otake et al.

(10) Patent No.: US 10,464,884 B2
(45) Date of Patent: Nov. 5, 2019

(54) PRODRUG OF AMINO ACID DERIVATIVE

(71) Applicant: TAISHO PHARMACEUTICAL CO., LTD, Tokyo (JP)

(72) Inventors: Norikazu Otake, Tokyo (JP); Takashi Hashihayata, Tokyo (JP); Yohei Matsuda, Tokyo (JP); Seiji Masuda, Tokyo (JP); Yuko Yamauchi, Tokyo (JP)

(73) Assignee: TAISHO PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 15/765,903

(22) PCT Filed: Apr. 18, 2017

(86) PCT No.: PCT/JP2017/016125
§ 371 (c)(1),
(2) Date: Apr. 4, 2018

(87) PCT Pub. No.: WO2017/183734
PCT Pub. Date: Oct. 26, 2017

(65) Prior Publication Data
US 2019/0047943 A1     Feb. 14, 2019

(30) Foreign Application Priority Data
Apr. 18, 2016 (JP) .................. 2016-083147

(51) Int. Cl.
C07C 229/50   (2006.01)
C07D 213/61   (2006.01)
C07D 213/64   (2006.01)

(52) U.S. Cl.
CPC .......... *C07C 229/50* (2013.01); *C07D 213/61* (2013.01); *C07D 213/64* (2013.01); *C07C 2601/08* (2017.05); *C07C 2601/14* (2017.05); *C07C 2601/16* (2017.05); *C07C 2602/18* (2017.05); *C07C 2603/56* (2017.05); *C07C 2603/74* (2017.05)

(58) Field of Classification Search
CPC ...................... C07C 229/50; C07C 255/47
See application file for complete search history.

(56) References Cited

U.S. PATENT DOCUMENTS

| | | | |
|---|---|---|---|
| 9,056,844 B2* | 6/2015 | Dressman | A61K 31/138 |
| 9,428,483 B2* | 8/2016 | Hashihayata | A61K 31/265 |
| 2007/0021394 A1 | 1/2007 | Yasuhara | |
| 2015/0119345 A1 | 4/2015 | Gedulin | |
| 2015/0141669 A1 | 5/2015 | Hashihayata | |

FOREIGN PATENT DOCUMENTS

| | | |
|---|---|---|
| WO | WO 03/045898 | 6/2003 |
| WO | WO 03/061698 | 7/2003 |
| WO | WO 2005/000791 | 1/2005 |
| WO | WO 2012/068041 | 5/2012 |
| WO | WO 2012/068067 | 5/2012 |
| WO | WO 2013/062680 | 5/2013 |
| WO | WO 2013/180271 | 12/2013 |

OTHER PUBLICATIONS

International Search Report dated Jun. 28, 2017, in corresponding PCT International Application No. PCT/JP2017/016125 (two pages).
Schoepp et al.; "Metabotropic glutamate receptors in brain function and pathology", Trends Pharmacol. Sci., vol. 14, pp. 13-20, (1993).
Kilbride et al.; "Presynaptic inhibitory action of the group II metabotropic glutamate receptor agonists, LY354740 and DCG-IV", European Journal of Pharmacology, vol. 356, pp. 149-157, (1998).
Chaki et al.; "MGS0039: a potent and selective group II metabotropic glutamate receptor antagonist with antidepressant-like activity", Neuropharmacology, vol. 46, pp. 457-467, (2004).

(Continued)

*Primary Examiner* — Golam M Shameem
(74) *Attorney, Agent, or Firm* — Finnegan, Henderson, Farabow, Garrett & Dunner, LLP

(57) ABSTRACT

Provided is an amino acid derivative prodrug represented by general formula (I-A) that is a prodrug form of an amino acid derivative which is a group 2 metabotropic glutamate receptor antagonist, or a pharmaceutically acceptable salt thereof.

More specifically, provided is an amino acid derivative prodrug represented by general formula (I-A) that is a preventive or therapeutic drug for mood disorders (including depression and bipolar disorder), anxiety disorder, cognitive disorders, developmental disorders, Alzheimer's disease, Parkinson's disease, movement disorders associated with muscular rigidity, sleep disorders, Huntington's chorea, eating disorders, drug dependence, epilepsy, brain infarction, cerebral ischemia, cerebral insufficiency, cerebral edema, spinal cord disorders, head trauma, inflammation and immune-related diseases, and so on.

[Formula 1]

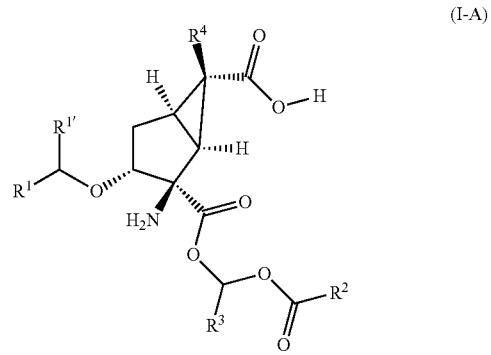

(I-A)

18 Claims, No Drawings

(56) References Cited

OTHER PUBLICATIONS

Yasuhara et al.; "Synthesis, in vitro pharmacology, and structure-activity relationships of 2-aminobicyclo[3.1.0]hexane-2,6-dicarboxylic acid derivatives as mGluR2 antagonists", Bioorganic & Medicinal Chemistry, vol. 14, pp. 3405-3420, (2006).

Yasuhara et al.; "Prodrugs of 3-(3,4-dichlorobenzyloxy)-2-amino-6-fluorobicyclo[3.1.0]hexane-2,6-dicarboxylic acid (MGS0039): a potent and orally active group II mGluR antagonist with antidepresant-like potential", Bioorganic & Medicinal Chemistry, vol. 14, pp. 4193-4207, (2006).

Nakazato et al.; "Synthesis, in Vitro Pharmacology, Structure-Activity Relationships, and Pharmacokinetics of 3-Alkoxy-2-amino-6-fluorobicyclo[3.1.0]hexane-2,6-dicarboxylic Acid Derivatives as Potent and Selective Group II Metabotropic Glutamate Receptor Antagonists", J. Med. Chem., vol. 47, pp. 4570-4587, (2004).

Kew et al.; "Activity-dependent presynaptic autoinhibition by group II metabotropic glutamate receptors at the perforant path inputs to the dentate gyrus and CA1", Neuropharmacology vol. 40, pp. 20-27, (2001).

\* cited by examiner

US 10,464,884 B2

PRODRUG OF AMINO ACID DERIVATIVE

CROSS-REFERENCE TO RELATED PATENT APPLICATIONS

This application is a National Stage Entry of International Application No. PCT/JP2017/016125, filed Apr. 18, 2017, which claims priority from Japanese Patent Application No. 2016-083147, filed Apr. 18, 2016. The entire contents of the above-referenced applications are expressly incorporated herein by reference.

TECHNICAL FIELD

The present invention relates to prodrugs of (1R,2R,3R, 5R,6R)-2-amino-6-fluoro-3-alkoxybicyclo[3.1.0]hexane-2, 6-dicarboxylic acid derivatives and (1S,2R,3R,5R,6S)-2-amino-3-alkoxybicyclo[3.1.0]hexane-2,6-dicarboxylic acid derivatives useful as drugs. More specifically, the present invention relates to prodrugs of (1R,2R,3R,5R,6R)-2-amino-6-fluoro-3-alkoxybicyclo[3.1.0]hexane-2,6-dicarboxylic acid derivatives and (1S,2R,3R,5R,6S)-2-amino-3-alkoxybicyclo[3.1.0]hexane-2,6-dicarboxylic acid derivatives, which are compounds that act as antagonists of mGlu2 and mGlu3 receptors belonging to subgroup 2 of metabotropic glutamate (mGlu) receptors and are effective for treatment or prevention of, for example, mood disorders (including depression and bipolar disorder), anxiety disorder, cognitive disorders, developmental disorders, Alzheimer's disease, Parkinson's disease, movement disorders associated with muscular rigidity, sleep disorders, Huntington's chorea, eating disorders, drug dependence, epilepsy, brain infarction, cerebral ischemia, cerebral insufficiency, cerebral edema, spinal cord disorders, head trauma, inflammation and immune-related diseases. The present invention also relates to the finding that prodrugs of compounds (active forms) acting as antagonists of mGlu2 and mGlu3 receptors enhance the oral absorbability and increase the in vivo exposure of the active forms.

BACKGROUND ART

Metabotropic glutamate receptors are classified into 3 groups according to the sequence homology, signal transduction mechanisms and pharmacological properties. Among them, group 2 metabotropic glutamate receptors (mGlu2 and mGlu3 receptors) are G protein-coupled receptors that bind to adenyl cyclase and suppress the phosphocholine-stimulated accumulation of cyclic adenosine monophosphate (cAMP) (Non Patent Literature 1). Also, the group 2 metabotropic glutamate receptors exist mainly in the presynapses of the glutamatergic nervous system and function as autoreceptors, thus suppressing excessive release of glutamic acid (Non Patent Literatures 2 and 3). It is considered that compounds antagonizing group 2 metabotropic glutamate receptors may be effective for treatment or prevention of acute and chronic neuropsychiatric diseases and neurological diseases. (1R,2R,3R,5R,6R)-2-Amino-6-fluoro-3-alkoxybicyclo[3.1.0]hexane-2,6-dicarboxylic acid derivatives and (1S,2R,3R,5R,6S)-2-amino-3-alkoxybicyclo[3.1.0]hexane-2,6-dicarboxylic acid derivatives are compounds having a strong antagonistic effect on group 2 metabotropic glutamate receptors. For example, MGS0039 is disclosed as such a compound. Its antagonistic activity is 20 nM (mGlu2 receptor) and 24 nM (mGlu3 receptor), and it has been reported that 1 mg/kg of the compound is sufficient to suppress immobility time, as with existing antidepressants, in the forced swimming test of rats as depression animal models. It has been further reported that the compound also shortens immobility time, as with existing antidepressants, in the tail suspension test of mice (Non Patent Literature 4). It has also been reported that (1R,2R, 3R,5R,6R)-2-amino-6-fluoro-3-[(4-fluorophenyl)methoxy] bicyclo[3.1.0]hexane-2,6-dicarboxylic acid, (1R,2R,3R,5R, 6R)-2-amino-3-[(3,4-difluorophenyl)methoxy]-6-fluoro-bicyclo[3.1.0]hexane-2,6-dicarboxylic acid and (1R,2R,3R, 5R,6R)-2-amino-6-fluoro-3-propoxybicyclo[3.1.0]hexane-2,6-dicarboxylic acid, which are (1R,2R,3R,5R,6R)-2-amino-6-fluoro-3-alkoxybicyclo[3.1.0]hexane-2,6-dicarboxylic acid derivatives, have antagonistic activity of 500 nM or less against mGlu2 receptors (Patent Literature 1 and Non Patent Literature 5).

However, the oral absorbability of the (1R,2R,3R,5R,6R)-2-amino-6-fluoro-3-alkoxybicyclo[3.1.0]hexane-2,6-dicarboxylic acid derivatives and (1S,2R,3R,5R,6S)-2-amino-3-alkoxybicyclo[3.1.0]hexane-2,6-dicarboxylic acid derivatives is poor in monkeys. This suggests the possibility that the oral absorbability may also be poor in humans.

There are mainly two approaches to improvement of the membrane permeability (e.g., oral absorbability) of compounds. One is a method of changing their chemical structures themselves and the other is a method of devising a means of formulation without changing their chemical structures. The former method encompasses attaching a small modifying group such as an alkyl group or an acyl group to a reactive substituent such as a carboxy group or amino group of compounds to form them into prodrugs.

Compounds preferred as the aforementioned prodrugs are compounds that exist stably in prodrug forms before absorption, exhibit improved absorption after being formed into prodrugs and are converted to active forms chemically or enzymatically and rapidly in the small intestine, the liver and/or plasma during and/or after absorption.

However, it is difficult to develop ideal prodrugs that satisfy all of the aforementioned conditions. For example, prodrugs having an ester bond can be more likely to be hydrolyzed, which may have a great influence on chemical stability before absorption. As for prodrugs having an amide bond, a great change of the physical properties of compounds may have a great influence on membrane permeability such as oral absorbability. Further, an amide bond is less likely to be hydrolyzed, which may have a great influence on biotransformation of compounds to active forms and plasma concentrations. Furthermore, it is difficult to predict the pharmacokinetic profiles of prodrugs because enzymes that control biotransformation of prodrugs to active forms are substrate-specific and particularly, for example, the steric hindrance of a substituent inserted for formation of prodrugs prevents reaction of the enzymes. For these reasons, it is by no means easy to enhance the plasma concentrations of active forms by estimating possible improvements in the membrane permeability (e.g., oral absorbability) of prodrugs and their transformation to the active forms. There are previous reports on enhancement in the plasma concentrations of active forms by prodrugs having ester bond(s) at 6-carboxylic acid or both of 2-carboxylic acid and 6-carboxylic acid of a 2-amino-bicyclo [3.1.0]hexane-2,6-dicarboxylic acid derivative which is a compound acting as an antagonist of mGlu2 and mGlu3 receptors (Patent Literatures 2, 3, 4 and 5 and Non Patent Literature 6). However, these literatures neither describe nor suggest enhancement in the plasma concentrations of active forms by prodrug compounds having an ester bond only at 2-carboxylic acid. Furthermore, the literatures neither describe nor suggest enhancement in the plasma concentrations of active forms by the prodrugs of the active forms of the present invention.

CITATION LIST

Patent Literature

Patent Literature 1: WO03/061698
Patent Literature 2: WO05/000791
Patent Literature 3: WO2012/068041
Patent Literature 4: WO2012/068067
Patent Literature 5: WO2013/062680

Non Patent Literature

Non Patent Literature 1: Trends Pharmacol. Sci., 14, 13-20, 1993
Non Patent Literature 2: Neuropharmacol., 40, 20-27, 2001
Non Patent Literature 3: Eur. J. Pharmacol., 356, 149-157, 1998
Non Patent Literature 4: Neuropharmacol., 2004, 46 (4), 457-67
Non Patent Literature 5: J. Med. Chem., 2004, 47, 4570-4587
Non Patent Literature 6: Bioorg. Med. Chem., 2006, 14, 4193-4207

SUMMARY OF INVENTION

Technical Problem

An objective of the present invention is to provide drugs that have the effect of treating or preventing, for example, mood disorders (including depression and bipolar disorder), anxiety disorder, cognitive disorders, developmental disorders, Alzheimer's disease, Parkinson's disease, movement disorders associated with muscular rigidity, sleep disorders, Huntington's chorea, eating disorders, drug dependence, epilepsy, brain infarction, cerebral ischemia, cerebral insufficiency, cerebral edema, spinal cord disorders, head trauma, inflammation and immune-related diseases and are highly orally active drugs antagonizing group 2 metabotropic glutamate receptors.

Solution to Problem

The inventors of the present invention conducted extensive and intensive studies on (1R,2R,3R,5R,6R)-2-amino-6-fluoro-3-alkoxybicyclo[3.1.0]hexane-2,6-dicarboxylic acid ester derivatives and (1S,2R,3R,5R,6S)-2-amino-3-alkoxybicyclo[3.1.0]hexane-2,6-dicarboxylic acid ester derivatives and, as a result, the inventors have found that prodrugs of (1R,2R,3R,5R,6R)-2-amino-6-fluoro-3-alkoxybicyclo[3.1.0]hexane-2,6-dicarboxylic acid derivatives and (1S,2R,3R,5R,6S)-2-amino-3-alkoxybicyclo[3.1.0]hexane-2,6-dicarboxylic acid derivatives having antagonistic activity against group 2 metabotropic glutamate receptors are stable in a stability test in solutions simulating the stomach and the small intestine and are converted to active forms in liver S9 fractions. Through animal experiments using active forms and prodrugs as test drugs, the inventors have also found that this kind of prodrug enhances the in vivo exposure of the active forms. These findings have led to the completion of the present invention.

The present invention is described below in detail. Embodiments of the present invention (hereinafter, the compounds of the embodiments are referred to as "Inventive Compounds") are described below.

(1) A compound represented by formula (I-A):

[Formula 1]

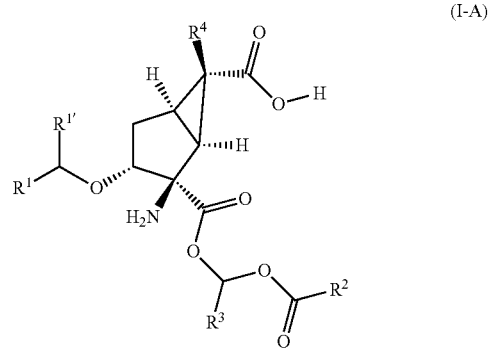

wherein
$R^1$ represents a $C_{1-6}$ alkyl group, a heteroaryl group (the heteroaryl group is optionally substituted by one halogen atom) or the following formula (IIIA):

[Formula 2]

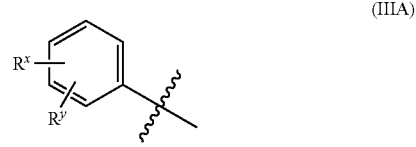

where $R^x$ represents a hydrogen atom, a halogen atom, a $C_{1-6}$ alkyl group, or a $C_{1-6}$ alkoxy group (the $C_{1-6}$ alkyl group and the $C_{1-6}$ alkoxy group are each optionally substituted by one to three halogen atoms), and
$R^y$ represents a hydrogen atom, a fluorine atom, a $C_{1-6}$ alkyl group, or a $C_{1-6}$ alkoxy group (the $C_{1-6}$ alkyl group and the $C_{1-6}$ alkoxy group are each optionally substituted by one to three halogen atoms),
$R^{1'}$ represents a hydrogen atom or a $C_{1-6}$ alkyl group,
or $R^1$ and $R^{1'}$ optionally form a $C_{3-8}$ cycloalkane together with the carbon atom adjacent thereto,
$R^2$ represents a $C_{3-6}$ alkyl group (the $C_{3-6}$ alkyl group is optionally substituted by one amino group), a $C_{3-8}$ cycloalkyl group (the $C_{3-8}$ cycloalkyl group is optionally substituted by one to three $C_{1-6}$ alkyl groups), a $C_{3-8}$ cycloalkoxy group (the $C_{3-8}$ cycloalkoxy group is optionally substituted by one to three $C_{1-6}$ alkyl groups and the $C_{3-8}$ cycloalkoxy group optionally has a $C_{1-5}$ alkylene group crosslinking two different carbon atoms in the ring), an adamantyl group (the adamantyl group is optionally substituted by one to three $C_{1-6}$ alkyl groups) or a phenyl group,
$R^3$ represents a hydrogen atom or a $C_{1-6}$ alkyl group, and
$R^4$ represents a hydrogen atom or a fluorine atom,
or a pharmaceutically acceptable salt thereof.

(2) The compound according to (1), wherein $R^4$ is a fluorine atom, or a pharmaceutically acceptable salt thereof.

(3) The compound according to (2), wherein $R^2$ is a $C_{3-6}$ alkyl group, a $C_{3-8}$ cycloalkyl group (the $C_{3-8}$ cycloalkyl group is optionally substituted by one to three $C_{1-6}$ alkyl groups), a $C_{3-8}$ cycloalkoxy group (the $C_{3-8}$ cycloalkoxy group is optionally substituted by one to three $C_{1-6}$ alkyl groups and the $C_{3-8}$ cycloalkoxy group optionally has a $C_{1-5}$ alkylene group crosslinking two different carbon atoms in the ring), an adamantyl group (the adamantyl group is optionally substituted by one to three $C_{1-6}$ alkyl groups) or a phenyl group, or a pharmaceutically acceptable salt thereof.

(4) The compound according to (2) or (3), wherein $R^4$ is an ethyl group, a 4-fluorophenyl group, a 3,4-difluorophenyl group, a 4-fluoro-3-methoxyphenyl group, a 4-(trifluoromethyl)phenyl group, a 3-fluorophenyl group, a 4-methylphenyl group, a 6-chloropyridin-2-yl group, a 6-chloropyridin-3-yl group, a 5-chloropyridin-2-yl group or a 2-methylpropyl group, $R^{1'}$ represents a hydrogen atom or a methyl group, or $R^1$ and $R^{1'}$ optionally form a cyclopentane together with the carbon atom adjacent thereto, $R^2$ represents any structure of the following formula group (IIIB):

[Formula 3]

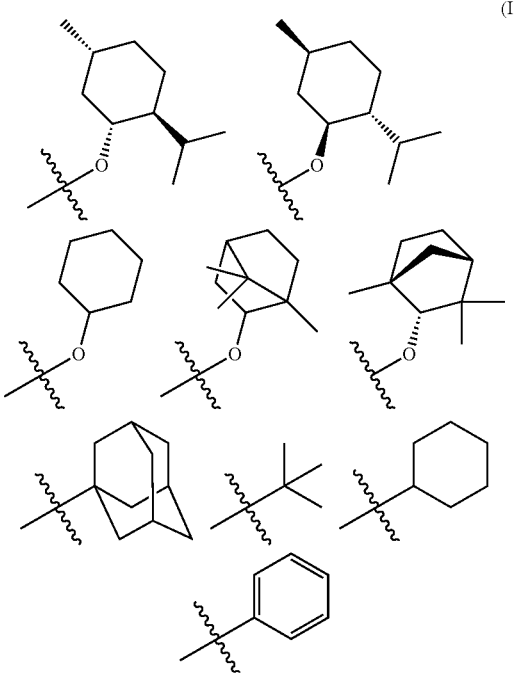

(IIIB)

and $R^3$ is a hydrogen atom or a $C_{1-6}$ alkyl group, or a pharmaceutically acceptable salt thereof.

(5) The compound according to (1), wherein $R^4$ is a hydrogen atom, or a pharmaceutically acceptable salt thereof.

(6) The compound according to (5), wherein $R^1$ is an ethyl group, a 4-fluorophenyl group, a 3,4-difluorophenyl group, a 4-fluoro-3-methoxyphenyl group, a 4-(trifluoromethyl)phenyl group, a 3-fluorophenyl group, a 4-methylphenyl group, a 6-chloropyridin-2-yl group, a 6-chloropyridin-3-yl group, a 5-chloropyridin-2-yl group or a 2-methylpropyl group, $R^{1'}$ represents a hydrogen atom or a methyl group, or $R^1$ and $R^{1'}$ optionally form a cyclopenane together with the carbon atom adjacent thereto, $R^2$ represents any structure of the following formula group (IIIB):

[Formula 4]

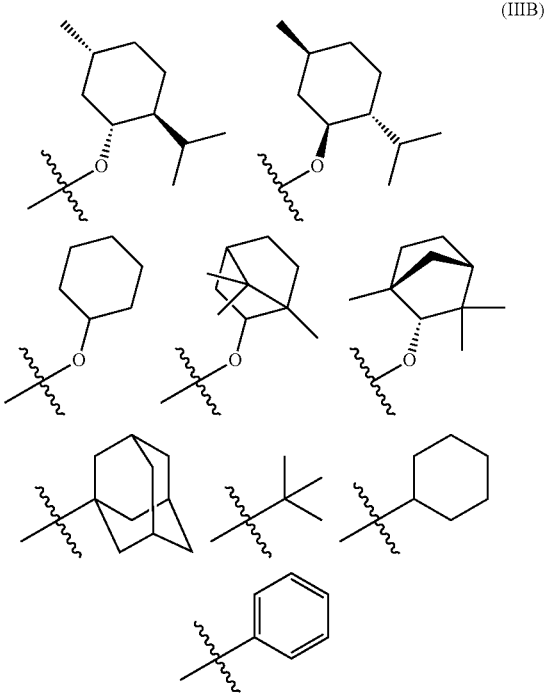

(IIIB)

and $R^3$ is a hydrogen atom or a $C_{1-6}$ alkyl group, or a pharmaceutically acceptable salt thereof.

(7) The compound according to (5) or (6), wherein $R^1$ is a 4-fluorophenyl group or a 3,4-difluorophenyl group, or a pharmaceutically acceptable salt thereof.

(8) The compound according to any one of (5) to (7), wherein $R^1$ is a 4-fluorophenyl group, $R^{1'}$ is a hydrogen atom, and $R^2$ represents any structure of the following formula group (IIIb):

[Formula 5]

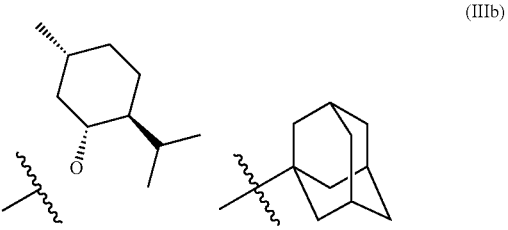

(IIIb)

or a pharmaceutically acceptable salt thereof.

(9) The compound according to any one of (5) to (8), wherein $R^3$ is a methyl group, or a pharmaceutically acceptable salt thereof.

(10) A compound represented by formula (I):

[Formula 6]

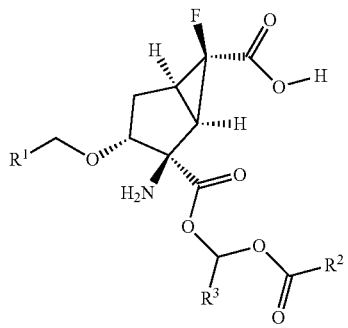

(I)

wherein
R¹ represents an ethyl group, a 4-fluorophenyl group or a 3,4-difluorophenyl group,
R² represents any structure of the following formula group (IIIa):

[Formula 7]

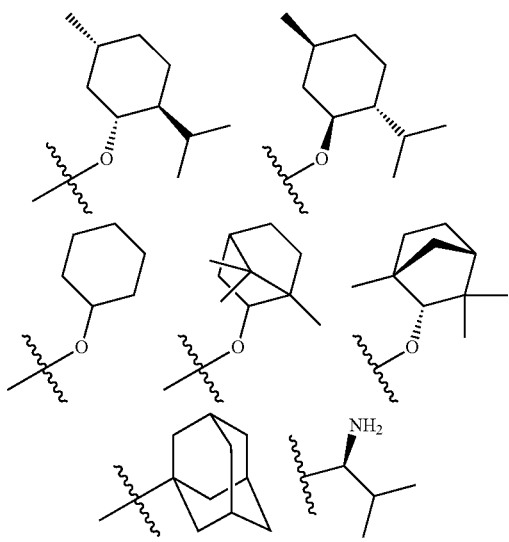

(IIIa)

and
R³ represents a hydrogen atom or a $C_{1-6}$ alkyl group,
or a pharmaceutically acceptable salt thereof.
(11) The compound according to (10), wherein R² represents any structure of the following formula group (IIIa'):

[Formula 8]

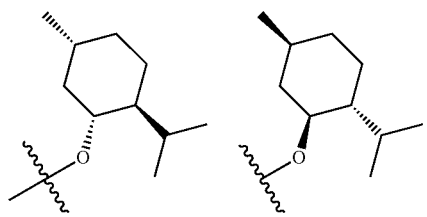

(IIIa')

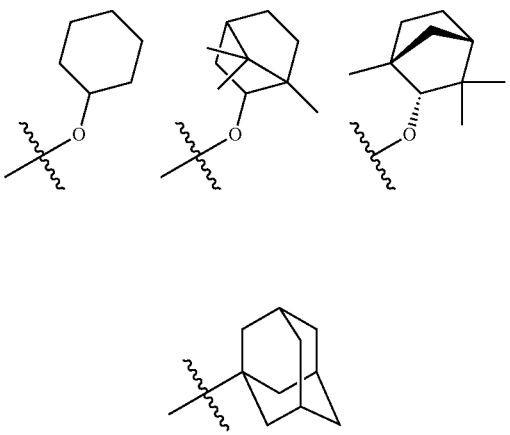

or a pharmaceutically acceptable salt thereof.
(12) The compound according to (10), wherein R² represents any structure of the following formula group (IIIb):

[Formula 9]

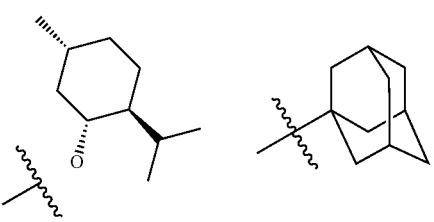

(IIIb)

or a pharmaceutically acceptable salt thereof.
(13) The compound according to any one of (10) to (12), wherein R³ is a methyl group, or a pharmaceutically acceptable salt thereof.
(14) The compound according to (1), wherein the compound is any of the following compounds:

(1R,2R,3R,5R,6R)-2-amino-6-fluoro-3-[(4-fluorophenyl)methoxy]-2-({(1S)-1-[(tricyclo[3.3.1.1³,⁷]decane-1-carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({[(tricyclo[3.3.1.1³,⁷]decane-1-carbonyl)oxy]methoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({(1S)-1-[(tricyclo[3.3.1.1³,⁷]decane-1-carbonyl)oxy]ethoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({[(tricyclo[3.3.1.1³,⁷]decane-1-carbonyl)oxy]methoxy}carbonyl)bicyclo[3.1.0]hexane-6-carboxylic acid, (1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-2-({1-[({[(1S,2R,5S)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-3-[(4-fluorophenyl)methoxy]-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-3-propoxy-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-2-({(1S)-1-[(tricyclo[3.3.1.1$^{3,7}$]decane-1-carbonyl)oxy]ethoxy}carbonyl)-3-{[4-(trifluoromethyl)phenyl]methoxy}bicyclo[3.1.0]hexane-6-carboxylic acid, (1R,2R,3R,5R,6R)-2-amino-6-fluoro-3-[(3-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(1R)-1-(4-fluoro-3-methoxyphenyl)ethoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(5-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-3-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-methylphenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-(3-methylbutoxy)-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-(cyclopentyloxy)-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(3-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid, (1R,2R,3R,5R,6R)-2-amino-2-({[(2,2-dimethylpropanoyl)oxy]methoxy}carbonyl)-6-fluoro-3-[(4-fluorophenyl)methoxy]bicyclo[3.1.0]hexane-6-carboxylic acid, (1R,2R,3R,5R,6R)-2-amino-2-{[(benzoyloxy)methoxy]carbonyl}-6-fluoro-3-[(4-fluorophenyl)methoxy]bicyclo[3.1.0]hexane-6-carboxylic acid, (1R,2R,3R,5R,6R)-2-amino-2-({[(cyclohexanecarbonyl)oxy]methoxy}carbonyl)-6-fluoro-3-[(4-fluorophenyl)methoxy]bicyclo[3.1.0]hexane-6-carboxylic acid, and (1S,2R,3R,5R,6S)-2-amino-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, or a pharmaceutically acceptable salt thereof.

(15) The compound according to (1), wherein the compound is any of the following compounds:

(1R,2R,3R,5R,6R)-2-amino-6-fluoro-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-2-({(1S)-1-[(tricyclo[3.3.1.1$^{3,7}$]decane-1-carbonyl)oxy]ethoxy}carbonyl)-3-{[4-(trifluoromethyl)phenyl]methoxy}bicyclo[3.1.0]hexane-6-carboxylic acid, (1R,2R,3R,5R,6R)-2-amino-6-fluoro-3-[(3-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(1R)-1-(4-fluoro-3-methoxyphenyl)ethoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(5-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-3-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-methylphenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-(3-methylbutoxy)-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-(cyclopentyloxy)-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, and (1S,2R,3R,5R,6S)-2-amino-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, or a pharmaceutically acceptable salt thereof.

(16) The compound according to any one of (1) to (4) or (10) to (13), wherein the compound is the following compound:

(1R,2R,3R,5R,6R)-2-amino-6-fluoro-3-[(4-fluorophenyl)methoxy]-2-({(1S)-1-[(tricyclo[3.3.1.1³,⁷]decane-1-carbonyl)oxy]ethoxy}carbonyl)bicyclo[3.1.0]hexane-6-carboxylic acid,
or a pharmaceutically acceptable salt thereof.

[Formula 10]

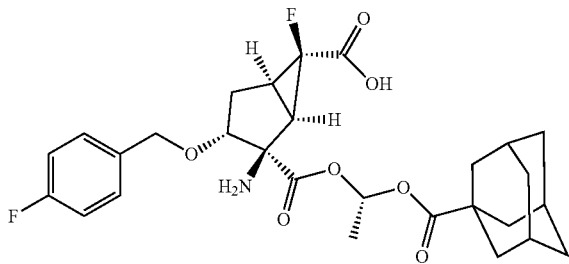

(17) The compound according to any one of (1) to (4) or (10) to (13), wherein the compound is the following compound:
(1R,2R,3R,5R,6R)-2-amino-3-[(3,4-difluorophenyl)methoxy]-6-fluoro-2-({(1S)-1-[(tricyclo[3.3.1.1³,⁷]decane-1-carbonyl)oxy]ethoxy}carbonyl)bicyclo[3.1.0]hexane-6-carboxylic acid,
or a pharmaceutically acceptable salt thereof.

[Formula 11]

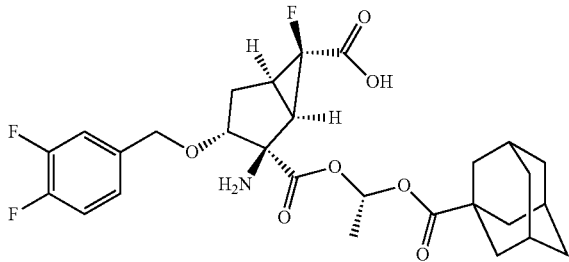

(18) The compound according to any one of (1) to (4) or (10) to (13), wherein the compound is the following compound:
(1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid,
or a pharmaceutically acceptable salt thereof.

[Formula 12]

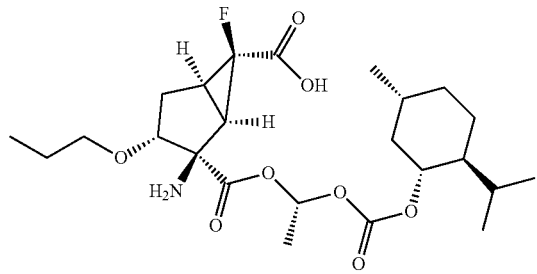

(19) A drug comprising the compound according to any one of (1) to (18) or a pharmaceutically acceptable salt thereof.
(20) An agent for prevention or treatment of a condition selected from the group consisting of mood disorders (including depression and bipolar disorder), anxiety disorder, cognitive disorders, developmental disorders, Alzheimer's disease, Parkinson's disease, sleep disorders, Huntington's chorea, eating disorders, drug dependence, epilepsy, brain infarction, cerebral ischemia, cerebral edema, head trauma, inflammation and immune-related diseases, comprising the compound according to any one of (1) to (18) or a pharmaceutically acceptable salt thereof.

Advantageous Effects of Invention

An amino acid derivative prodrug of the present invention is enhanced in membrane permeability such as oral absorbability and is converted to active form (II)-A, (II)-1, (II)-2 or (II)-3 rapidly after absorption. The active form exhibits affinity for group 2 metabotropic glutamate receptors and has an antagonistic effect.

[Formula 13]

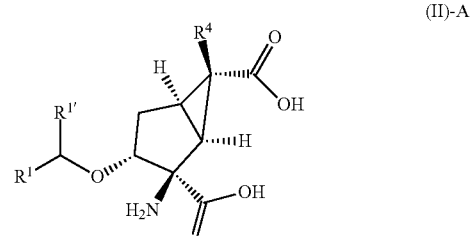

(II)-A

Wherein $R^1$, $R^{1'}$ and $R^4$ are as defined above.

[Formula 14]

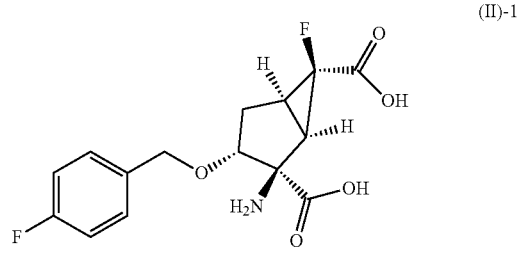

(II)-1

[Formula 15]

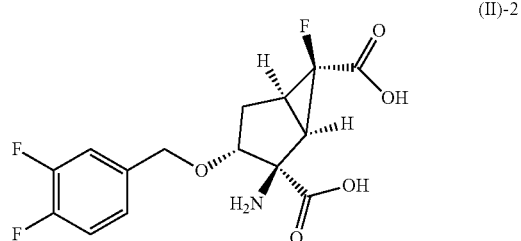

(II)-2

[Formula 16]

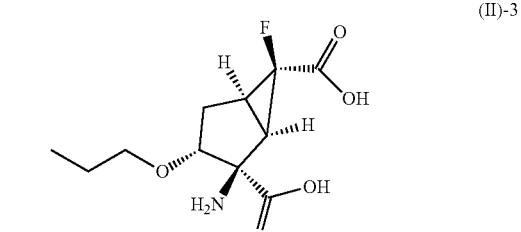

(II)-3

DESCRIPTION OF EMBODIMENTS

Embodiments for carrying out the present invention are described specifically below.

The meanings of the terms and phrases used herein are as follows:

The "$C_{1-6}$ alkyl group" means a linear or branched alkyl group having one to six carbon atoms, and examples can include groups such as methyl group, ethyl group, n-propyl group, isopropyl group, n-butyl group, isobutyl group, sec-butyl group, tert-butyl group, n-pentyl group, isopentyl group, neopentyl group, tert-pentyl group, 1-ethylpropyl group, n-hexyl group, isohexyl group, and neohexyl group.

The "$C_{3-6}$ alkyl group" means a linear or branched alkyl group having three to six carbon atoms, and examples can include groups such as n-propyl group, isopropyl group, n-butyl group, isobutyl group, sec-butyl group, tert-butyl group, n-pentyl group, isopentyl group, neopentyl group, tert-pentyl group, 1-ethylpropyl group, n-hexyl group, isohexyl group and neohexyl group.

The "heteroaryl group" means a monocyclic aromatic heterocyclic group, and examples can include groups such as a pyridyl group, a pyridazinyl group, a pyrimidinyl group, a pyrazinyl group, a pyridonyl group, a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group, a 1,3,4-thiadiazolyl group, a 1,2,3-triazolyl group, a 1,2,4-triazolyl group and a tetrazolyl group.

The "halogen atom" refers to a fluorine atom, a chlorine atom, a bromine atom or an iodine atom.

The "$C_{1-6}$ alkoxy group" refers to a linear or branched alkoxy group having one to six carbon atoms, and examples can include groups such as a methoxy group, an ethoxy group, a propoxy group, a butoxy group, a pentyloxy group, a hexyloxy group, an isopropoxy group, an isobutoxy group, a tert-butoxy group, a sec-butoxy group, an isopentyloxy group, a neopentyloxy group, a tert-pentyloxy group and a 1,2-dimethylpropoxy group.

The "$C_{3-8}$ cycloalkyl group" refers to a cyclopropyl group, a cyclobutyl group, a cyclopentyl group, a cyclohexyl group, a cycloheptyl group or a cyclooctyl group.

The "$C_{3-8}$ cycloalkane" refers to a cyclopropane, a cyclobutane, a cyclopentane, a cyclohexane, a cycloheptane or a cyclooctane.

The "$C_{3-8}$ cycloalkoxy group" refers to a cyclopropoxy group, a cyclobutoxy group, a cyclopentyloxy group, a cyclohexyloxy group, a cycloheptyloxy group or a cyclooctyloxy group.

The "$C_{1-5}$ alkylene" may be exemplified by methylene, ethylene, methylmethylene, trimethylene, methylethylene, dimethylmethylene, tetramethylene, ethylethylene, and pentamethylene.

In the case where the "$C_{3-8}$ cycloalkoxy group" defined above is a $C_{3-8}$ cycloalkoxy group that has a $C_{1-5}$ alkylene group crosslinking two different carbon atoms in the ring, it may be exemplified by bicyclo[2.2.1]heptan-2-yl.

The "pharmaceutically acceptable salt" as referred to herein encompasses salts with inorganic acids such as sulfuric acid, hydrochloric acid, hydrobromic acid, phosphoric acid and nitric acid; salts with organic acids such as acetic acid, benzoic acid, oxalic acid, lactic acid, malic acid, tartaric acid, fumaric acid, maleic acid, citric acid, malonic acid, mandelic acid, gluconic acid, galactaric acid, glucoheptonic acid, glycolic acid, glutamic acid, trifluoroacetic acid, methanesulfonic acid, ethanesulfonic acid, benzenesulfonic acid, p-toluenesulfonic acid, camphorsulfonic acid and naphthalene-2-sulfonic acid; salts with one or more metal ions such as lithium ion, sodium ion, potassium ion, calcium ion, magnesium ion, zinc ion and aluminum ion; and salts with ammonia or amines such as arginine, lysine, piperazine, choline, diethylamine, 4-phenylcyclohexylamine, 2-aminoethanol and benzathine. These salts can be obtained by conversion from free forms in a conventional manner.

Preferred embodiments of Inventive Compounds are as follows:

In the compounds, $R^2$ is preferably any structure of the following formula group (IIIB):

[Formula 17]

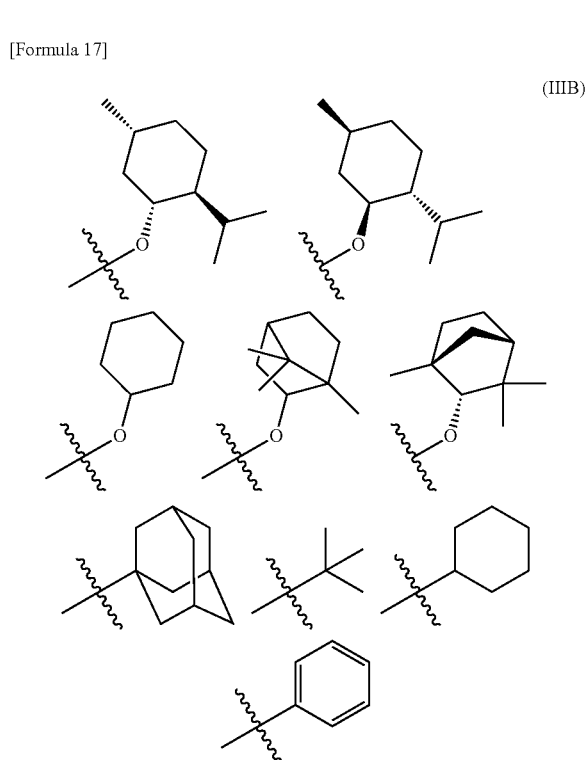

(IIIB)

Alternatively, in the compounds of another embodiment, $R^2$ is any structure of the following formula group (IIIA):

[Formula 18]

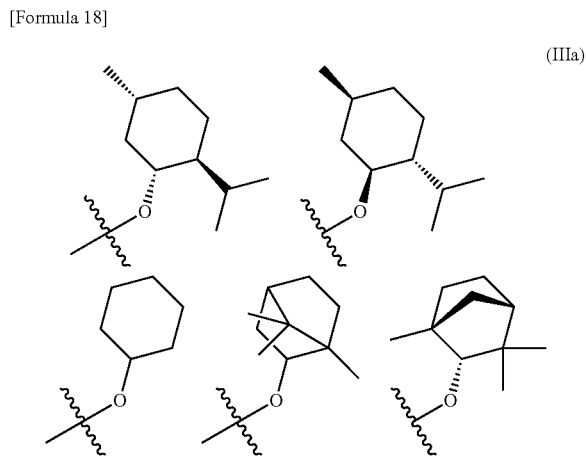

(IIIa)

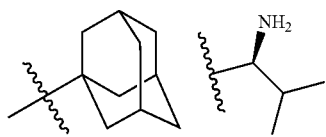

In the compounds, $R^2$ is more preferably any structure of the following formula group (IIIa'):

[Formula 19]

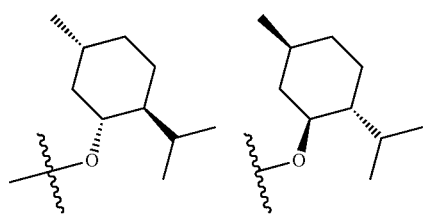

In the compounds of a further alternative embodiment, $R^2$ is further preferably any structure of the following formula group (IIIb):

[Formula 20]

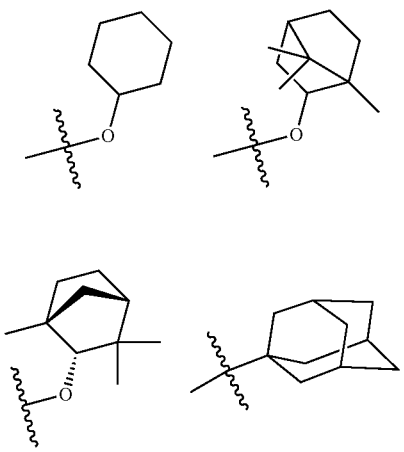

In the compounds, $R^3$ is preferably a hydrogen atom or a methyl group, more preferably a methyl group.

When $R^3$ is a $C_{1-6}$ alkyl group, the configuration of $R^3$ in the compounds is preferably a configuration represented by the following formula (IVa):

[Formula 21]

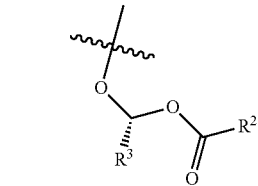

When $R^3$ is a methyl group, the configuration of $R^3$ in the compounds is preferably a configuration represented by the following formula (IVb):

[Formula 22]

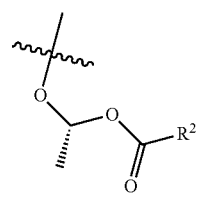

Preferred examples of Inventive Compounds include the following compounds or pharmaceutically acceptable salts thereof:

(1R,2R,3R,5R,6R)-2-amino-6-fluoro-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-2-({1-[({[(1S,2R,5S)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-3-[(4-fluorophenyl)methoxy]-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-3-propoxy-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic acid, (1R,2R,3R,5R,6R)-2-amino-6-fluoro-2-({(1S)-1-[(tricyclo[3.3.1.1$^{3,7}$]decane-1-carbonyl)oxy]ethoxy}carbonyl)-3-{[4-(trifluoromethyl)phenyl]methoxy}bicyclo[3.1.0]hexane-6-carboxylic acid, (1R,2R,3R,5R,6R)-2-amino-6-fluoro-3-[(3-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(1R)-1-(4-fluoro-3-methoxyphenyl)ethoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(5-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-3-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-methylphenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-(3-methylbutoxy)-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-(cyclopentyloxy)-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(3-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid, (1R,2R,3R,5R,6R)-2-amino-2-({[(2,2-dimethylpropanoyl)oxy]methoxy}carbonyl)-6-fluoro-3-[(4-fluorophenyl)methoxy]bicyclo[3.1.0]hexane-6-carboxylic acid, (1R,2R,3R,5R,6R)-2-amino-2-{[(benzoyloxy)methoxy]carbonyl}-6-fluoro-3-[(4-fluorophenyl)methoxy]bicyclo[3.1.0]hexane-6-carboxylic acid, (1R,2R,3R,5R,6R)-2-amino-2-({[(cyclohexanecarbonyl)oxy]methoxy}carbonyl)-6-fluoro-3-[(4-fluorophenyl)methoxy]bicyclo[3.1.0]hexane-6-carboxylic acid, and (1S,2R,3R,5R,6S)-2-amino-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid.

More preferred examples of Inventive Compounds include the following compounds or pharmaceutically acceptable salts thereof:

(1R,2R,3R,5R,6R)-2-amino-6-fluoro-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl)methoxy]-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(3,4-difluorophenyl)methoxy]-6-fluoro-2-({[(tricyclo[3.3.1.1$^{3,7}$]decane-1-carbonyl)oxy]methoxy}carbonyl)bicyclo[3.1.0]hexane-6-carboxylic acid, (1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid, (1R,2R,3R,5R,6R)-2-amino-6-fluoro-2-({(1S)-1-[(tricyclo[3.3.1.1$^{3,7}$]decane-1-carbonyl)oxy]ethoxy}carbonyl)-3-{[4-(trifluoromethyl)phenyl]methoxy}bicyclo[3.1.0]hexane-6-carboxylic acid, (1R,2R,3R,5R,6R)-2-amino-6-fluoro-3-[(3-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(1R)-1-(4-fluoro-3-methoxyphenyl)ethoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(5-chloropyridin-2-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-3-yl)methoxy]-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-methylphenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-(3-methylbutoxy)-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-(cyclopentyloxy)-6-fluoro-2-({(1S)-1-[(tricyclo[3.3.1.1$^{3,7}$]decane-1-carbonyl)oxy]ethoxy}carbonyl)bicyclo[3.1.0]hexane-6-carboxylic acid, and (1S,2R,3R,5R,6S)-2-amino-3-[(4-fluorophenyl)methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid.

When Inventive Compounds form hydrates or solvates, such hydrates and solvates are also included in the scope of the present invention. Pharmaceutically acceptable salts of hydrates or solvates of Inventive Compounds are also included in the scope of the present invention.

Inventive Compounds encompass all of forms such as enantiomers, diastereomers, equilibrium compounds, mixtures thereof in any proportions, and racemates.

Inventive Compounds also encompass those in which one or more hydrogen atoms, carbon atoms, nitrogen atoms, oxygen atoms or fluorine atoms have been replaced by their radioisotopes or stable isotopes. These labeled compounds are useful in, for example, studies of metabolism and pharmacokinetics, or biological analyses in which they are used as receptor ligands.

Inventive Compounds may be combined with one or more pharmaceutically acceptable carriers, excipients or diluents to formulate pharmaceutical preparations. Examples of the carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzoates, talc, magnesium stearate, stearic acid, glycerin, and various oils such as sesame oil, olive oil and soybean oil.

After being mixed with such carriers, excipients or diluents and, as needed, common additives such as extenders, binders, disintegrants, pH regulators or solubilizers, Inventive Compounds may be formulated by common pharmaceutical techniques into oral or parenteral drugs, such as tablets, pills, capsules, granules, powders, solutions, emulsions, suspensions, ointments, injections or skin patches, and especially formulated as prodrugs of group 2 metabotropic glutamate receptor antagonists.

Inventive Compounds may be orally or parenterally administered to adult patients in an amount of 0.01 to 500 mg as a single dose or in divided doses per day, but oral administration is preferred in terms of easy medication and drug efficacy. This dosage and the number of doses may be increased or decreased as appropriate for the type of disease to be treated, the age, body weight and symptom of the patients, etc.

Inventive Compounds (I-A) and (I) do not influence group 2 metabotropic glutamate receptors. However, Inventive Compounds (I-A) and (I) are each hydrolyzed in vivo enzymatically or chemically into Compound (II)-A, (II)-1, (II)-2, or (II)-3 which has a strong action on group 2 metabotropic glutamate receptors. Accordingly, Inventive Compounds perform functions as drugs that act on group 2 metabotropic glutamate receptors.

That is, Inventive Compounds act as prodrugs that enhance the membrane permeability (e.g., oral absorbability) of active form (II)-A, (II)-1, (II)-2 or (II)-3 having an antagonistic effect on group 2 metabotropic glutamate receptors and increase the in vivo exposure of the active form, thus serving as agents for prevention or treatment of conditions in which group 2 metabotropic glutamate receptors are said to be involved, such as mood disorders (including depression and bipolar disorder), anxiety disorder, cognitive disorders, developmental disorders, Alzheimer's disease, Parkinson's disease, movement disorders associated with muscular rigidity, sleep disorders, Huntington's chorea, eating disorders, drug dependence, epilepsy, brain infarction, cerebral ischemia, cerebral insufficiency, cerebral edema, spinal cord disorders, head trauma, inflammation and immune-related diseases.

A representative production process for Inventive Compounds represented by (I-B) and (I) is depicted by Scheme A shown below. The following process is an example of production processes for Inventive Compounds and is by no means intended to limit the scope of the present invention. In the following example of production processes, the compounds may form salts that do not interfere with reaction. Active forms represented by (II)-B and (II) may be produced by the production process described in WO03/061698 or WO2011/061935.

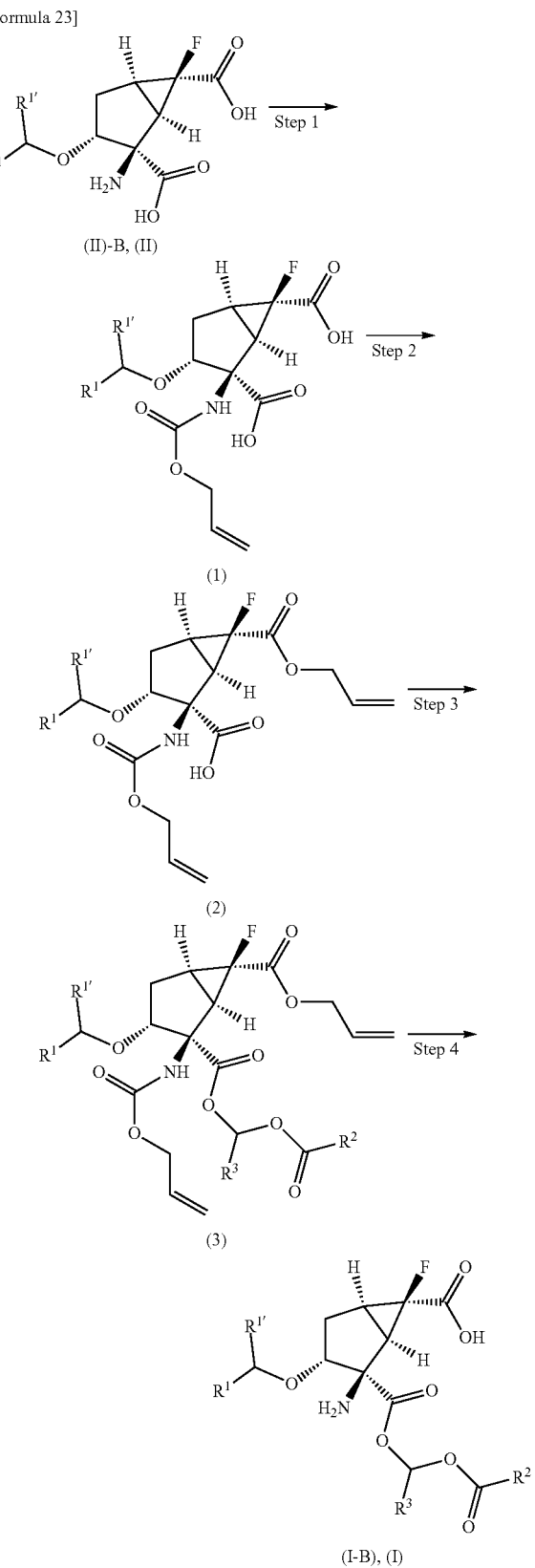

Scheme A

[Formula 23]

wherein the symbols are as defined above.

Step 1: Compounds (II)-B and (II) may be converted to Compound (1) through common protection of the amino group of Compound (II) with an allyloxycarbonyl group (see Protective Groups in Organic Synthesis, fourth edition, John Wiley & Sons, Inc.). This conversion may be accomplished, for example, through reaction with allyl chloroformate in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence or absence of an organic base (e.g., triethylamine, pyridine, N-methylmorpholine, diisopropylethylamine, 4-(N,N-dimethylamino)pyridine, 2,6-di-t-butylpyridine) or an inorganic base (e.g., potassium carbonate, sodium carbonate, sodium bicarbonate).

Step 2: Compound (1) may be reacted with allyl chloroformate in an inert solvent such as a halogenated solvent (e.g., dichloromethane), an ether solvent (e.g., tetrahydrofuran) or dimethyl sulfoxide, in the presence of an organic base (e.g., tributylamine, triethylamine, diisopropylethylamine, pyridine, N-methylmorpholine), and then converted to Compound (2) by the addition of N,N-dimethyl-4-aminopyridine. Alternatively, Compound (1) may also be converted to Compound (2) through the reaction of the carboxy group of Compound (1) with allyl alcohol by common esterification (see Comprehensive Organic Transformations, Second Edition, 1999, John Wiley & Sons, Inc.).

Step 3: Compound (2) may be converted to Compound (3) through reaction with a compound of formula L-CH($R^3$)—O—C(O)—$R^2$ (wherein L is a leaving group such as a halogen atom, a p-toluenesulfonyloxy group, a methanesulfonyloxy group, or a trifluoromethanesulfonyloxy group) in the presence or absence of a suitable activator such as sodium iodide, in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence of an inorganic base (e.g., sodium hydride, potassium hydride, potassium carbonate, sodium carbonate, sodium bicarbonate, cesium carbonate, cesium bicarbonate, sodium hydroxide, potassium hydroxide), a metal amide (e.g., lithium bis(trimethylsilyl)amide, lithium diisopropylamide, sodium amide), an organic base (e.g., triethylamine, pyridine, diisopropylethylamine, 4-(N,N-dimethylamino)pyridine, 2,6-di-tert-butylpyridine) or a base (e.g., potassium tert-butoxide). Preferably, Compound (2) may be converted to Compound (3) through reaction with a compound represented by formula Cl—CH($R^3$)—O—C(O)—$R^2$ or Br—CH($R^3$)—O—C(O)—$R^2$ in a mixed solvent of chloroform and water in the presence of potassium carbonate and tetrabutylammonium sulfate at room temperature to 80° C. for 2 hours to 1 day.

Step 4: Compound (3) may be converted to Compound (I), an Inventive Compound, through common deprotection (see Protective Groups in Organic Synthesis, fourth edition, John Wiley & Sons, Inc.). This conversion may be accomplished, for example, through deprotection of the allyl group and the allyloxycarbonyl group in the presence of a zero-valent palladium catalyst such as tetrakis(triphenylphosphine)palladium(0) and a regeneration reagent for metal catalyst, such as 1,3-dimethylbarbituric acid, for example, in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane) or any mixture thereof. Preferably, Compound (3) may be converted to Inventive Compounds (I-B) and (I) through reaction performed in chloroform in the presence of tetrakis(triphenylphosphine)palladium(0) and 1,3-dimethylbarbituric acid at room temperature to 50° C. for 2 to 8 hours.

A representative production process for compounds represented by (II)-C which are active forms of Inventive Compounds represented by (I-C) is depicted by Scheme B shown below. The following process is an example of production processes for Inventive Compounds and is by no means intended to limit the scope of the present invention. In the following example of production processes, the compounds may form salts that do not interfere with reaction.

Scheme B

[Formula 24]

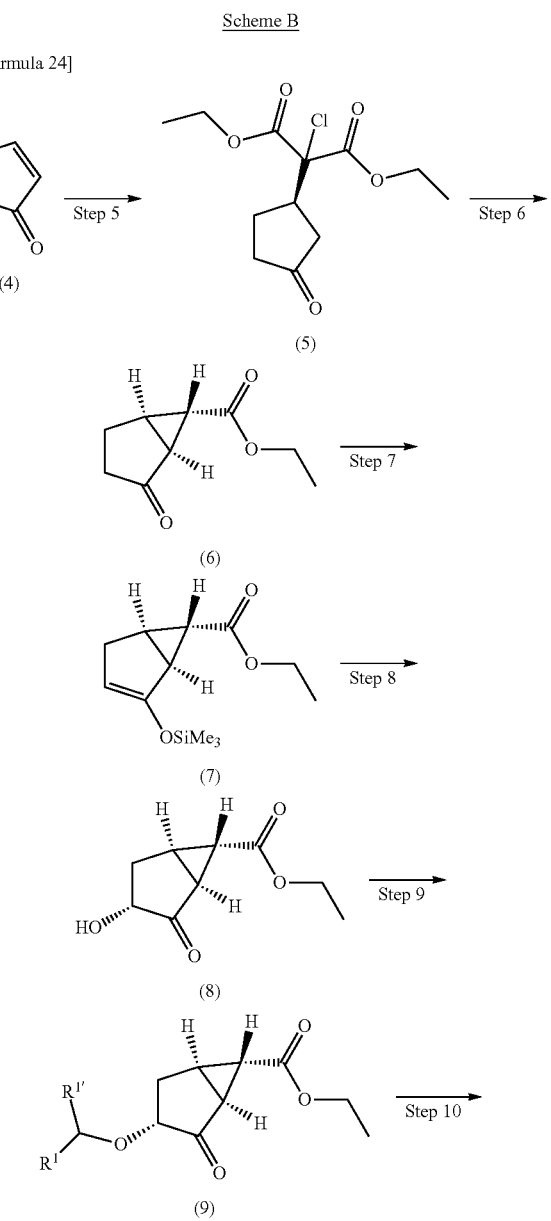

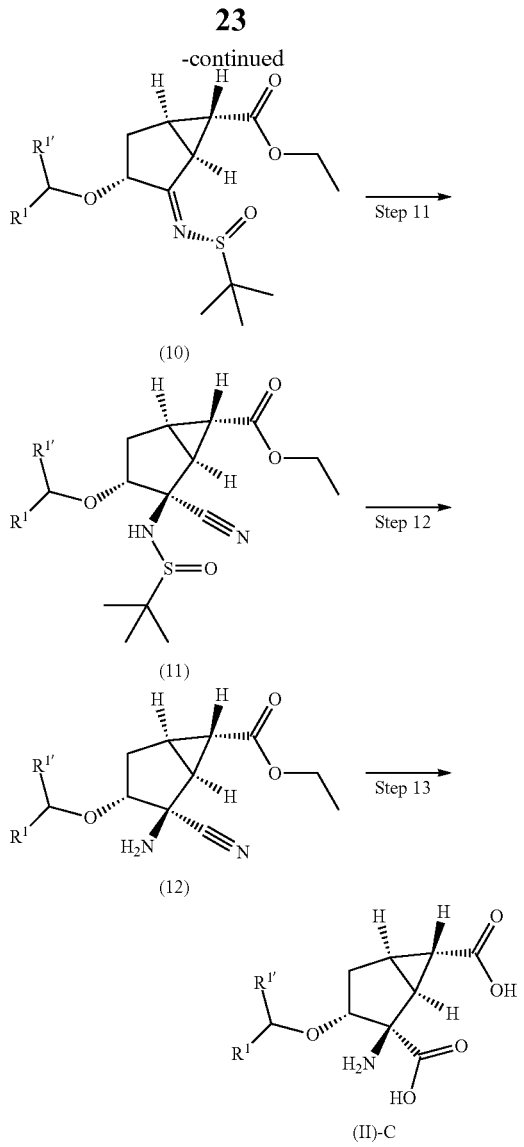

wherein the symbols are as defined above.

In the production process shown in the present invention, Compound (4) may be converted to optically active Inventive Compound (6) in 2 steps through catalytic asymmetric Michael addition reaction and subsequent cyclization reaction involving removal of ethoxycarbonyl. Compound (6) may also be synthesized in accordance with the following reports (see Tetrahedron Asymmetry, 1997, 511-514; Chem. Eur. J., 2006, 12, 568-575; J. Org. Chem., 2008, 73, 3078-3087; and Tetrahedron Asymmetry, 2010, 1486-1493).

Step 5: Compound (4) may be converted to Compound (5) through asymmetric Michael addition reaction. For example, a suspension containing an asymmetric catalyst is prepared in an inert solvent such as a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide or any mixture thereof, in the presence or absence of an additive (e.g., lithium aluminum hydride, (R)-(+)-1,1-bi-2-naphthol, Molecular Sieves 4A), and then, Compound (4) may be converted to Compound (5) through reaction with diethyl chloromalonate in the presence or absence of an organic base (e.g., triethylamine, pyridine, N-methylmorpholine, diisopropylethylamine, 4-(N,N-dimethylamino)pyridine, 2,6-di-t-butylpyridine, potassium tert-butoxide) or an inorganic base (e.g., potassium carbonate, sodium carbonate, sodium bicarbonate), etc. Preferably, a suspension containing an asymmetric catalyst is prepared through reaction at 0 to 70° C. for 30 minutes to 1 day in tetrahydrofuran in the presence of lithium aluminum hydride and (R)-(+)-1,1-bi-2-naphthol, and then, Compound (4) may be converted to Inventive Compound (5) through reaction with diethyl chloromalonate in the presence of Molecular Sieves 4A and sodium carbonate at 0 to 70° C. for 30 minutes to 1 day (see Angew. Chem., Int. Ed. Engl., 1996, 35, 104-106; and Tetrahedron, 2002, 58, 2585-2588).

Step 6: Compound (5) may be converted to Compound (6) through cyclization reaction involving removal of ethoxycarbonyl. This conversion may be accomplished, for example, through reaction with an inorganic salt (e.g., lithium chloride, sodium chloride, sodium cyanide, potassium cyanide, sodium bromide, lithium iodide, sodium iodide, lithium carbonate, potassium carbonate, sodium carbonate, sodium phosphate) or an organic salt (e.g., tetramethylammonium acetate), in an inert solvent such as an alcohol solvent (e.g., methanol, ethanol, 2-propanol, tert-butyl alcohol, 2,2,2-trifluoroethanol, 1,1,1,3,3,3-hexafluoro-2-propanol), a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence or absence of an acid (e.g., acetic acid, citric acid, formic acid). Preferably, Compound (5) may be converted to Inventive Compound (6) through reaction with lithium chloride in a N-methyl-2-pyrrolidinone solvent in the presence of acetic acid at 0 to 180° C. for 30 minutes to 1 day (see J. Org. Chem., 1978, 43, 138-147; and Org. Process Res. Dev., 2012, 16, 129-140).

Step 7: Compound (6) may be converted to Compound (7) through reaction with a silylating agent. This conversion may be accomplished, for example, through reaction with an organic base (e.g., triethylamine, diisopropylethylamine, N-methylmorpholine, diazabicycloundecene, diazabicyclononene, pyridine), a metal amide base (e.g., lithium diisopropylamide, lithium hexamethyldisilazide, sodium hexamethyldisilazide, potassium hexamethyldisilazide), an alkali metal hydride base (e.g., sodium hydride, potassium hydride) and a silylating agent (e.g., chlorotrimethylsilane, bromotrimethylsilane, iodotrimethylsilane, trimethylsilyl trifluoromethanesulfonate) in an inert solvent such as a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence or absence of an additive (e.g., sodium iodide, potassium iodide, tetrabutylammonium iodide, sodium bromide, potassium bromide). Preferably, Compound (6) may be converted to Inventive Compound (7) through reaction with triethylamine and trimethylsilyl trifluoromethanesulfonate in a toluene solvent at −20 to 80° C. for 30 minutes to 1 day (see J. Med. Chem., 2000, 43, 4893-4909; and Bioorg. Med. Chem., 2002, 10, 433-436).

Step 8: Compound (7) may be converted to Compound (8) through reaction with an oxidizing agent. This conversion may be accomplished, for example, through reaction with peracid (e.g., 3-chloroperbenzoic acid, perbenzoic acid, monoperoxyphthalic acid, monoperoxyphthalic acid magnesium salt, peracetic acid); hydrogen peroxide in the presence of a catalyst (e.g., methyltrioxorhenium or tris(cetylpyridinium)peroxotungstophosphate (PCWP)); hydrogen peroxide in the presence of a nitrile compound (e.g., trichloroacetonitrile or acetonitrile); hydrogen peroxide in the presence of a nitrile compound (e.g., trichloroacetonitrile or acetonitrile) and a ketone compound (e.g., acetone); oxone ($2KHSO_5 \cdot KHSO_4 \cdot K_2SO_4$) in the presence of a ketone compound (e.g., acetone); or an oxidizing agent such as dimethyldioxirane, tert-butyl hydroperoxide, osmium tetroxide and N-methylmorpholine-N-oxide, lead tetraacetate, iodosylbenzene and a boron trifluoride-diethyl ether complex, chromyl chloride, or ozone, in an inert solvent such as a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, acetonitrile, water or any mixture thereof, in the presence or absence of an additive (e.g., sodium bicarbonate, potassium bicarbonate, potassium carbonate, sodium carbonate, calcium hydroxide, potassium dihydrogenphosphate, dipotassium hydrogenphosphate, sodium dihydrogenphosphate, disodium hydrogenphosphate, pyridine, acetic acid) (see Organic Reactions, 2003, 62, 1-356). Preferably, Compound (7) may be converted to Inventive Compound (8) through reaction with methyltrioxorhenium and hydrogen peroxide in an acetonitrile solvent in the presence of pyridine and acetic acid at −20 to 80° C. for 30 minutes to 1 day.

Step 9: Compound (8) may be converted to Compound (9) through reaction with an alkylating agent. This conversion may be accomplished through reaction with a compound represented by formula $R^1R^5CHOC(=NH)CCl_3$ in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, tetrahydropyran, diethyl ether, 1,2-dimethoxyethane), an amide solvent (e.g., N,N-dimethylformamide, N-methyl-2-pyrrolidinone), dimethyl sulfoxide, water or any mixture thereof, in the presence of a Bronsted acid (e.g., trifluoromethanesulfonic acid, bistrifluoromethanefluoromethanesuflonimide, trifluoroacetic acid, hydrogen chloride, perchloric acid) or a Lewis acid (e.g., a boron trifluoride-diethyl ether complex, zinc chloride, tin chloride, trimethylsilyl trifluoromethanesulfonate, scandium(III) trifluoromethanesulfonate, ytterbium(III) trifluoromethanesulfonate). The compound represented by formula $R^1R^5CHOC(=NH)CCl_3$ can be obtained through the reaction of an alcohol represented by formula $R^1R^5CHOH$ with trichloroacetonitrile in the presence of a base in accordance with documented methods (see J. Chem. Soc., Perkin Trans. 1, 1985, 2247-2250; and Tetrahedron Lett., 1996, 37, 1481-1484). Preferably, Compound (8) may be converted to Compound (9) through reaction with the compound represented by formula $R^1R^5CHOC(=NH)CCl_3$ in a tetrahydropyran solvent in the presence of trifluoromethanesulfonic acid at −20 to 50° C. for 30 minutes to 1 day (see J. Chem. Soc., Chem. Commun. 1981, 1240-1241; and J. Chem. Soc., Perkin Trans. 1, 1985, 2247-2250).

Alternatively, the conversion may be accomplished through reaction with a compound represented by formula $R^1R^5CH—X$ in the presence or absence of a suitable activator such as tetrabutylammonium iodide in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, tetrahydropyran, diethyl ether, 1,2-dimethoxyethane), an amide solvent (e.g., N,N-dimethylformamide, N-methyl-2-pyrrolidinone), dimethyl sulfoxide, water or any mixture thereof, in the presence of an inorganic base (e.g., sodium hydride, potassium hydride, potassium carbonate, sodium carbonate, cesium carbonate, potassium bicarbonate, sodium bicarbonate, sodium hydroxide, potassium hydroxide, silver(I) oxide, silver(I) carbonate, silver(I) trifluoromethanesulfonate), a metal amide base (e.g., lithium diisopropylamide, lithium hexamethyldisilazide, sodium hexamethyldisilazide, potassium hexamethyldisilazide), an organic base (e.g., triethylamine, diisopropylethylamine, N-methylmorpholine, diazabicycloundecene, diazabicyclononene, pyridine, 4-dimethylaminopyridine) or an alkoxide base (e.g., potassium tert-butoxide, sodium tert-pentoxide, potassium tert-pentoxide). In this context, X represents a leaving group other than $OC(=NH)CCl_3$, for example, a chlorine atom, a bromine atom, an iodine atom, a p-toluenesulfonyloxy group, a p-bromobenzenesulfonyloxy group, a p-chlorobenzenesulfonyloxy group, a p-nitrobenzenesulfonyloxy group, a benzenesulfonyloxy group, a methanesulfonyloxy group or a trifluoromethanesulfonyloxy group. Preferably, Compound (8) may be converted to Compound (9) through reaction with a compound represented by formula $R^1R^5CH—Cl$ in a chloroform solvent in the presence of silver(I) carbonate, silver(I) trifluoromethanesulfonate and tetrabutylammonium iodide at −20 to 50° C. for 30 minutes to 1 day.

Step 10: Compound (9) may be converted to Compound (10) through dehydrative condensation reaction with an optically active sulfinamide. This conversion may be accomplished, for example, through reaction with (R)-2-methyl-2-sulfinamide in an inert solvent such as an alcohol solvent (e.g., methanol, ethanol, 2-propanol, tert-butyl alcohol, 2,2,2-trifluoroethanol, 1,1,1,3,3,3-hexafluoro-2-propanol), a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence of a Lewis acid (e.g., titanium(IV) isopropoxide, titanium(IV) methoxide, titanium(IV) ethoxide, titanium(IV) propoxide, titanium(IV) butoxide). Preferably, Compound (9) may be converted to Inventive Compound (10) through reaction with (R)-2-methyl-2-sulfinamide in a tetrahydrofuran solvent in the presence of titanium(IV) ethoxide at 0 to 80° C. for 30 minutes to 1 day.

Step 11: Compound (10) may be converted to Compound (11) through cyano addition reaction (see Chem. Rev., 2011, 111, 6947-6983). This conversion may be accomplished, for example, through reaction by the addition of a cyanating agent (e.g., trimethylsilyl cyanide, hydrogen cyanide, sodium cyanide, potassium cyanide, acetone cyanohydrin, diethyl cyanophosphonate, diethyl aluminum cyanide, tert-butyldimethylsilyl cyanide, tributyltin cyanide) in an inert solvent such as an alcohol solvent (e.g., methanol, ethanol, 2-propanol, tert-butyl alcohol, 2,2,2-trifluoroethanol, 1,1,1,3,3,3-hexafluoro-2-propanol), a hydrocarbon solvent (e.g., benzene, toluene, hexane), a halogenated solvent (e.g., dichloromethane, chloroform, carbon tetrachloride, benzotrifluoride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence or absence of an inorganic base (e.g., cesium fluoride, potassium fluoride, sodium fluoride), a metal amide base (e.g., lithium diisopropylamide, lithium hexamethyldisilazide, sodium hexamethyldisilazide, potassium hexamethyldisilazide), an organic base (e.g., triethylamine, diisopropylethylamine, N-methylmorpholine, diazabicycloundecene, diazabicyclononene, pyridine, 4-dimethylaminopyridine) or an alkoxide base (e.g., potassium tert-butoxide, sodium tert-pentoxide, potassium tert-pentoxide). Preferably, Compound (10) may be converted to Inventive Compound (11) through reaction with trimethylsilyl cyanide in a tetrahydrofuran solvent in the presence of cesium fluoride at −20 to 80° C. for 30 minutes to 1 day.

Step 12: Compound (11) may be converted to Compound (12) through reaction with an acid catalyst. This conversion may be accomplished, for example, through reaction with a Bronsted acid (e.g., trifluoromethanesulfonic acid, bistrifluoromethanefluoromethanesuflonimide, trifluoroacetic acid, hydrogen chloride, perchloric acid) or a Lewis acid (e.g., a boron trifluoride-diethyl ether complex, zinc chloride, tin chloride, trimethylsilyl trifluoromethanesulfonate, scandium(III) trifluoromethanesulfonate, ytterbium(III) trifluoromethanesulfonate) in an inert solvent such as an alcohol solvent (e.g., methanol, ethanol, 2-propanol, tert-butyl alcohol, 2,2,2-trifluoroethanol, 1,1,1,3,3,3-hexafluoro-2-propanol), a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, tetrahydropyran, diethyl ether, 1,2-dimethoxyethane), an amide solvent (e.g., N,N-dimethylformamide, N-methyl-2-pyrrolidinone), dimethyl sulfoxide, water or any mixture thereof. Preferably, Compound (11) may be converted to Compound (12) through reaction with a hydrogen chloride/ethanol solution in a tetrahydrofuran solvent at −20 to 50° C. for 30 minutes to 1 day.

Step 13: Compound (12) may be converted to Compound (II)-C through reaction with hydrogen peroxide and a base (e.g., lithium hydroxide, sodium hydroxide, potassium hydroxide, potassium carbonate, sodium carbonate, ammonium hydroxide, sodium phosphate) or an aqueous solution thereof in the presence of an inert solvent (e.g., dimethyl sulfoxide). Preferably, Compound (12) may be converted to Compound (II)-C through reaction with hydrogen peroxide and an aqueous solution of sodium hydroxide in the presence of dimethyl sulfoxide at 0 to 100° C. for 30 minutes to 1 day (see Synthesis, 1989, 949-950; and Bull. Chem. Soc. Jpn., 1981, 54, 793-799).

A representative production process for Inventive Compounds represented by (I-C) is depicted by Scheme C shown below. The following process is an example of production processes for Inventive Compounds and is by no means intended to limit the scope of the present invention. In the following example of production processes, the compounds may form salts that do not interfere with reaction.

Scheme C

[Formula 25]

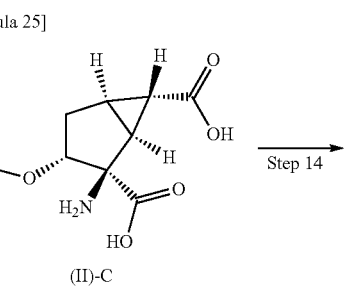

(II)-C

Step 14 →

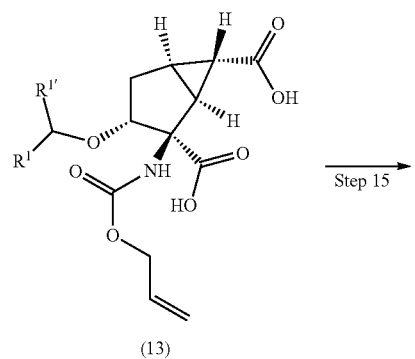

(13)

Step 15 →

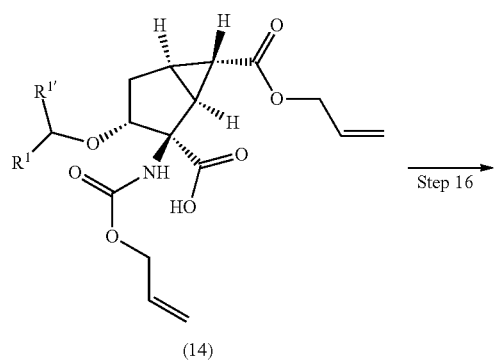

(14)

Step 16 →

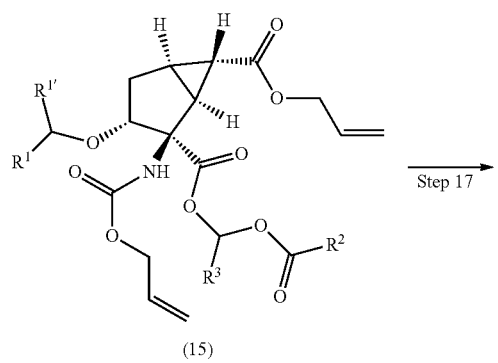

(15)

Step 17 →

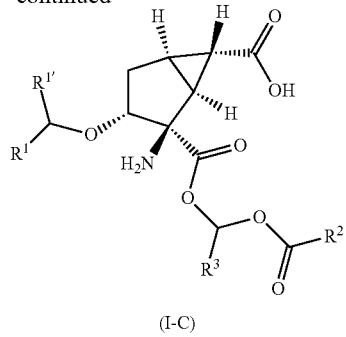

(I-C)

wherein the symbols are as defined above.

Step 14: Compound (II)-C may be converted to Compound (13) through common protection of the amino group of Compound (II)-C with an allyloxycarbonyl group (see Protective Groups in Organic Synthesis, fourth edition, John Wiley & Sons, Inc.). This conversion may be accomplished, for example, through reaction with allyl chloroformate in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence or absence of an organic base (e.g., triethylamine, pyridine, N-methylmorpholine, diisopropylethylamine, 4-(N,N-dimethylamino)pyridine, 2,6-di-t-butylpyridine) or an inorganic salt (e.g., potassium carbonate, sodium carbonate, sodium bicarbonate).

Step 15: Compound (13) may be reacted with allyl chloroformate in an inert solvent such as a halogenated solvent (e.g., dichloromethane), an ether solvent (e.g., tetrahydrofuran) or dimethyl sulfoxide, in the presence of an organic base (e.g., tributylamine, triethylamine, diisopropylethylamine, pyridine, N-methylmorpholine), and then converted to Compound (14) by the addition of N,N-dimethyl-4-aminopyridine. Alternatively, Compound (13) may also be converted to Compound (14) through the reaction of the carboxy group of Compound (13) with allyl alcohol by common esterification (see Comprehensive Organic Transformations, Second Edition, 1999, John Wiley & Sons, Inc.).

Step 16: Compound (14) may be converted to Compound (15) through reaction with a compound of formula L-CH(R$^3$)—O—C(O)—R$^2$ (wherein L is a leaving group such as a halogen atom, a p-toluenesulfonyloxy group, a methanesulfonyloxy group, or a trifluoromethanesulfonyloxy group) in the presence or absence of a suitable activator such as sodium iodide, in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide solvent (e.g., N,N-dimethylformamide, N-methyl-2-pyrrolidinone), dimethyl sulfoxide, water or any mixture thereof, in the presence of an inorganic base (e.g., sodium hydride, potassium hydride, potassium carbonate, sodium carbonate, sodium bicarbonate, cesium carbonate, cesium bicarbonate, sodium hydroxide, potassium hydroxide), a metal amide (e.g., lithium bis(trimethylsilyl)amide, lithium diisopropylamide, sodium amide), an organic base (e.g., triethylamine, pyridine, diisopropylethylamine, 4-(N,N-dimethylamino)pyridine, 2,6-di-tert-butylpyridine) or a base (e.g., potassium tert-butoxide). Preferably, Compound (14) may be converted to Compound (15) through reaction with a compound represented by formula Cl—CH(R$^3$)—O—C(O)—R$^2$ or Br—CH(R$^3$)—O—C(O)—R$^2$ in a mixed solvent of chloroform and water in the presence of potassium carbonate and tetrabutylammonium hydrogen sulfate at room temperature to 80° C. for 2 hours to 1 day.

Step 17: Compound (15) may be converted to Inventive Compound (I-C) through common deprotection (see Protective Groups in Organic Synthesis, fourth edition, John Wiley & Sons, Inc.). This conversion may be accomplished, for example, through deprotection of the allyl group and the allyloxycarbonyl group in the presence of a zero-valent palladium catalyst such as tetrakis(triphenylphosphine)palladium(0) and a regeneration reagent for metal catalyst, such as 1,3-dimethylbarbituric acid in an inert solvent such as, for example, a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane) or any mixture thereof. Preferably, Compound (15) may be converted to Inventive Compound (I-C) through reaction performed in chloroform in the presence of tetrakis(triphenylphosphine)palladium(0) and 1,3-dimethylbarbituric acid at room temperature to 50° C. for 2 to 8 hours.

The present invention is described below in more detail by means of examples and tests which are not intended to limit the scope of the invention and may be modified unless they depart from the scope of the invention.

The "Grace" used in the purification by column chromatography in the examples below is Reveleris Silica Flash Cartridge from W.R. Grace & Co. The "YMC C18" used is YMC-DispoPack AT ODS-25 from YMC Co., Ltd.

The columns from Daicel Corp., flow rates, and analysis and separation times used in the resolution of diastereomers by chiral column chromatography in the examples below are shown below.

CHIRAL PAK IC-3: particle size: 3 µm, inside diameter: 4.6 mm, length: 150 mm, flow rate: 1.0 mL/min.
CHIRAK PAK ID-3: particle size: 3 µm, inside diameter: 4.6 mm, length: 150 mm, flow rate: 1.0 mL/min.
CHIRAK PAK AY-3: particle size: 3 µm, inside diameter: 4.6 mm, length: 150 mm, flow rate: 1.0 mL/min.
CHIRAL PAK IC: particle size: 5 µm, inside diameter: 20 mm, length: 250 mm, flow rate: 10 mL/min.
CHIRAL PAK ID: particle size: 5 µm, inside diameter: 20 mm, length: 250 mm, flow rate: 10 mL/min.

In the production examples and the examples below, purification by preparative high-performance liquid chromatography (HPLC) was performed under the following conditions:
Machine: Trilution LC from Gilson, Inc.
Column: YMC-Actus Triant from YMC Co., Ltd., 5.0 µm, 50×30 mm
Solvent: solution A; water containing 0.1% trifluoroacetic acid, solution B; acetonitrile containing 0.1% trifluoroacetic acid, or solution A; water containing 0.1% formic acid, solution B; acetonitrile containing 0.1% formic acid
Gradient: 0 min (solution A/solution B=90/10), 11 min (solution A/solution B=20/80), 12 to 13.5 min (solution A/solution B=5/95)
Flow rate: 40 mL/min The instrument data shown in the examples below were obtained by measurement with the following instruments.
MS spectrum: LCMS-IT-TOF (ESI/APCI dual source) (Shimadzu Corp.), 1290 Infinity and 6130 Quadrupole LC/MS (Agilent Technologies, Inc.)

NMR spectrum [¹H-NMR]: 600 MHz; JNM-ECA600 (JEOL Ltd.), 400 MHz; AVENCEIIIHD 400 (Bruker Corp.)

X-ray structure analysis: R-AXIS RAPID II (Rigaku Corp.)

The abbreviations used in the examples to show nuclear magnetic resonance (NMR) spectra are as follows:

s: singlet, d: doublet, t: triplet, q: quartet, sxt: sixtet, dd: doublet doublet, ddd: doublet doublet doublet, dt: doublet triplet, td: triplet doublet, qd: quartet doublet, m: multiplet, br: broad, J: coupling constant, Hz: hertz, CHLOROFORM-d: deuterated chloroform, DMSO-d6: deuterated dimethyl sulfoxide, MeOH-d4: deuterated methanol In the reference example and examples below, compounds were named using ACD/Name 2015 (ACD/Labs 2015, Advanced Chemistry Development Inc.).

In the reference example and examples, the terms and the reagents given below were indicated as follows:

MgSO₄ (magnesium sulfate), Na₂SO₄ (anhydrous sodium sulfate), NaHCO₃ (sodium bicarbonate), NH₄Cl (ammonium chloride), DMF (N,N-dimethylformamide), EtOAc (ethyl acetate), CHCl₃ (chloroform), THF (tetrahydrofuran), MeOH (methanol), EtOH (ethanol), IPA (isopropyl alcohol), H₂O (water), Pd(PPh₃)₄ [tetrakis(triphenylphosphine)palladium(0)], brine (saturated saline), HCl (hydrogen chloride).

Example 1 Synthesis of (1R,2R,3R,5R,6R)-2-amino-6-fluoro-3-[(4-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid To a solution of Compound (II)-1 (1.5 g, 4.58 mmol) (see WO03/061698) in 1,4-dioxane (9.2 mL), a saturated aqueous solution of NaHCO₃ (16 mL, 18.32 mmol) was added, and the mixture was stirred at room temperature for 10 minutes. Allyl chloroformate (0.96 mL, 9.17 mmol) was added dropwise, and the mixture was stirred at room temperature for 18 hours. The solution was basified by the addition of water and a saturated aqueous solution of NaHCO₃ and then washed with EtOAc. Subsequently, the solution was acidified by the addition of 2 M hydrochloric acid to the aqueous layer, followed by extraction using EtOAc. Then, the organic layer was dried over Na₂SO₄. The insoluble was filtered, the filtrate was concentrated under reduced pressure to obtain the title compound (1.9 g) (brown amorphous).

1H NMR (600 MHz, DMSO-d6) δ ppm 2.05-2.11 (1H, m), 2.13-2.21 (1H, m), 2.31-2.37 (1H, m), 2.51-2.52 (1H, m), 2.68-2.74 (1H, m), 3.31 (1H, s), 4.05-4.10 (1H, m), 4.39-4.52 (3H, m), 4.57-4.64 (1H, m), 5.16-5.24 (1H, m), 5.28-5.36 (1H, m), 5.84-5.96 (1H, m), 7.12-7.17 (2H, m), 7.29-7.34 (2H, m), 8.14 (1H, s)

MS m/z: 434 [M+Na]+

(2) (1R,2R,3R,5R,6R)-6-Fluoro-3-[(4-fluorophenyl)methoxy]-6-{[(prop-2-en-1-yl)oxy]carbonyl}-2-({[(prop-2-en-1-yl)oxy]carbonyl}amino)bicyclo[3.1.0]hexane-2-carboxylic Acid

[Formula 26]

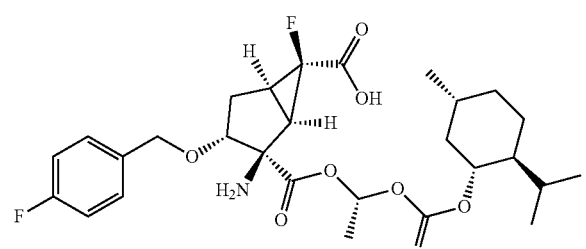

(1) (1R,2R,3R,5R,6R)-6-Fluoro-3-[(4-fluorophenyl)methoxy]-2-({[(prop-2-en-1-yl)oxy]carbonyl}amino)bicyclo[3.1.0]hexane-2,6-dicarboxylic Acid

[Formula 27]

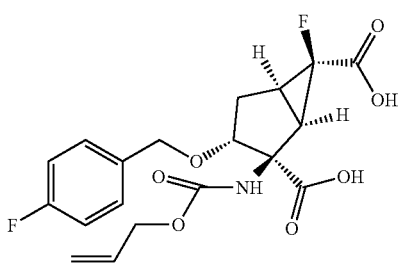

[Formula 28]

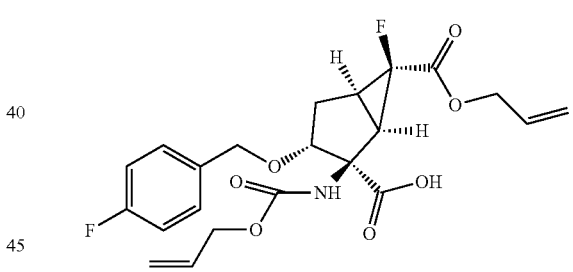

To a solution of the compound (0.95 g, 2.31 mmol) obtained in Step (1) and N-methylmorpholine (0.38 mL, 3.46 mmol) in THF (10 mL), allyl chloroformate (0.36 mL, 3.46 mmol) was added dropwise at 0° C., and the mixture was stirred for 30 minutes. N,N-Dimethyl-4-aminopyridine (0.070 g, 0.58 mmol) was added, and the mixture was warmed to room temperature and stirred for 2.5 hours. The solution was acidified by the addition of water and 2 M hydrochloric acid, followed by extraction using EtOAc. The organic layer was dried over Na₂SO₄. The insoluble was filtered, the filtrate was concentrated under reduced pressure to obtain the title compound (1.0 g) (brown amorphous).

1H NMR (600 MHz, CHLOROFORM-d) δ ppm 2.20-2.28 (1H, m), 2.35-2.47 (2H, m), 2.91-3.07 (1H, m), 3.83-3.92 (1H, m), 4.43-4.69 (6H, m), 5.11-5.37 (5H, m), 5.83-5.96 (2H, m), 6.95-7.03 (2H, m), 7.20-7.24 (2H, m)

MS m/z: 474 [M+Na]+

(3) (1R,2R,3R,5R,6R)-2-Amino-6-fluoro-3-[(4-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid (Example 1)

[Formula 29]

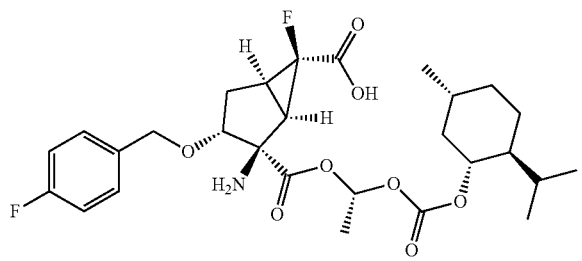

To a solution of the compound (0.30 g, 0.66 mmol) obtained in Step (2) in DMF (3.3 mL), $K_2CO_3$ (0.096 g, 0.70 mmol) and 18-crown-6 (0.15 mL, 0.70 mmol) were added. (1R)-1-Chloroethyl (1R,2S,5R)-5-methyl-2-(propan-2-yl)cyclohexyl carbonate (see WO2013/180271) (0.42 g, 1.59 mmol) was added, and the mixture was stirred at room temperature for 18 hours. The reaction solution was added dropwise to a saturated aqueous solution of $NH_4Cl$, followed by extraction using EtOAc. The organic layer was washed with brine. After drying over $Na_2SO_4$, the insoluble was filtered, and filtrate was concentrated under reduced pressure. The resulting residue was purified by silica gel column chromatography (Grace 12 g, n-Hexane/EtOAc=95/5 to 60/40) and (Grace 12 g, n-Hexane/EtOAc=95/5 to 80/20) to obtain a colorless oil (0.31 g). This oil was dissolved in $CHCl_3$ (2.3 mL). To the solution, 1,3-dimethylbarbituric acid (0.072 g, 0.46 mmol) and $Pd(PPh_3)_4$ (0.013 g, 0.01 mmol) were added, and the mixture was stirred at room temperature for 1 hour. The reaction solution was concentrated under reduced pressure, and the residue was purified by reverse-phase silica gel column chromatography (YMC C18 12 g, $H_2O$/MeCN=95/5 to 5/95). The fraction was concentrated. MeOH was added to the resulting residue, and the mixture was stirred at room temperature for 1 hour. Then, the resulting crystals were collected by filtration to obtain the title compound (0.097 g) (colorless solid).

1H NMR (600 MHz, DMSO-d6) δ ppm 0.69-0.90 (10H, m), 0.92-1.08 (1H, m), 1.32-1.46 (5H, m), 1.62 (2H, br d, J=11.6 Hz), 1.79-2.06 (5H, m), 2.21-2.27 (1H, m), 2.29-2.36 (1H, m), 3.66-3.78 (1H, m), 4.39-4.48 (2H, m), 4.55 (1H, br d, J=11.6 Hz), 6.64-6.73 (1H, m), 7.09-7.22 (2H, m), 7.22-7.36 (2H, m)

MS m/z: 576 [M+Na]+

Example 2 (1R,2R,3R,5R,6R)-2-Amino-6-fluoro-3-[(4-fluorophenyl)methoxy]-2-({(1S)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid

[Formula 30]

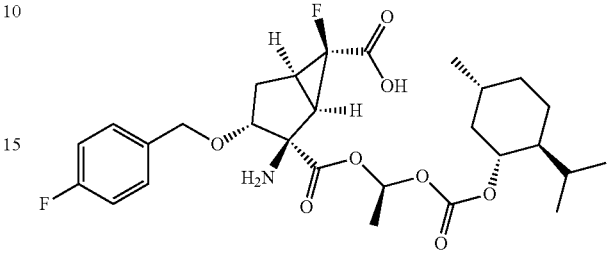

The title compound (0.018 g) was obtained (colorless solid) by the same procedure as in Example 1-(3) using the compound (0.30 g, 0.66 mmol) obtained in Example 1-(2) and (1S)-1-chloroethyl (1R,2S,5R)-5-methyl-2-(propan-2-yl)cyclohexyl carbonate (see WO2013/180271) (0.42 g, 1.59 mmol).

1H NMR (600 MHz, DMSO-d6) δ ppm 0.65 (3H, d, J=7.0 Hz), 0.73-0.86 (7H, m), 0.93-1.01 (2H, m), 1.23-1.32 (1H, m), 1.39-1.45 (4H, m), 1.53-1.61 (2H, m), 1.71-1.79 (1H, m), 1.89-1.97 (2H, m), 2.04-2.12 (1H, m), 2.10-2.20 (1H, m), 2.22-2.29 (1H, m), 2.48-2.49 (2H, m), 3.64-3.70 (1H, m), 4.36-4.44 (2H, m), 4.49-4.53 (1H, m), 6.64 (1H, q, J=5.4 Hz), 7.09 (2H, s), 7.26-7.30 (2H, m)

MS m/z: 576 [M+Na]+

Example 3 (1R,2R,3R,5R,6R)-2-Amino-6-fluoro-3-[(4-fluorophenyl)methoxy]-2-({(1R)-1-[(tricyclo[3.3.1.1$^{3,7}$]decane-1-carbonyl)oxy]ethoxy}carbonyl)bicyclo[3.1.0]hexane-6-carboxylic Acid

[Formula 31]

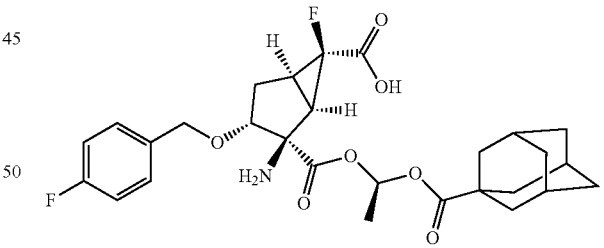

The title compound (0.093 g) was obtained (colorless solid) by the same procedure as in Example 1-(3) using the compound (0.20 g, 0.44 mmol) obtained in Example 1-(2) and (1S)-1-chloroethyl tricyclo[3.3.1.1$^{3,7}$]decane-1-carboxylate (see WO2013/180271) (0.32 g, 1.33 mmol).

1H NMR (600 MHz, DMSO-d6) δ ppm 1.40-1.45 (3H, m), 1.55 (3H, br d, J=11.6 Hz), 1.63 (3H, br d, J=12.0 Hz), 1.68-1.80 (6H, m), 1.86-1.91 (3H, m), 2.00-2.05 (1H, m), 2.12 (1H, dd, J=7.8, 2.5 Hz), 2.19-2.25 (1H, m), 2.27-2.33 (1H, m), 2.51-2.53 (1H, m), 3.71-3.76 (1H, m), 4.43-4.51 (1H, m), 4.54 (1H, d, J=12.0 Hz), 6.86 (1H, q, J=5.4 Hz), 7.12-7.17 (2H, m), 7.29-7.33 (2H, m)

MS m/z: 532 [M–H]–

Example 4 (1R,2R,3R,5R,6R)-2-Amino-6-fluoro-3-[(4-fluorophenyl)methoxy]-2-({(1S)-1-[(tricyclo[3.3.1.1³,⁷]decane-1-carbonyl)oxy]ethoxy}carbonyl)bicyclo[3.1.0]hexane-6-carboxylic Acid

[Formula 32]

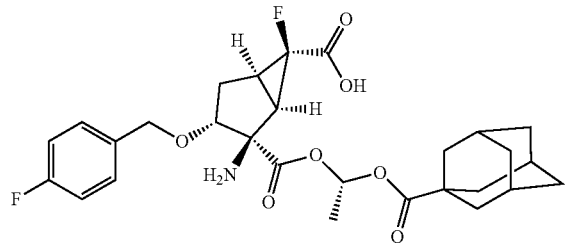

The title compound (0.153 g) was obtained (colorless solid) by the same procedure as in Example 1-(3) using the compound (0.20 g, 0.44 mmol) obtained in Example 1-(2) and (1R)-1-chloroethyl tricyclo[3.3.1.1³,⁷]decane-1-carboxylate (see WO2013/180271) (0.32 g, 1.33 mmol). The absolute configuration of the resulting compound (Example 4) was determined by X-ray structural analysis.

1H NMR (600 MHz, DMSO-d6) δ ppm 1.40 (3H, d, J=5.4 Hz), 1.57-1.71 (6H, m), 1.74-1.80 (6H, m), 1.88-2.00 (5H, m), 2.18-2.26 (1H, m), 2.29-2.38 (1H, m), 2.40-2.48 (1H, m), 3.70-3.77 (1H, m), 4.45 (1H, d, J=11.6 Hz), 4.56 (1H, d, J=11.6 Hz), 6.76 (1H, q, J=5.4 Hz), 7.13-7.18 (2H, m), 7.27-7.32 (2H, m)

MS m/z: 532 [M−H]−

Example 5 (1R,2R,3R,5R,6R)-2-Amino-2-[(1-{[(cyclohexyloxy)carbonyl]oxy}ethoxy)carbonyl]-6-fluoro-3-[(4-fluorophenyl)methoxy]bicyclo[3.1.0]hexane-6-carboxylic Acid

[Formula 33]

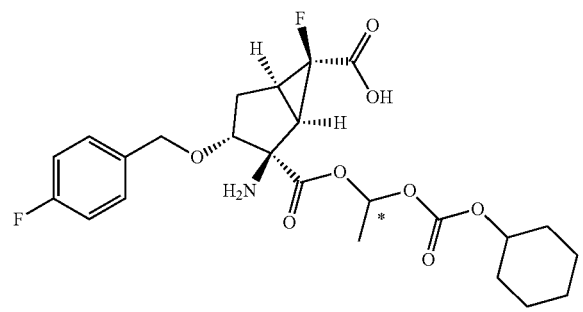

The title compound (0.023 g) was obtained (colorless solid) by the same procedure as in Example 1-(3) using the compound (0.30 g, 0.66 mmol) obtained in Example 1-(2) and 1-chloroethyl cyclohexyl carbonate (0.24 mL, 1.33 mmol).

1H NMR (600 MHz, DMSO-d6) δ ppm 1.14-1.47 (10H, m), 1.56-1.66 (2H, m), 1.70-1.76 (1H, m), 1.78-1.84 (1H, m), 1.98-2.04 (1H, m), 2.09-2.13 (1H, m), 2.16-2.23 (1H, m), 2.26-2.33 (1H, m), 3.70-3.74 (1H, m), 4.42-4.58 (3H, m), 6.73 (1H, q, J=5.4 Hz), 7.10-7.15 (2H, m), 7.28-7.32 (2H, m)

MS m/z: 520 [M+Na]+

Example 6 (1R,2R,3R,5R,6R)-2-Amino-6-fluoro-3-[(4-fluorophenyl)methoxy]-2-{([(L-valyloxy)methoxy]carbonyl}bicyclo[3.1.0]hexane-6-carboxylic Acid Dihydrochloride

[Formula 34]

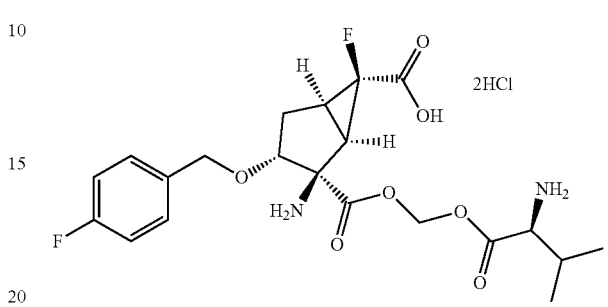

A colorless amorphous (0.091 g) was obtained by the same procedure as in Example 1-(3) using the compound (0.15 g, 0.34 mmol) obtained in Example 1-(2) and chloromethyl N-(tert-butoxycarbonyl)-L-valinate (0.27 g, 1.03 mmol). This amorphous was dissolved in CHCl₃ (1.2 mL). To the solution, a 4 M solution of HCl in dioxane (0.12 mL) was added dropwise at room temperature, and the mixture was stirred for 4 hours. The resulting solid was collected by filtration to obtain the title compound (40 mg) (pale yellow solid).

1H NMR (600 MHz, MeOH-d4) δ ppm 1.01 (6H, d, J=7.0 Hz), 2.20-2.27 (1H, m), 2.42-2.53 (3H, m), 2.58-2.64 (1H, m), 3.69 (1H, d, J=4.5 Hz), 4.16-4.20 (1H, m), 4.56 (2H, s), 6.01 (1H, d, J=6.2 Hz), 6.13 (1H, d, J=5.8 Hz), 7.09-7.14 (2H, m), 7.35-7.39 (2H, m), 7.91 (1H, s)

MS m/z: 457 [M+H]+

Example 7 (1R,2R,3R,5R,6R)-2-Amino-6-fluoro-3-[(4-fluorophenyl)methoxy]-2-({[[(tricyclo[3.3.1.1³,⁷]decane-1-carbonyl)oxy]methoxy}carbonyl)bicyclo[3.1.0]hexane-6-carboxylic Acid

[Formula 35]

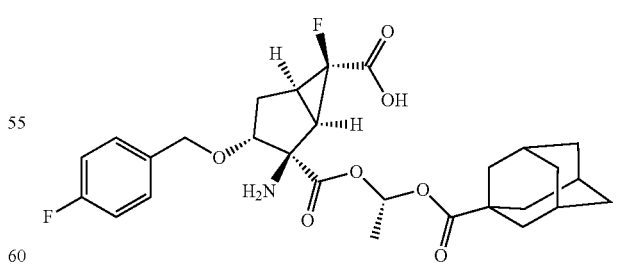

The title compound (52 mg) was obtained (colorless solid) by the same procedure as in Example 1-(3) using the compound (0.1 g, 0.22 mmol) obtained in Example 1-(2) and chloromethyl tricyclo[3.3.1.1³,⁷]decane-1-carboxylate (0.055 g, 0.24 mmol).

1H NMR (600 MHz, DMSO-d6) δ ppm 1.51-1.55 (3H, m), 1.59-1.64 (3H, m), 1.68-1.73 (6H, m), 1.87 (3H, br s), 1.95-2.00 (1H, m), 2.09 (1H, dd, J=7.6, 2.7 Hz), 2.13-2.19 (1H, m), 2.29 (1H, dd, J=13.2, 7.4 Hz), 2.47 (1H, br d, J=8.7 Hz), 2.52-2.57 (1H, m), 3.70-3.75 (1H, m), 4.46 (1H, d, J=12.0 Hz), 4.57 (1H, d, J=12.0 Hz), 5.75 (1H, d, J=5.8 Hz), 5.83 (1H, d, J=5.8 Hz), 7.15 (2H, t, J=8.4 Hz), 7.30 (2H, t, J=6.7 Hz)

MS m/z: 520 [M+H]+

Example 8 Synthesis of (1R,2R,3R,5R,6R)-2-amino-3-[(3,4-difluorophenyl)methoxy]-6-fluoro-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid

[Formula 36]

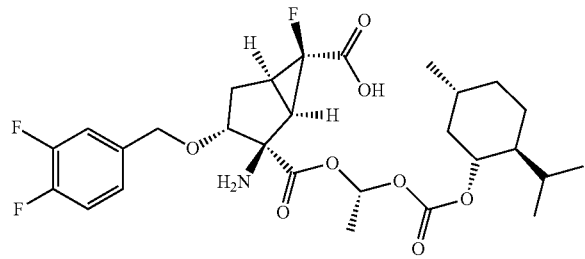

(1) (1R,2R,3R,5R,6R)-3-[(3,4-Difluorophenyl)methoxy]-6-fluoro-2-({[(prop-2-en-1-yl)oxy]carbonyl}amino)bicyclo[3.1.0]hexane-2,6-dicarboxylic Acid

[Formula 37]

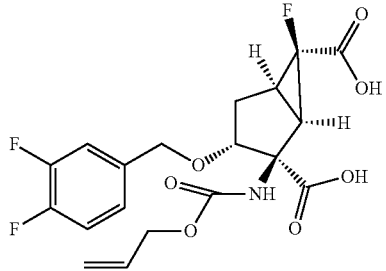

The title compound (1.7 g) was obtained (pale yellow amorphous) from Compound (II)-2 (1.5 g, 3.97 mmol) (see WO03/061698) by the same procedure as in Example 1-(1).

1H NMR (600 MHz, DMSO-d6) δ ppm 2.06-2.12 (1H, m), 2.15-2.23 (1H, m), 2.37 (1H, dd, J=13.6, 7.4 Hz), 2.69-2.73 (1H, m), 3.32 (2H, br s), 4.00-4.10 (1H, m), 4.38-4.53 (3H, m), 4.57-4.63 (1H, m), 5.15-5.24 (1H, m), 5.27-5.36 (1H, m), 5.82-5.96 (1H, m), 7.09-7.16 (1H, m), 7.29-7.42 (2H, m), 8.16 (1H, s)

MS m/z: 452 [M+Na]+

(2) (1R,2R,3R,5R,6R)-3-[(3,4-Difluorophenyl)methoxy]-6-fluoro-6-{[(prop-2-en-1-yl)oxy]carbonyl}-2-({[(prop-2-en-1-yl)oxy]carbonyl}amino)bicyclo[3.1.0]hexane-2-carboxylic Acid

[Formula 38]

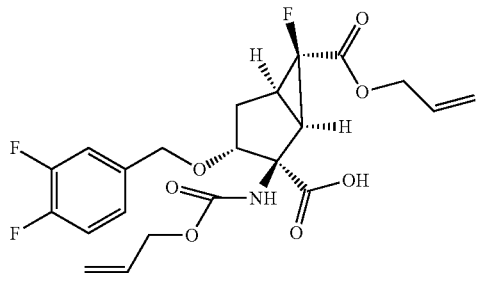

The title compound (1.8 g) was obtained (brown amorphous) by the same procedure as in Example 1-(2) using the compound (1.7 g, 3.96 mmol) obtained in Step (1) as a starting material.

1H NMR (600 MHz, DMSO-d6) δ ppm 2.14-2.45 (3H, m), 2.77 (1H, br d, J=7.0 Hz), 4.06-4.20 (1H, m), 4.39-4.72 (7H, m), 5.14-5.36 (4H, m), 5.84-5.97 (2H, m), 7.01-7.45 (3H, m), 8.20 (1H, br s)

MS m/z: 492 [M+Na]+

(3) (1R,2R,3R,5R,6R)-2-Amino-3-[(3,4-difluorophenyl)methoxy]-6-fluoro-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid (Example 8)

[Formula 39]

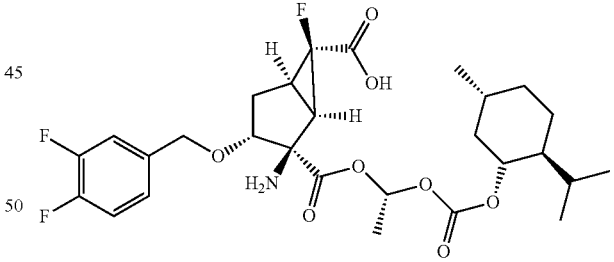

The title compound (135 mg) was obtained (colorless solid) by the same procedure as in Example 1-(3) using the compound (0.30 g, 0.64 mmol) obtained in Step (2) and (1R)-1-chloroethyl (1R,2S,5R)-5-methyl-2-(propan-2-yl)cyclohexyl carbonate (0.40 g, 1.53 mmol).

1H NMR (600 MHz, DMSO-d6) δ ppm 0.73 (3H, d, J=7.0 Hz), 0.78-0.89 (7H, m), 0.92-1.06 (2H, m), 1.30-1.47 (5H, m), 1.59-1.64 (2H, m), 1.79-1.86 (1H, m), 1.88-1.93 (1H, m), 1.98-2.05 (2H, m), 2.22-2.27 (1H, m), 2.35 (1H, dd, J=13.4, 7.6 Hz), 2.51-2.53 (1H, m), 3.72-3.78 (1H, m), 4.39-4.63 (3H, m), 6.67 (1H, q, J=5.4 Hz), 7.09-7.12 (1H, m), 7.27-7.31 (1H, m), 7.39 (1H, dt, J=10.7, 8.5 Hz)

MS m/z: 594 [M+Na]+

Example 9 (1R,2R,3R,5R,6R)-2-Amino-3-[(3,4-difluorophenyl)methoxy]-6-fluoro-2-({(1S)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid

[Formula 40]

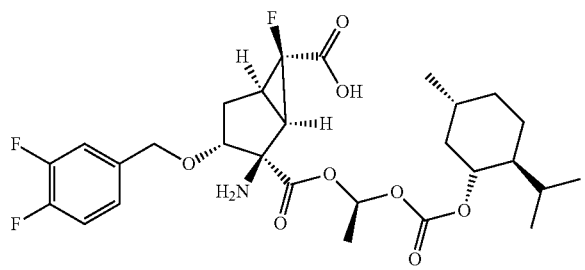

The title compound (19 mg) was obtained (colorless solid) by the same procedure as in Example 1-(3) using the compound (0.30 g, 0.64 mmol) obtained in Example 8-(2) and (1S)-1-chloroethyl (1R,2S,5R)-5-methyl-2-(propan-2-yl)cyclohexyl carbonate (0.40 g, 1.53 mmol).

1H NMR (600 MHz, DMSO-d6) δ ppm 0.66 (3H, d, J=6.6 Hz), 0.73-0.90 (7H, m), 0.94-1.03 (2H, m), 1.21-1.34 (2H, m), 1.38-1.53 (4H, m), 1.53-1.66 (2H, m), 1.69-1.81 (1H, m), 1.91-2.03 (2H, m), 2.10-2.24 (2H, m), 2.27-2.34 (1H, m), 3.70-3.74 (1H, m), 4.36-4.49 (2H, m), 4.53-4.59 (1H, m), 6.68 (1H, q, J=5.0 Hz), 7.11 (1H, br s), 7.30-7.38 (2H, m)

MS m/z: 594 [M+Na]+

Example 10 (1R,2R,3R,5R,6R)-2-Amino-3-[(3,4-difluorophenyl)methoxy]-6-fluoro-2-({(1R)-1-[(tricyclo[3.3.1.1³,⁷]decane-1-carbonyl)oxy]ethoxy}carbonyl)bicyclo[3.1.0]hexane-6-carboxylic Acid

[Formula 41]

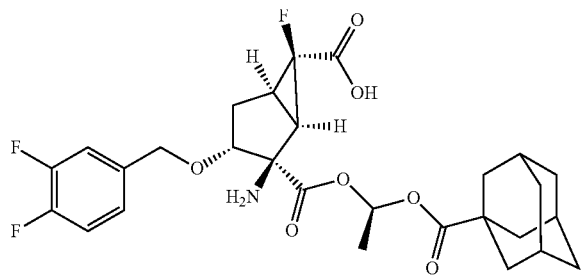

The title compound (149 mg) was obtained (colorless solid) by the same procedure as in Example 1-(3) using the compound (0.20 g, 0.42 mmol) obtained in Example 8-(2) and (1S)-1-chloroethyl tricyclo[3.3.1.1$^{3,7}$]decane-1-carboxylate (0.31 g, 1.28 mmol).

1H NMR (600 MHz, MeOH-d4) δ ppm 1.55 (3H, d, J=5.4 Hz), 1.64 (3H, br d, J=12.0 Hz), 1.74 (3H, br d, J=12.0 Hz), 1.77-1.82 (6H, m), 1.89-1.95 (3H, m), 2.24-2.32 (2H, m), 2.39-2.44 (1H, m), 2.50 (1H, dd, J=13.2, 7.4 Hz), 4.05-4.09 (1H, m), 4.52 (2H, s), 7.01-7.04 (1H, m), 7.11-7.15 (1H, m), 7.19-7.25 (1H, m), 7.28-7.33 (1H, m)

MS m/z: 550 [M−H]−

Example 11 (1R,2R,3R,5R,6R)-2-Amino-3-[(3,4-difluorophenyl)methoxy]-6-fluoro-2-({(1S)-1-[(tricyclo[3.3.1.1³,⁷]decane-1-carbonyl)oxy]ethoxy}carbonyl)bicyclo[3.1.0]hexane-6-carboxylic Acid

[Formula 42]

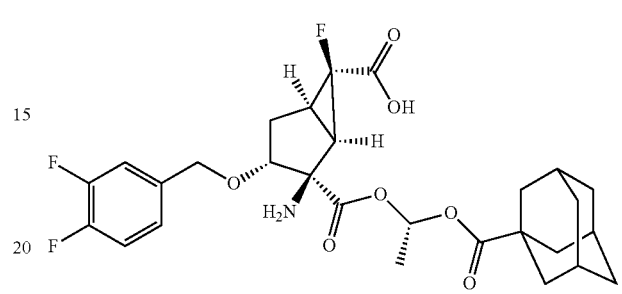

The title compound (123 mg) was obtained (colorless solid) by the same procedure as in Example 1-(3) using the compound (0.20 g, 0.42 mmol) obtained in Example 8-(2) and (1R)-1-chloroethyl tricyclo[3.3.1.1$^{3,7}$]decane-1-carboxylate (0.31 g, 1.28 mmol).

1H NMR (600 MHz, MeOH-d4) δ ppm 1.48 (3H, d, J=5.8 Hz), 1.70-1.80 (6H, m), 1.90 (6H, br s), 2.00 (3H, br s), 2.18-2.21 (1H, m), 2.25-2.29 (1H, m), 2.42-2.48 (1H, m), 2.52-2.58 (1H, m), 4.06-4.11 (1H, m), 4.49-4.56 (2H, m), 6.92 (1H, d, J=7.8 Hz), 7.10-7.14 (1H, m), 7.21-7.28 (2H, m)

MS m/z: 550 [M−H]−

Example 12 (1R,2R,3R,5R,6R)-2-Amino-3-[(3,4-difluorophenyl)methoxy]-6-fluoro-2-({[(tricyclo[3.3.1.1³,⁷]decane-1-carbonyl)oxy]methoxy}carbonyl)bicyclo[3.1.0]hexane-6-carboxylic Acid

[Formula 43]

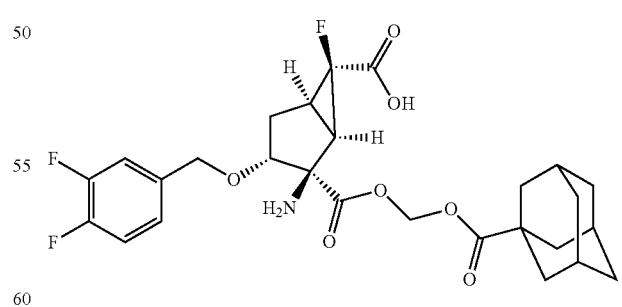

The title compound (61 mg) was obtained (colorless amorphous) by the same procedure as in Example 1-(3) using the compound (0.20 g, 0.42 mmol) obtained in Example 8-(2) and chloromethyl tricyclo[3.3.1.1$^{3,7}$]decane-1-carboxylate (0.19 g, 0.85 mmol).

1H NMR (600 MHz, DMSO-d6) δ ppm 1.50 (3H, br d, J=11.1 Hz), 1.60 (3H, br d, J=12.0 Hz), 1.66-1.69 (6H, m), 1.84 (3H, br s), 1.94-1.99 (1H, m), 2.05-2.12 (1H, m), 2.12-2.17 (1H, m), 2.30 (1H, dd, J=13.6, 7.4 Hz), 3.68-3.74 (1H, m), 4.45 (1H, d, J=12.0 Hz), 4.56 (1H, d, J=12.0 Hz), 5.73 (1H, d, J=5.8 Hz), 5.84 (1H, d, J=5.8 Hz), 7.08-7.11 (1H, m), 7.26-7.31 (1H, m), 7.34-7.41 (1H, m)

MS m/z: 538 [M+H]+

Example 13 Synthesis of (1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic Acid

[Formula 44]

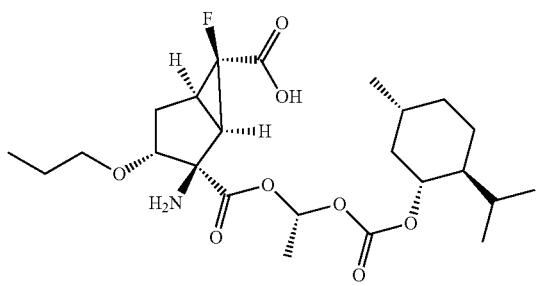

(1) (1R,2R,3R,5R,6R)-6-Fluoro-2-({[(prop-2-en-1-yl)oxy]carbonyl}amino)-3-propoxybicyclo[3.1.0]hexane-2,6-dicarboxylic Acid

[Formula 45]

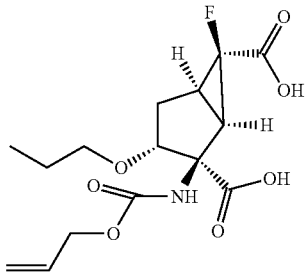

The title compound (3.4 g) was obtained (pale yellow amorphous) by the same procedure as in Example 1-(1) using Compound (II)-3 (3.0 g, 11.48 mmol) (see WO03/061698) as a starting material.

1H NMR (600 MHz, DMSO-d6) δ ppm 0.80 (3H, t, J=7.4 Hz), 1.40 (2H, sxt, J=7.0 Hz), 2.02-2.07 (1H, m), 2.07-2.15 (1H, m), 2.32 (1H, dd, J=14.0, 9.1 Hz), 2.63-2.70 (1H, m), 3.26-3.37 (2H, m), 3.47-3.55 (1H, m), 3.86-3.93 (1H, m), 4.46 (1H, br d, J=4.5 Hz), 5.18 (1H, d, J=9.9 Hz), 5.31 (1H, d, J=16.9 Hz), 5.86-5.95 (1H, m)

MS m/z: 368 [M+Na]+

(2) (1R,2R,3R,5R,6R)-6-Fluoro-6-{[(prop-2-en-1-yl)oxy]carbonyl}-2-({[(prop-2-en-1-yl)oxy]carbonyl}amino)-3-propoxybicyclo[3.1.0]hexane-2-carboxylic Acid

[Formula 46]

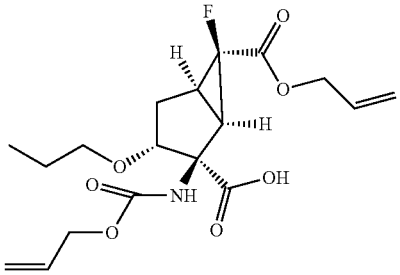

The title compound (1.8 g) was obtained by the same procedure as in Example 1-(2) using the compound (1.7 g, 4.95 mmol) obtained in Step (1) as a starting material.

1H NMR (600 MHz, DMSO-d6) δ ppm 0.80 (3H, t, J=7.4 Hz), 1.40 (2H, sxt, J=7.4 Hz), 2.08-2.27 (2H, m), 2.32-2.42 (1H, m), 2.70-2.86 (1H, m), 3.33-3.36 (2H, m), 3.39-3.55 (1H, m), 3.86-4.04 (1H, m), 4.36-4.75 (4H, m), 5.08-5.39 (4H, m), 5.82-5.97 (2H, m)

MS m/z: 408 [M+Na]+

(3) (1R,2R,3R,5R,6R)-2-Amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic Acid (Example 13)

[Formula 47]

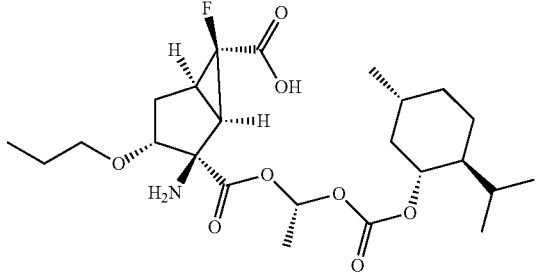

The title compound (46 mg) was obtained (colorless solid) by the same procedure as in Example 1-(3) using the compound (0.30 g, 0.78 mmol) obtained in Step (2) and (1R)-1-chloroethyl (1R,2S,5R)-5-methyl-2-(propan-2-yl)cyclohexyl carbonate (0.49 g, 1.87 mmol).

1H NMR (600 MHz, DMSO-d6) δ ppm 0.74 (3H, d, J=7.0 Hz), 0.78-0.89 (10H, m), 0.95-1.07 (2H, m), 1.32-1.48 (7H, m), 1.59-1.64 (2H, m), 1.80-1.86 (1H, m), 1.90-2.00 (3H, m), 2.15-2.20 (1H, m), 2.33 (1H, dd, J=13.2, 7.4 Hz), 3.30 (1H, dt, J=9.1, 6.6 Hz), 3.43 (1H, dt, J=9.1, 6.6 Hz), 3.56-3.64 (1H, m), 4.41-4.47 (1H, m), 6.65-6.68 (1H, m)

MS m/z: 488 [M+H]+

Example 14 (1R,2R,3R,5R,6R)-2-Amino-6-fluoro-2-({(1S)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic Acid

[Formula 48]

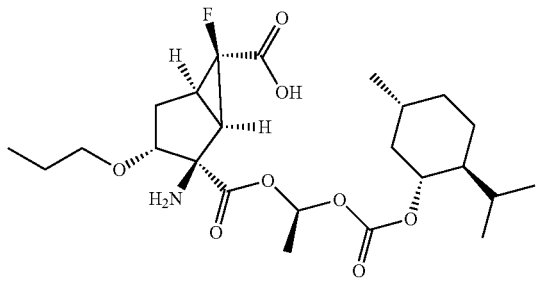

The title compound (100 mg) was obtained (colorless solid) by the same procedure as in Example 1-(3) using the compound (0.30 g, 0.78 mmol) obtained in Example 13-(2) and (1S)-1-chloroethyl (1R,2S,5R)-5-methyl-2-(propan-2-yl)cyclohexyl carbonate (0.49 g, 1.87 mmol).

1H NMR (600 MHz, DMSO-d6) δ ppm 0.75 (3H, d, J=7.0 Hz), 0.77-0.91 (10H, m), 0.98-1.09 (2H, m), 1.32-1.52 (7H, m), 1.60-1.66 (2H, m), 1.82-1.88 (1H, m), 1.94-2.00 (2H, m), 2.08 (1H, dd, J=8.0, 2.5 Hz), 2.13 (1H, ddd, J=13.2, 8.0, 5.8 Hz), 2.29 (1H, dd, J=13.2, 7.4 Hz), 3.28 (1H, dt, J=9.1, 6.6 Hz), 3.43 (1H, dt, J=9.1, 6.6 Hz), 3.56-3.62 (1H, m), 4.46 (1H, td, J=10.8, 4.3 Hz), 6.67 (1H, q, J=5.4 Hz)

MS m/z: 488 [M+H]+

Example 15 Synthesis of (1R,2R,3R,5R,6R)-2-amino-6-fluoro-2-({1-[({[(1S,2R,5S)-5-methyl-2-(propan-2-yl)cyclohexyl]oxy}carbonyl)oxy]ethoxy}carbonyl)-3-propoxybicyclo[3.1.0]hexane-6-carboxylic Acid

[Formula 49]

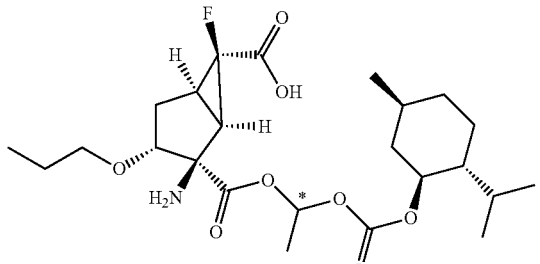

(1) 1-Chloroethyl (1S,2R,5S)-5-methyl-2-(propan-2-yl)cyclohexyl carbonate

[Formula 50]

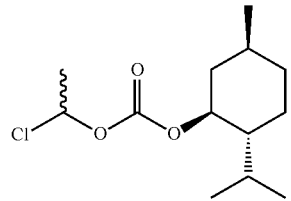

A solution of D-menthol (5.0 g, 31.99 mmol) and pyridine (2.6 mL, 31.99 mmol) in CHCl$_3$ (36 mL) was cooled to −60° C. in an acetone-dry ice bath, and 1-chloroethyl carbonochloridate (3.67 mL, 33.59 mmol) was added dropwise over 10 minutes. The mixture was stirred at −60° C. for 30 minutes and then transferred to an ice bath. The temperature was raised to 0° C., and water was added. The organic layer was separated, then washed with brine, and dried over MgSO$_4$. The insoluble was filtered, the filtrate was concentrated under reduced pressure. The resulting residue was purified by silica gel column chromatography (Grace 12 g, n-Hexane/EtOAc=100/0 to 90/10) to obtain the title compound (7.7 g) (colorless oil).

1H NMR (600 MHz, CHLOROFORM-d) δ ppm 0.81 (3H, dd, J=10.3, 7.0 Hz), 0.85-0.95 (7H, m), 1.03-1.13 (2H, m), 1.39-1.54 (2H, m), 1.66-1.74 (2H, m), 1.84 (3H, dd, J=5.8, 2.1 Hz), 1.91-1.99 (1H, m), 2.06-2.15 (1H, m), 4.60 (1H, qd, J=10.7, 4.3 Hz), 6.44 (1H, qd, J=5.8, 1.7 Hz)

(2) 2-{1-[({[(1S,2R,5S)-5-Methyl-2-(propan-2-yl)cyclohexyl]oxy}carbonyl)oxy]ethyl}6-prop-2-en-1-yl (1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 51]

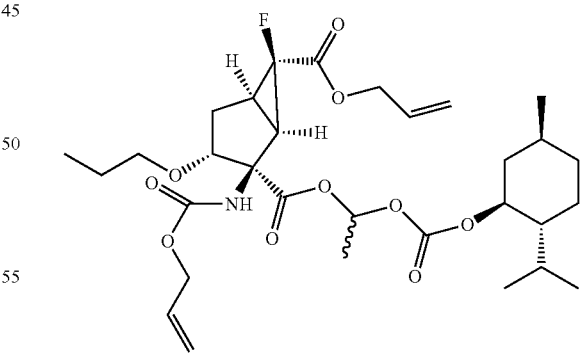

To a solution of the compound (0.56 g, 1.47 mmol) obtained in Example 13-(2) in DMF (7 mL), the compound (0.77 g, 2.94 mmol) obtained in Step (1), K$_2$CO$_3$ (0.30 g, 2.20 mmol) and NaI (0.44 g, 2.94 mmol) were added, and the mixture was stirred at 50° C. for 3.5 hours. The reaction solution was cooled to room temperature and then separated by the addition of water. The aqueous layer was extracted with EtOAc. Then, the organic layers were combined and washed with 5% brine and brine. After drying over MgSO$_4$, the insoluble was filtered, the filtrate was concentrated under reduced pressure. The resulting residue was purified by silica gel column chromatography (Grace 12 g, n-Hexane/EtOAc=100/0 to 60/40) to obtain the title compound (0.40 g) as a diastereomer mixture (colorless oil).

1H NMR (600 MHz, CHLOROFORM-d) δ ppm 0.77-0.95 (15H, m), 1.50-1.58 (7H, m), 1.66-1.71 (2H, m), 1.93-2.02 (1H, m), 2.08-2.16 (1H, m), 2.20-2.27 (1H, m), 2.31-2.38 (1H, m), 2.40-2.48 (1H, m), 2.90-3.03 (1H, m), 3.29-3.34 (1H, m), 3.46-3.53 (1H, m), 3.73-3.78 (1H, m), 4.53-4.71 (5H, m), 5.20-5.35 (5H, m), 5.87-5.95 (2H, m), 6.81-6.94 (1H, m)

(3) Resolution of 2-{1-[({[(1S,2R,5S)-5-methyl-2-(propan-2-yl)cyclohexyl]oxy}carbonyl)oxy]ethyl}6-prop-2-en-1-yl (1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 52]

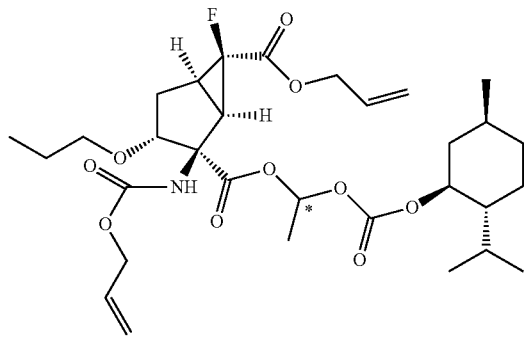

The compound obtained in Example 15(2) was separated by chiral column chromatography (CHIRALPAK ID, n-Hexane/IPA=7:3) to obtain a fraction of the 1st peak as the compound of Example 15(3)-A (0.14 g) and a fraction of the 2nd peak as the compound of Example 15(3)-B (0.20 g) (both were colorless oils).

Retention time: Example 15(3)-A; 3.22 min., Example 15(3)-B; 5.72 min. (CHIRAL PAK ID-3, n-Hexane/IPA=7:3)

(4) (1R,2R,3R,5R,6R)-2-Amino-6-fluoro-2-({1-[({[(1S,2R,5S)-5-methyl-2-(propan-2-yl)cyclohexyl]oxy}carbonyl)oxy]ethoxy}carbonyl)-3-propoxybicyclo[3.1.0]hexane-6-carboxylic Acid (Examples 15-A and 15-B)

To a solution of the compound of Example 15(3)-A (0.14 g, 0.23 mmol) in CHCl$_3$ (2.3 mL), 1,3-dimethylbarbituric acid (0.036 g, 0.23 mmol) and Pd(PPh$_3$)$_4$ (0.004 g, 0.0035 mmol) were added, and the mixture was stirred at room temperature for 20 minutes. The reaction solution was concentrated under reduced pressure. MeCN (5 mL) was added to the resulting residue, and the mixture was stirred at room temperature for 1.5 hours. The resulting crystals were collected by filtration to obtain the title compound of Example 15-A (0.090 g) (colorless solid). In the same was as above, the title compound of Example 15-B (0.13 g) was obtained (colorless solid) from Example 15(3)-B (0.20 g, 0.33 mmol).

Example 15-A

1H NMR (400 MHz, DMSO-d6) δ ppm 0.74-0.91 (13H, m), 0.95-1.12 (2H, m), 1.33-1.51 (7H, m), 1.60-1.68 (2H, m), 1.79-1.90 (1H, m), 1.94-2.05 (2H, m), 2.06-2.19 (2H, m), 2.27-2.36 (1H, m), 3.29 (1H, dt, J=9.1, 6.7 Hz), 3.44 (3H, dt, J=9.1, 6.7 Hz), 3.56-3.66 (1H, m), 4.45 (1H, td, J=10.9, 4.4 Hz), 6.74 (1H, q, J=5.4 Hz)

MS m/z: 488 [M+H]+

Example 15-B

1H NMR (400 MHz, DMSO-d6) δ ppm 0.73 (3H, d, J=7.0 Hz), 0.76-0.91 (10H, m), 0.96-1.09 (2H, m), 1.30-1.50 (7H, m), 1.57-1.67 (2H, m), 1.72-1.82 (1H, m), 1.92-1.99 (3H, m), 2.12-2.23 (1H, m), 2.28-2.40 (1H, m), 3.30 (1H, dt, J=9.1, 6.5 Hz), 3.44 (1H, dt, J=9.1, 6.5 Hz), 3.56-3.62 (1H, m), 4.46 (1H, td, J=10.9, 4.3 Hz), 6.69 (1H, q, J=5.5 Hz)

MS m/z: 488 [M+H]+

Example 16 Synthesis of (1R,2R,3R,5R,6R)-2-amino-6-fluoro-3-[(4-fluorophenyl)methoxy]-2-({1-[({[(1S,2R,5S)-5-methyl-2-(propan-2-yl)cyclohexyl]oxy}carbonyl)oxy]ethoxy}carbonyl)bicyclo[3.1.0]hexane-6-carboxylic Acid

[Formula 53]

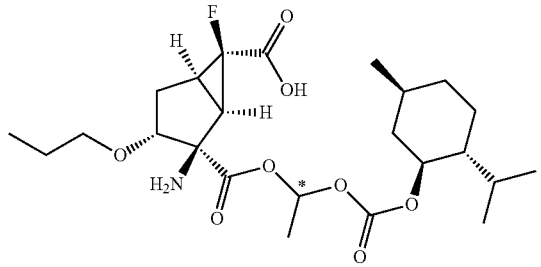

[Formula 54]

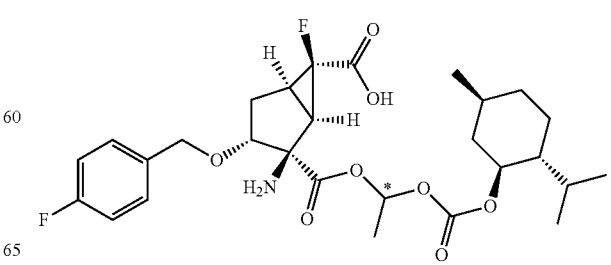

(1) 2-{1-[({[(1S,2R,5S)-5-Methyl-2-(propan-2-yl)cyclohexyl]oxy}carbonyl)oxy]ethyl} 6-prop-2-en-1-yl (1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 55]

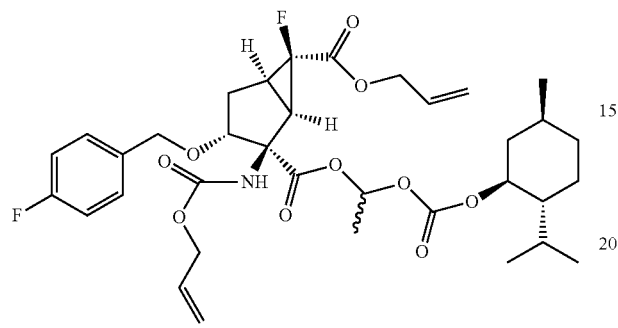

The title compound (0.41 g) was obtained as a diastereomer mixture (colorless oil) by the same procedure as in Example 15-(2) using the compound (0.41 g, 0.93 mmol) obtained in Example 1-(2) and the compound (0.48 g, 1.85 mmol) obtained in Example 15-(1) as starting materials.

1H NMR (600 MHz, CHLOROFORM-d) δ ppm 0.70-1.14 (12H, m), 1.19-1.71 (7H, m), 1.88-2.28 (2H, m), 2.34-2.46 (2H, m), 2.87-3.03 (1H, m), 3.39-3.45 (1H, m), 3.79-3.86 (1H, m), 4.44-4.72 (7H, m), 5.00-5.10 (1H, m), 5.20-5.36 (4H, m), 5.85-5.95 (2H, m), 6.84-6.95 (1H, m), 6.99-7.06 (2H, m), 7.25-7.27 (2H, m)

MS m/z: 700 [M+Na]+

(2) Resolution of 2-{1-[({[(1S,2R,5S)-5-methyl-2-(propan-2-yl)cyclohexyl]oxy}carbonyl)oxy]ethyl}6-prop-2-en-1-yl (1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 56]

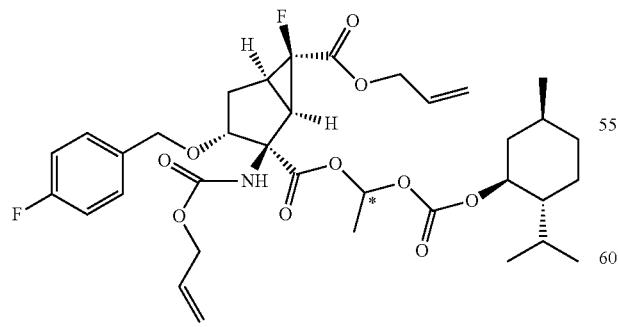

The compound obtained in Example 16(1) was separated by chiral column chromatography (CHIRALPAK ID, n-Hexane/EtOH=4:1) to obtain a fraction of the 1st peak as the compound of Example 16(2)-A (0.11 g) and a fraction of the 2nd peak as the compound of Example 16(2)-B (0.15 g) (both were colorless oils).

Retention time: Example 16(2)-A; 2.92 min., Example 16(2)-B; 4.30 min. (CHIRAL PAK ID-3, n-Hexane/EtOH=8:2)

(3) (1R,2R,3R,5R,6R)-2-Amino-6-fluoro-3-[(4-fluorophenyl)methoxy]-2-({1-[({[(1S,2R,5S)-5-methyl-2-(propan-2-yl)cyclohexyl]oxy}carbonyl)oxy]ethoxy}carbonyl)bicyclo[3.1.0]hexane-6-carboxylic Acid (Examples 16-A and 16-B)

[Formula 57]

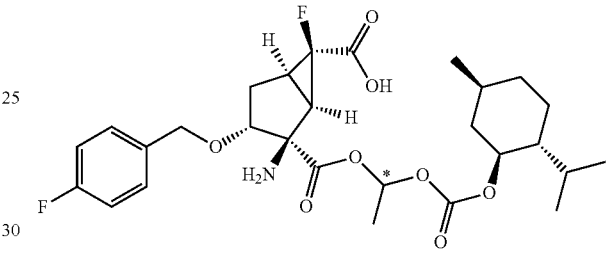

The title compounds of Example 16-A (0.058 g) and Example 16-B (0.076 g) were obtained (both were colorless solids) by the same procedure as in Example 15-(4) using the compounds of Example 16(2)-A (0.10 g, 0.15 mmol) and Example 16(2)-B (0.13 g, 0.20 mmol) obtained in Step (2) as starting materials, respectively.

Example 16-A

1H NMR (400 MHz, DMSO-d6) δ ppm 0.75 (3H, d, J=6.9 Hz), 0.78-1.10 (7H, m), 1.28-1.44 (2H, m), 1.47 (3H, d, J=5.5 Hz) 1.58-1.67 (2H, m), 1.78-1.90 (2H, m), 2.00-2.07 (2H, m), 2.14 (1H, dd, J=7.8, 2.8 Hz), 2.18-2.26 (1H, m), 2.32 (1H, dd, J=13.3, 7.4 Hz), 3.71-3.79 (1H, m), 4.37-4.50 (2H, m), 4.58 (1H, d, J=12 Hz), 6.75 (1H, q, J=5.5 Hz), 7.09-7.16 (2H, m), 7.29-7.36 (2H, m)

MS m/z: 554 [M+H]+

Example 16-B

1H NMR (400 MHz, DMSO-d6) δ ppm 0.72 (3H, d, J=7.0 Hz), 0.80-0.92 (7H, m), 0.97-1.10 (2H, m), 1.29-1.52 (4H, m), 1.56-1.68 (2H, m), 1.71-1.82 (1H, m), 1.92-2.02 (3H, m), 2.19-2.40 (2H, m), 3.68-3.77 (1H, m), 4.41-4.51 (2H, m), 4.56 (1H, d, J=12.0 Hz), 6.70 (1H, q, J=5.4 Hz), 7.11-7.20 (2H, m), 7.27-7.34 (2H, m)

MS m/z: 554 [M+H]+

Example 17 Synthesis of (1R,2R,3R,5R,6R)-2-amino-6-fluoro-3-[(4-fluorophenyl)methoxy]-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic Acid

[Formula 58]

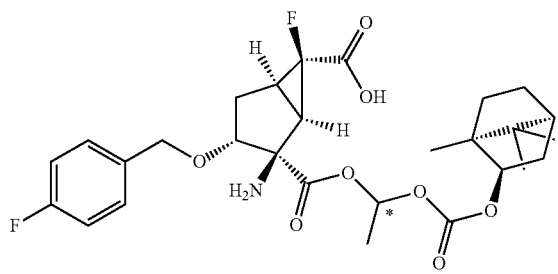

(1) 1-Chloroethyl (1S,2R,4S)-1,7,7-trimethylbicyclo[2.2.1]heptan-2-yl carbonate

[Formula 59]

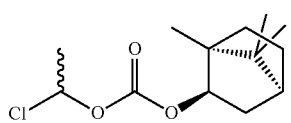

The title compound (8.2 g) was obtained (colorless oil) by the same procedure as in Example 15(1) using (−)-borneol (5.0 g, 32.41 mmol) as a starting material.

1H NMR (400 MHz, CHLOROFORM-d) δ ppm 0.87-0.93 (9H, m), 1.13 (1H, ddd, J=13.9, 12.4, 3.5 Hz), 1.23-1.38 (2H, m), 1.69-1.88 (5H, m), 1.89-1.99 (1H, m), 2.35-2.46 (1H, m), 4.85-4.92 (1H, m), 6.43 (1H, q, J=5.8 Hz)
MS m/z: 283 [M+Na]+

(2) 6-Prop-2-en-1-yl 2-{1-[({[(1S,2R,4S)-1,7,7-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 60]

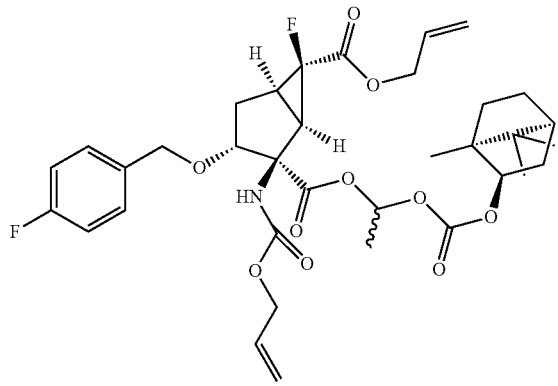

The title compound (0.41 g) was obtained as a diastereomer mixture (colorless oil) by the same procedure as in Example 15-(2) using the compound (0.40 g, 0.89 mmol) obtained in Example 1-(2) and the compound (0.46 g, 1.77 mmol) obtained in Example 17-(1) as starting materials.

1H NMR (400 MHz, CHLOROFORM-d) δ ppm 0.83-0.97 (9H, m), 1.01-1.14 (1H, m), 1.20-1.40 (2H, m), 1.52 (3H, d, J=5.4 Hz), 1.62-1.78 (2H, m), 1.86-1.96 (1H, m), 2.23-2.47 (5H, m), 2.94-3.05 (1H, m), 3.84 (1H, td, J=7.8, 4.8 Hz), 4.45-4.71 (6H, m), 4.75-4.91 (1H, m), 5.05 (1H, s), 5.19-5.37 (4H, m), 5.84-5.97 (2H, m), 6.88 (1H, q, J=5.5 Hz), 7.04 (2H, m), 7.26 (2H, m)

(3) Resolution of 6-prop-2-en-1-yl 2-{1-[({[(1S,2R,4S)-1,7,7-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 61]

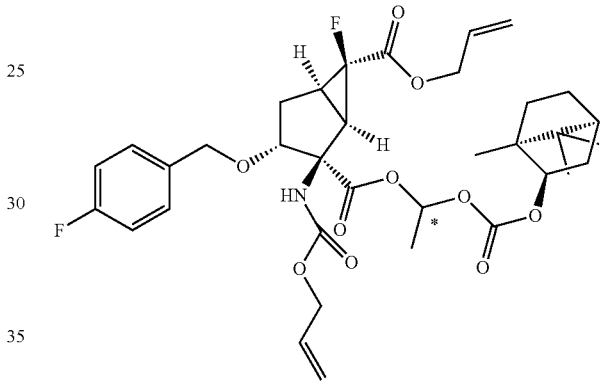

The compound (0.41 g, 0.93 mmol) obtained in Example 17(2) was separated by chiral column chromatography (CHIRALPAK IC, n-Hexane/IPA=6:4) to obtain a fraction of the 1st peak as the compound of Example 17(3)-A (0.20 g) and a fraction of the 2nd peak as the compound of Example 17(3)-B (0.15 g) (both were colorless oils).
Retention time: Example 17(3)-A; 4.57 min., Example 17(3)-B; 5.84 min. (CHIRAL PAK IC-3, n-Hexane/IPA=6:4)

(4) (1R,2R,3R,5R,6R)-2-Amino-6-fluoro-3-[(4-fluorophenyl)methoxy]-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic Acid (Examples 17-A and 17-B)

[Formula 62]

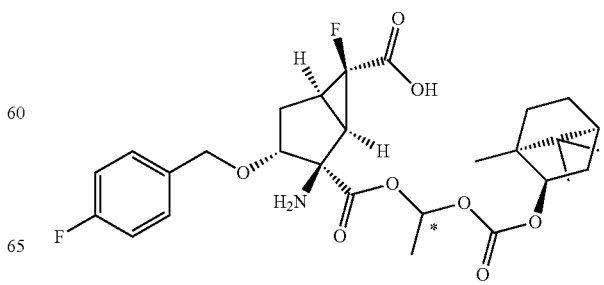

51

The title compounds of Example 17-A (0.098 g) and Example 17-B (0.072 g) were obtained (both were colorless solids) by the same procedure as in Example 15-(4) using the compounds of Example 17(3)-A (0.18 g, 0.27 mmol) and Example 17(3)-B (0.13 g, 0.20 mmol) obtained in Example 17(3) as starting materials, respectively.

Example 17-A

1H NMR (400 MHz, DMSO-d6) δ ppm 0.78-0.86 (9H, m), 0.97 (1H, dd, J=13.9, 3.4 Hz), 1.13-1.21 (1H, m), 1.23-1.32 (1H, m), 1.43 (3H, d, J=5.4 Hz), 1.63-1.81 (3H, m), 1.97-2.05 (2H, m), 2.20-2.37 (3H, m), 3.69-3.77 (1H, m), 4.45 (1H, d, J=11.6 Hz), 4.55 (1H, d, J=11.6 Hz), 4.70-4.75 (1H, m), 6.69 (1H, q, J=5.4 Hz), 7.12-7.18 (2H, m), 7.26-7.32 (2H, m)

MS m/z: 552 [M+H]+

Example 17-B

1H NMR (400 MHz, DMSO-d6) δ ppm 0.73 (3H, s), 0.82 (6H, s), 1.02 (1H, dd, J=13.8, 3.4 Hz), 1.11-1.30 (2H, m), 1.47 (3H, d, J=5.5 Hz), 1.62-1.78 (3H, m), 1.99-2.07 (1H, m), 2.10-2.34 (4H, m), 3.69-3.76 (1H, m), 4.46 (1H, d, J=12.2 Hz), 4.55 (1H, d, J=12.2 Hz), 4.64-4.72 (1H, m), 6.75 (1H, q, J=5.5 Hz), 7.08-7.16 (2H, m), 7.29-7.34 (2H, m)

MS m/z: 552 [M+H]+

Example 18 Synthesis of (1R,2R,3R,5R,6R)-2-amino-6-fluoro-3-propoxy-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic Acid

[Formula 63]

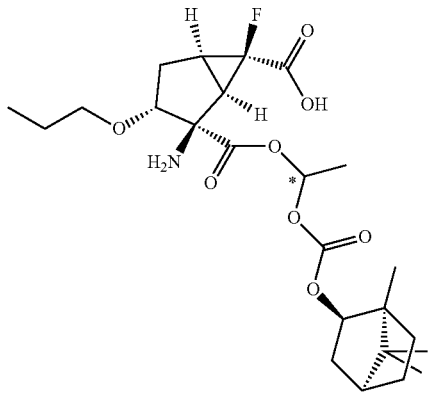

52

(1) 6-Prop-2-en-1-yl 2-{1-[({[(1S,2R,4S)-1,7,7-trimethylbicyclo[2.2.1]heptan-2-yl]oxy}carbonyl)oxy]ethyl}(1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 64]

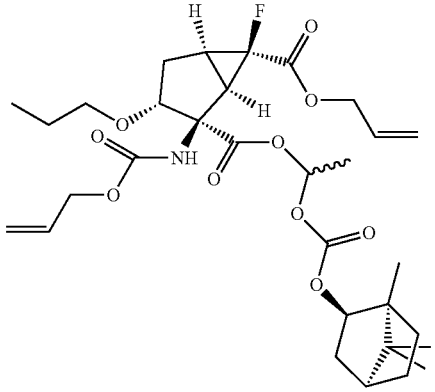

The title compound (0.44 g) was obtained as a diastereomer mixture (colorless oil) by the same procedure as in Example 15-(2) using the compound (0.40 g, 0.94 mmol) obtained in Example 13-(2) and the compound (0.49 g, 1.89 mmol) obtained in Example 17-(1) as starting materials.

1H NMR (400 MHz, CHLOROFORM-d) δ ppm 0.84-0.91 (12H, m), 1.07-1.14 (1H, m), 1.23-1.35 (2H, m), 1.49-1.59 (6H, m), 1.67-1.79 (2H, m), 1.89-1.97 (1H, m), 2.22-2.48 (4H, m), 2.96 (1H, br s), 3.27-3.34 (1H, m), 3.44-3.53 (1H, m), 3.72-3.79 (1H, m), 4.51-4.71 (4H, m), 4.82-4.87 (1H, m), 5.16-5.36 (4H, m), 5.84-5.96 (2H, m), 6.84-6.91 (1H, m)

MS m/z: 632 [M+Na]+

(2) Resolution of 6-prop-2-en-1-yl 2-{1-[({[(1S,2R,4S)-1,7,7-trimethylbicyclo[2.2.1]heptan-2-yl]oxy}carbonyl)oxy]ethyl} (1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 65]

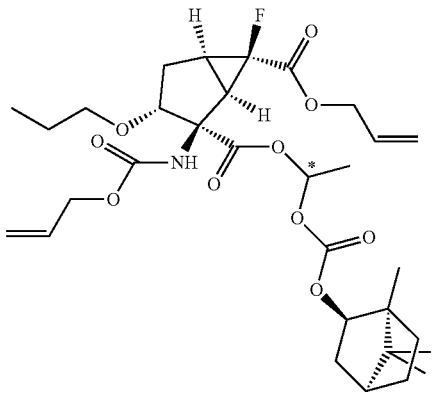

The compound obtained in Example 18(1) was separated by chiral column chromatography (CHIRALPAK IC, n-Hexane/IPA=40:60) to obtain a fraction of the 1st peak as the compound of Example 18(2)-A (0.17 g) and a fraction of the 2nd peak as the compound of Example 18(2)-B (0.12 g) (both were colorless oils).

Retention time: Example 18(2)-A; 3.42 min., Example 18(2)-B; 4.26 min. (CHIRAL PAK IC-3, n-Hexane/IPA=2:3)

(3) (1R,2R,3R,5R,6R)-2-Amino-6-fluoro-3-propoxy-2-({1-[({[(1S,2R,4S)-1,7,7-trimethylbicyclo[2.2.1]heptan-2-yl]oxy}carbonyl)oxy]ethoxy}carbonyl)bicyclo[3.1.0]hexane-6-carboxylic Acid (Examples 18-A and 18-B)

[Formula 66]

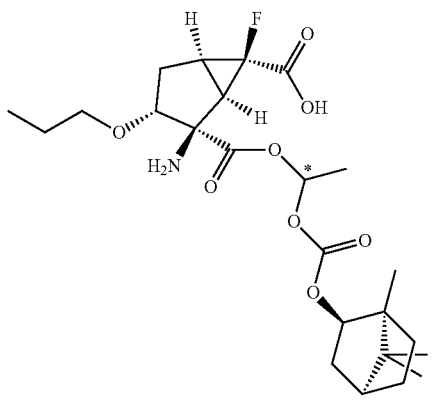

The title compounds of Example 18-A (0.089 g) and Example 18-B (0.064 g) were obtained (both were colorless solids) by the same procedure as in Example 15-(4) using the compounds of Example 18(2)-A (0.16 g, 0.27 mmol) and Example 18(2)-B (0.11 g, 0.19 mmol) obtained in Step (2) as starting materials, respectively.

Example 18-A

1H NMR (400 MHz, DMSO-d6) δ ppm 0.81 (3H, s), 0.84 (6H, d, J=3.7 Hz), 0.95 (1H, dd, J=13.8, 3.5 Hz), 1.10-1.19 (1H, m), 1.22-1.31 (1H, m), 1.47 (3H, d, J=5.4 Hz), 1.62-1.80 (3H, m), 2.02-2.08 (1H, m), 2.11-2.36 (4H, m), 3.70-3.77 (1H, m), 4.48 (1H, d, J=12.0 Hz), 4.56 (1H, d, J=12.0 Hz), 4.68-4.77 (1H, m), 6.74 (1H, q, J=5.4 Hz), 7.09-7.18 (2H, m), 7.29-7.36 (2H, m)

MS m/z: 486 [M+H]+

Example 18-B

1H NMR (400 MHz, DMSO-d6) δ ppm 0.77 (3H, s), 0.84 (6H, d, J=7.8 Hz), 1.03 (1H, dd, J=13.8, 3.4 Hz), 1.14-1.32 (2H, m), 1.42 (3H, d, J=5.3 Hz), 1.65-1.79 (3H, m), 1.96-2.05 (2H, m), 2.20-2.38 (3H, m), 3.69-3.78 (1H, m), 4.45 (1H, d, J=11.6 Hz), 4.55 (1H, d, J=11.6 Hz), 4.73-4.78 (1H, m), 6.69 (1H, q, J=5.3 Hz), 7.11-7.19 (2H, m), 7.26-7.33 (2H, m)

MS m/z: 486 [M+H]+

Example 19 (1R,2R,3R,5R,6R)-2-Amino-6-fluoro-3-[(4-fluorophenyl)methoxy]-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic Acid

[Formula 67]

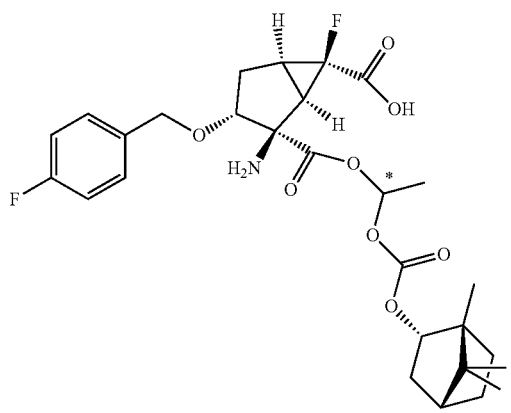

(1) 1-Chloroethyl (1R,2S,4R)-1,7,7-trimethylbicyclo[2.2.1]heptan-2-yl carbonate

[Formula 68]

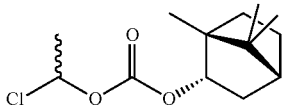

The title compound (4.2 g) was obtained (colorless oil) by the same procedure as in Example 15(1) using (+)-borneol (2.5 g, 16.21 mmol) as a starting material.

1H NMR (400 MHz, CHLOROFORM-d) δ ppm 0.87-0.93 (9H, m), 1.13 (1H, ddd, J=16.0, 12.4, 3.5 Hz), 1.23-1.38 (2H, m), 1.69-1.83 (2H, m), 1.83-1.88 (3H, m), 1.89-1.99 (1H, m), 2.35-2.46 (1H, m), 4.85-4.92 (1H, m), 6.41-6.47 (1H, m)

MS m/z: 283 [M+Na]+

(2) 6-Prop-2-en-1-yl 2-{1-[({[(1R,2S,4R)-1,7,7-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 69]

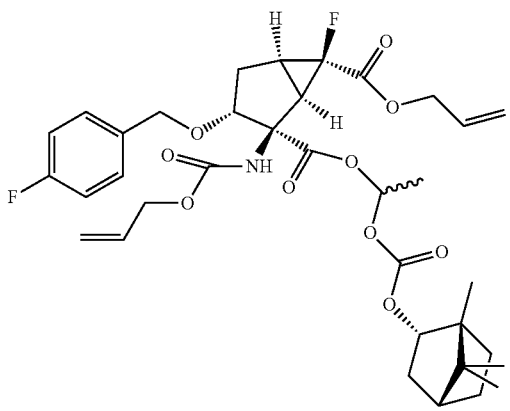

The title compound (0.34 g) was obtained as a diastereomer mixture (colorless oil) by the same procedure as in Example 15-(2) using the compound (0.40 g, 0.89 mmol) obtained in Example 1-(2) and the compound (0.46 g, 1.77 mmol) obtained in Example 19-(1) as starting materials.

1H NMR (400 MHz, CHLOROFORM-d) δ ppm 0.83-0.90 (9H, m), 1.05-1.13 (1H, m), 1.20-1.35 (2H, m), 1.47-1.55 (3H, m), 1.66-1.79 (2H, m), 1.87-1.96 (1H, m), 2.22-2.29 (1H, m), 2.30-2.46 (3H, m), 2.90-3.04 (1H, m), 3.81-3.88 (1H, m), 4.45-4.71 (6H, m), 4.80-4.87 (1H, m), 5.03-5.14 (1H, m), 5.15-5.36 (4H, m), 5.84-5.96 (2H, m), 6.89 (1H, q, J=5.4 Hz), 7.03 (2H, m), 7.23-7.30 (2H, m)
MS m/z: 698 [M+Na]+

(3) Resolution of 6-prop-2-en-1-yl 2-{1-[({[(1R,2S,4R)-1,7,7-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 70]

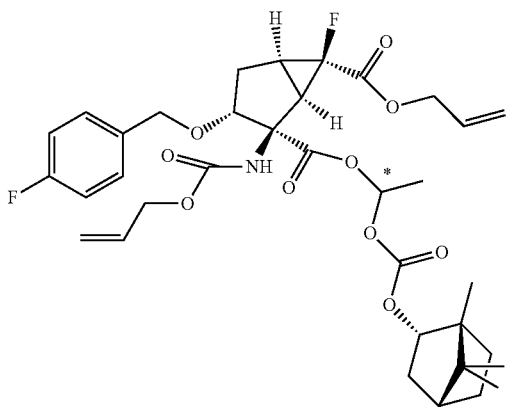

The compound (0.34 g, 0.50 mmol) obtained in Example 19(2) was separated by chiral column chromatography (CHIRALPAK ID, n-Hexane/EtOH=84:16) to obtain a fraction of the 1st peak as the compound of Example 19(3)-A (0.085 g, colorless oil) and a component containing a fraction of the 2nd peak. The component containing a fraction of the 2nd peak was further purified by chiral column chromatography (CHIRALPAK AS-H, n-Hexane/EtOH=80:20) to obtain the compound of Example 19(3)-B (0.098 g) (colorless oil).
Retention time: Example 19(3)-A; 3.51 min., Example 19(3)-B; 4.25 min. (CHIRAL PAK ID-3, n-Hexane/EtOH=4:1)

(4) (1R,2R,3R,5R,6R)-2-Amino-6-fluoro-3-[(4-fluorophenyl)methoxy]-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic Acid (Examples 19-A and 19-B)

[Formula 71]

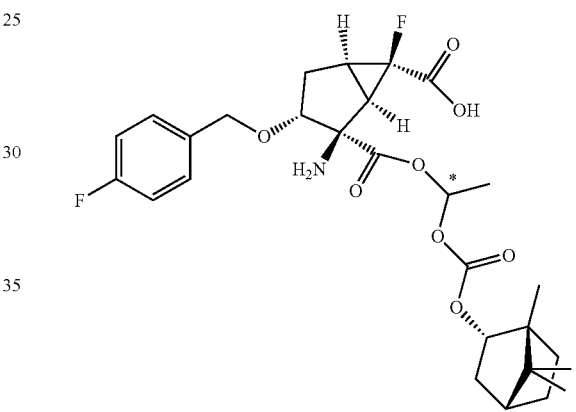

The title compounds of Example 19-A (0.044 g) and Example 19-B (0.056 g) were obtained (both were colorless solids) by the same procedure as in Example 15-(4) using the compounds of Example 19(3)-A (0.076 g, 0.11 mmol) and Example 19(3)-B (0.085 g, 0.13 mmol) obtained in Example 19(3) as starting materials, respectively.

Example 19-A

1H NMR (400 MHz, DMSO-d6) δ ppm 0.77-0.88 (12H, m), 0.98 (1H, dd, J=13.9, 3.4 Hz), 1.13-1.33 (2H, m), 1.40 (2H, sxt, 7.1 Hz), 1.49 (3H, d, 5.4 Hz), 1.63-1.83 (3H, m), 1.96-2.03 (2H, m), 2.15-2.23 (1H, m), 2.25-2.38 (3H, m), 3.26-3.33 (1H, m), 3.39-3.47 (1H, m), 3.54-3.64 (1H, m), 4.70-4.76 (1H, m), 6.66-6.71 (1H, m)
MS m/z: 552 [M+H]+

Example 19-B

1H NMR (400 MHz, DMSO-d6) δ ppm 0.76-0.90 (12H, m), 1.04 (1H, dd, J=13.7, 3.3 Hz), 1.16-1.32 (2H, m), 1.41 (2H, sxt, J=7.1 Hz), 1.50 (3H, d, J=5.4 Hz), 1.64-1.84 (3H, m), 1.97-2.06 (1H, m), 2.06-2.21 (2H, m), 2.25-2.36 (2H, m), 3.22-3.32 (1H, m), 3.39-3.47 (1H, m), 3.58-3.66 (1H, m), 4.71-4.78 (1H, m), 6.70-6.75 (1H, m)
MS m/z: 552 [M+H]+

Example 20 Synthesis of (1R,2R,3R,5R,6R)-2-amino-6-fluoro-3-propoxy-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic Acid

[Formula 72]

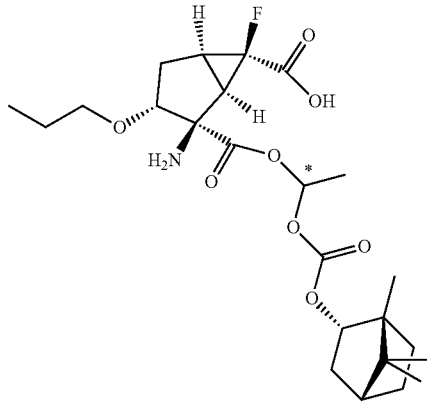

(1) 6-Prop-2-en-1-yl 2-{1-[({[(1R,2S,4R)-1,7,7-trimethylbicyclo[2.2.1]heptan-2-yl]oxy}carbonyl)oxy]ethyl}(1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 73]

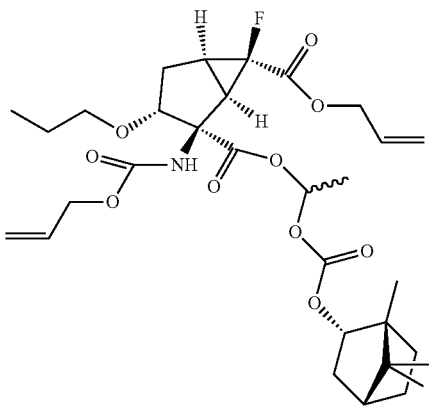

The title compound (0.24 g) was obtained as a diastereomer mixture (colorless amorphous) by the same procedure as in Example 15-(2) using the compound (0.40 g, 0.94 mmol) obtained in Example 13-(2) and the compound (0.49 g, 1.89 mmol) obtained in Example 19-(1) as starting materials.

1H NMR (400 MHz, CHLOROFORM-d) δ ppm 0.84-0.92 (12H, m), 1.03-1.13 (1H, m), 1.22-1.35 (2H, m), 1.47-1.57 (6H, m), 1.67-1.79 (2H, m), 1.90-1.97 (1H, m), 2.21-2.48 (4H, m), 2.91-3.01 (1H, m), 3.27-3.33 (1H, m), 3.47-3.53 (1H, m), 3.72-3.78 (1H, m), 4.50-4.71 (4H, m), 4.83-4.88 (1H, m), 5.17-5.36 (4H, m), 5.84-5.96 (2H, m), 6.87 (1H, q, J=5.3 Hz)

MS m/z: 610 [M+H]+

(2) Resolution of 6-prop-2-en-1-yl 2-{1-[({[(1R,2S,4R)-1,7,7-trimethylbicyclo[2.2.1]heptan-2-yl]oxy}carbonyl)oxy]ethyl}(1R,2R,3R,5R,6R)-6-fluoro-2-({[(prop-2-en-1-yl)oxy]carbonyl}amino)-3-propoxybicyclo[3.1.0]hexane-2,6-dicarboxylate

[Formula 74]

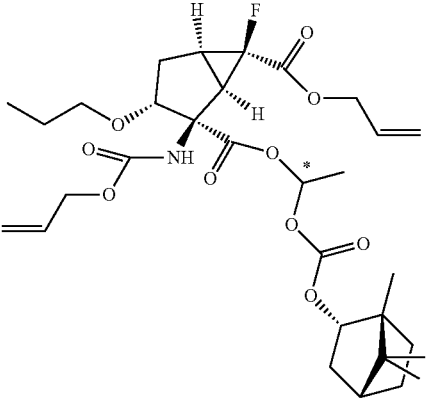

The compound (0.24 g, 0.40 mmol) obtained in Example 20(1) was separated by chiral column chromatography (CHIRALPAK ID, n-Hexane/EtOH=85:15) to obtain a fraction of the 1st peak as the compound of Example 20(2)-A (0.056 g, colorless oil) and a fraction of the 2nd peak as the compound of Example 20(2)-B (0.10 g, colorless amorphous).

Retention time: Example 20(2)-A; 3.83 min., Example 20(2)-B; 4.47 min. (CHIRAL PAK ID-3, n-Hexane/IPA=85:15)

(3) (1R,2R,3R,5R,6R)-2-Amino-6-fluoro-3-propoxy-2-({1-[({[(1R,2S,4R)-1,7,7-trimethylbicyclo[2.2.1]heptan-2-yl]oxy}carbonyl)oxy]ethoxy}carbonyl)bicyclo[3.1.0]hexane-6-carboxylic Acid (Example 20)

[Formula 75]

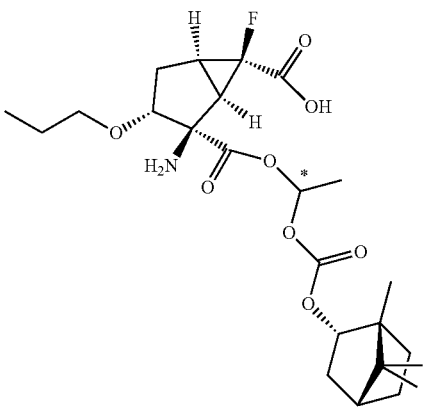

The title compound of Example 20 (0.019 g) was obtained (colorless solid) by the same procedure as in Example 15-(4) using the compound of Example 20(2)-A (0.056 g, 0.092 mmol) obtained in Step (2) as a starting material.

1H NMR (400 MHz, DMSO-d6) δ ppm 0.77-0.89 (12H, m), 1.00 (1H, dd, J=13.9, 3.3 Hz), 1.13-1.23 (1H, m), 1.24-1.33 (1H, m), 1.36-1.47 (2H, m), 1.50 (3H, d, J=5.5 Hz), 1.66-1.83 (3H, m), 1.97-2.22 (3H, m), 2.26-2.36 (2H, m), 3.24-3.32 (1H, m), 3.40-3.46 (1H, m), 3.56-3.63 (1H, m), 4.74 (1H, m, J=9.6, 2.3 Hz), 6.72 (1H, q, J=5.3 Hz)

MS m/z: 486 [M+H]+

Example 21 Synthesis of (1R,2R,3R,5R,6R)-2-amino-6-fluoro-3-[(4-fluorophenyl)methoxy]-2-({1-[({[(1R,2R,4S)-1,3,3-trimethylbicyclo[2.2.1]heptan-2-yl]oxy}carbonyl)oxy]ethoxy}carbonyl)bicyclo[3.1.0]hexane-6-carboxylic Acid

[Formula 76]

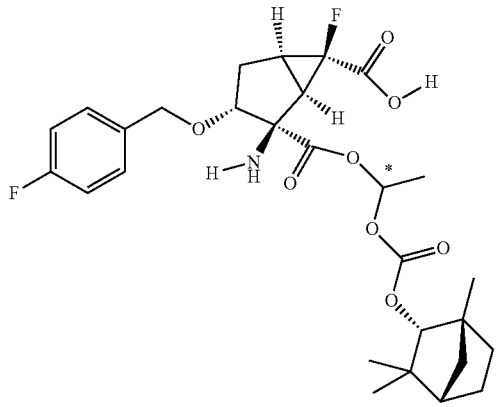

(1) 1-Chloroethyl (1R,2R,4S)-1,3,3-trimethylbicyclo[2.2.1]heptan-2-yl carbonate

[Formula 77]

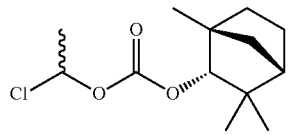

The title compound (6.2 g) was obtained (colorless oil) by the same procedure as in Example 15(1) using (+)-fenchol (5.0 g, 32.41 mmol) as a starting material.

1H NMR (400 MHz, CHLOROFORM-d) δ ppm 0.86 (3H, d, J=7.8 Hz), 1.10-1.17 (7H, m), 1.22 (1H, dd, J=10.4, 1.5 Hz), 1.42-1.54 (1H, m), 1.56-1.62 (1H, m), 1.67-1.81 (3H, m), 1.85 (3H, d, J=5.7 Hz), 4.25-4.34 (1H, m), 6.41-6.47 (1H, m)

MS m/z: 283 [M+Na]+

(2) 6-Prop-2-en-1-yl 2-{1-[({[(1R,2R,4S)-1,3,3-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 78]

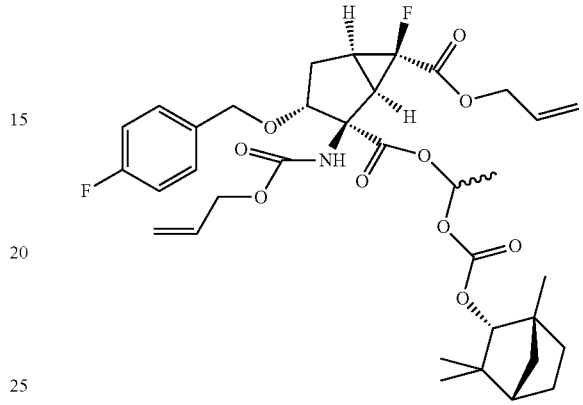

The title compound (0.29 g) was obtained as a diastereomer mixture (colorless amorphous) by the same procedure as in Example 15-(2) using potassium salt (0.40 g, 0.81 mmol) of the compound obtained in Example 1-(2) and the compound (0.42 g, 1.63 mmol) obtained in Example 21-(1) as starting materials.

1H NMR (400 MHz, CHLOROFORM-d) δ ppm 0.79-0.90 (3H, m), 1.00-1.12 (7H, m), 1.15-1.22 (1H, m), 1.41-1.58 (5H, m), 1.62-1.77 (3H, m), 2.20-2.28 (1H, m), 2.36-2.45 (2H, m), 2.96 (1H, br s), 3.79-3.85 (1H, m), 4.20-4.26 (1H, m), 4.44-4.71 (6H, m), 5.04 (1H, br s), 5.19-5.36 (4H, m), 5.85-5.95 (2H, m), 6.80-6.93 (1H, m), 7.02 (2H, t, J=8.7 Hz), 7.25-7.28 (2H, m)

MS m/z: 676 [M+H]+

(3) Resolution of 6-prop-2-en-1-yl 2-{1-[({[(1R,2R,4S)-1,3,3-trimethylbicyclo[2.2.1]heptan-2-yl]oxy}carbonyl)oxy]ethyl}(1R,2R,3R,5R,6R)-6-fluoro-3-[(4-fluorophenyl)methoxy]-2-({[(prop-2-en-1-yl)oxy]carbonyl}amino)bicyclo[3.1.0]hexane-2,6-dicarboxylate

[Formula 79]

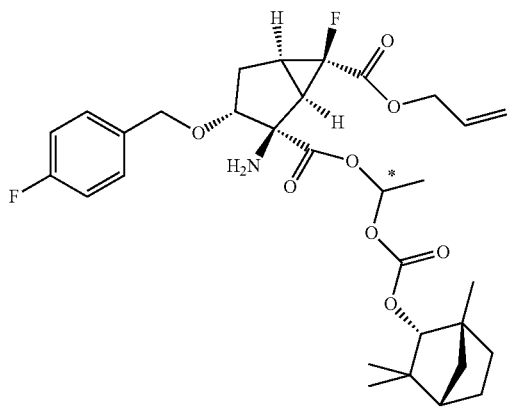

The compound (0.19 g, 0.28 mmol) obtained in Example 21(2) was separated by chiral column chromatography (CHIRALPAK ID, n-Hexane/EtOH=85:15) to obtain a fraction of the 1st peak as the compound of Example 21(3)-A (0.061 g) and a fraction of the 2nd peak as the compound of Example 21(3)-B (0.042 g) (both were colorless oils).
Retention time: Example 21(3)-A; 3.43 min., Example 21(3)-B; 4.60 min. (CHIRAL PAK ID-3, n-Hexane/EtOH=85:15)

(4) (1R,2R,3R,5R,6R)-2-Amino-6-fluoro-3-[(4-fluorophenyl)methoxy]-2-({1-[({[(1R,2R,4S)-1,3,3-trimethylbicyclo[2.2.1]heptan-2-yl]oxy}carbonyl)oxy]ethoxy}carbonyl)bicyclo[3.1.0]hexane-6-carboxylic Acid (Example 21)

The title compound of Example 21 (0.024 g) was obtained (colorless solid) by the same procedure as in Example 15-(4) using the compound of Example 21(3)-B (0.042 g, 0.063 mmol) obtained in Example 21(3) as a starting material.
1H NMR (400 MHz, DMSO-d6) δ ppm 0.77 (3H, s), 0.97-1.21 (8H, m), 1.37-1.48 (4H, m), 1.52-1.66 (4H, m), 1.70 (1H, br d, J=3.3 Hz), 1.91-2.05 (3H, m), 2.17-2.37 (2H, m), 3.72 (1H, m), 4.18 (1H, d, J=1.6 Hz), 4.45 (1H, d, J=11.6 Hz), 4.55 (1H, d, J=11.9 Hz), 6.69 (1H, q, J=5.5 Hz), 7.12-7.19 (2H, m), 7.26-7.32 (2H, m)
MS m/z: 552 [M+H]+

Production of active forms (II)-4 to (II)-14

[Formula 81]

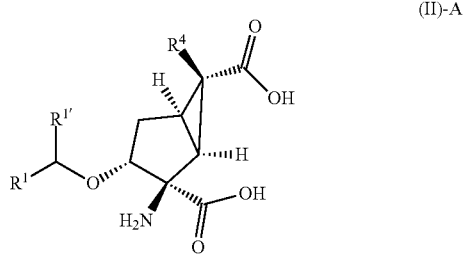

(II)-A

[Formula 80]

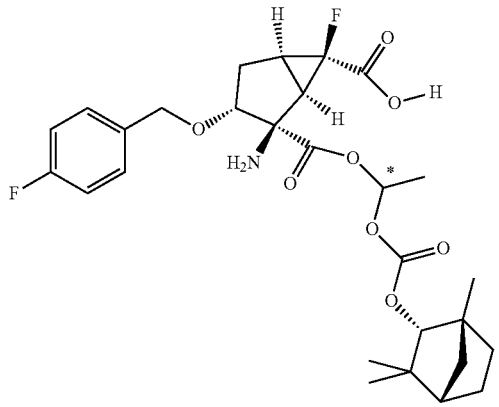

The structural formulas, names and instrument data (1H NMR and detected MS spectrum data) of active form compounds synthesized by an approach in accordance with the production process described in WO03/061698 or WO2011/061935 (Compound Nos. (II)-4 to (II)-13) and an active form compound synthesized by an approach in accordance with the production process described in Example 38 (Compound No. (II)-14) are shown in Table A.

TABLE A

| Compound No. | Structure | Chemical Name | 1H NMR | Detected MS |
|---|---|---|---|---|
| (II)-4 | 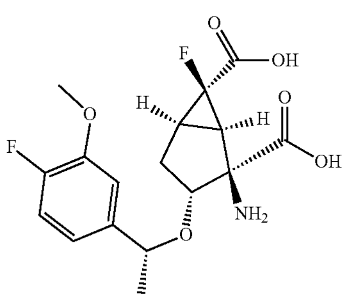 [SMILES: COc1cc([C@@H](C)O[C@@H]2C[C@@H]3[C@H]([C@]2(N)C(=O)O)[C@@]3(F)C(=O)O)ccc1F] | (1R,2R,3R,5R,6R)-2-amino-6-fluoro-3-[(1R)-1-(4-fluoro-3-methoxyphenyl)-ethoxy]bicyclo[3.1.0]-hexane-2,6-dicarboxylic acid | 1H NMR (400 MHz, DMSO-d6) δ ppm 1.24 (d, J = 6.4 Hz, 3 H), 1.83-2.07 (m, 3 H), 2.19-2.30 (m, 1 H), 3.58-3.75 (m, 1 H), 3.83 (s, 3 H), 4.56 (q, J = 6.0 Hz, 1 H), 6.82 (ddd, J = 6.2, 4.3, 2.2 Hz, 1 H), 6.99-7.25 (m, 2 H) | 372 [M + H]+ |
| (II)-5 | 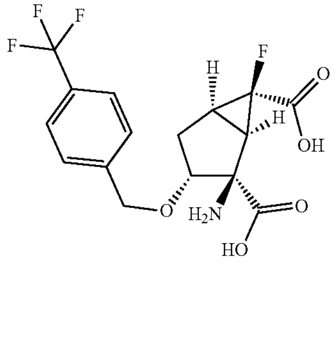 [SMILES: N[C@]1(C(=O)O)[C@H]2[C@@H](C[C@H]1OCc1ccc(C(F)(F)F)cc1)[C@]2(F)C(=O)O] | (1R,2R,3R,5R,6R)-2-amino-6-fluoro-3-{[4-(trifluoromethyl)-phenyl]-methoxy}bicyclo-[3.1.0]hexane-2,6-dicarboxylic acid | 1H NMR (600 MHz, DMSO-d6) δ ppm 2.07 (2 H, br s), 2.22-2.56 (4 H, m), 3.90-3.97 (1 H, m), 4.51 (1 H, d, J = 12.4 Hz), 4.65 (1 H, d, J = 12.4 Hz), 7.52 (2 H, d, J = 8.3 Hz), 7.69 (2 H, d, J = 8.3 Hz) | 378 [M + H]+ |

TABLE A-continued

| Compound No. | Structure | Chemical Name | 1H NMR | Detected MS |
|---|---|---|---|---|
| (II)-6 | 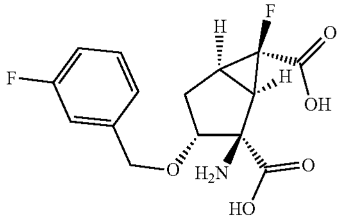 [SMILES: N[C@]1(C(=O)O)[C@H]2[C@@H](C[C@H]1OCc1cccc(F)c1)[C@]2(F)C(=O)O] | (1R,2R,3R,5R,6R)-2-amino-6-fluoro-3-[(3-fluorophenyl)-methoxy]-bicyclo[3.1.0]hexane-2,6-dicarboxylic acid | 1H NMR (600 MHz, DMSO-d6) δ ppm 2.05 (2 H, br s), 2.21-2.55 (4 H, m), 3.88-3.93 (1 H, m), 4.42 (1 H, d, J = 12.0 Hz), 4.55 (1 H, d, J = 12.0 Hz), 7.06-7.11 (1 H, m), 7.11-7.17 (2 H, m), 7.31-7.40 (1 H, m) | 328 [M + H]+ |
| (II)-7 | 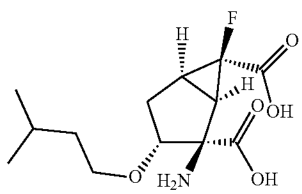 [SMILES: CC(C)CCO[C@@H]1C[C@@H]2[C@H]([C@]1(N)C(=O)O)[C@@]2(F)C(=O)O] | (1R,2R,3R,5R,6R)-2-amino-6-fluoro-3-(3-methylbutoxy)bicyclo-[3.1.0]hexane-2,6-dicarboxylic acid | 1H NMR (400 MHz, DMSO-d6) δ ppm 0.84 (6 H, dd, J = 6.7, 2.4 Hz), 1.30 (2 H, q, J = 6.8 Hz), 1.53-1.66 (1 H, m), 2.01 (2 H, d, J = 2.9 Hz), 2.20-2.31 (2 H, m), 3.14-3.40 (1 H, m), 3.40-3.59 (1 H, m), 3.61-3.85 (1 H, m) | 290 [M + H]+ |
| (II)-8 | 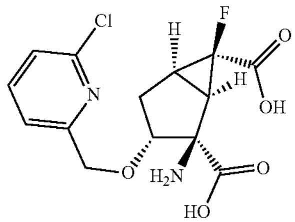 [SMILES: N[C@]1(C(=O)O)[C@H]2[C@@H](C[C@H]1OCc1cccc(Cl)n1)[C@]2(F)C(=O)O] | (1R,2R,3R,5R,6R)-2-amino-3-[(6-chloropyridin-2-yl)methoxy]-6-fluorobicyclo-[3.1.0]hexane-2,6-dicarboxylic acid | 1H NMR (600 MHz, DMSO-d6) δ ppm 2.08 (2 H, br d, J = 2.5 Hz), 2.28-2.54 (4 H, m), 3.93-4.01 (1 H, m), 4.48 (1 H, d, J = 13.6 Hz), 4.61 (1 H, d, J = 13.6 Hz), 7.40 (1 H, d, J = 7.8 Hz), 7.44 (1 H, d, J = 7.8 Hz), 7.87 (1 H, t, J = 7.8 Hz) | 345 [M + H]+ |
| (II)-9 | 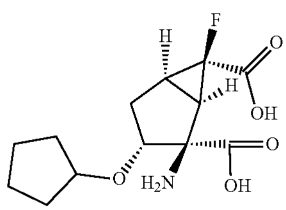 [SMILES: N[C@]1(C(=O)O)[C@H]2[C@@H](C[C@H]1OC1CCCC1)[C@]2(F)C(=O)O] | (1R,2R,3R,5R,6R)-2-amino-3-(cyclopentyloxy)-6-fluorobicyclo[3.1.0]-hexane-2,6-dicarboxylic acid | 1H NMR (400 MHz, DMSO-d6) δ ppm 1.37-1.65 (8 H, m), 1.91-2.09 (2 H, m), 2.17-2.35 (2 H, m), 3.71-3.82 (1 H, m), 3.86-3.97 (1 H, m) | 288 [M + H]+ |
| (II)-10 | 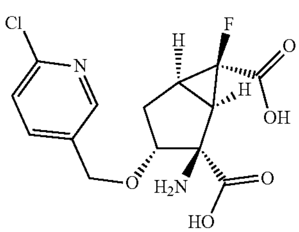 [SMILES: N[C@]1(C(=O)O)[C@H]2[C@@H](C[C@H]1OCc1ccc(Cl)nc1)[C@]2(F)C(=O)O] | (1R,2R,3R,5R,6R)-2-amino-3-[(6-chloropyridin-3-yl)methoxy]-6-fluorobicyclo-[3.1.0]hexane-2,6-dicarboxylic acid | 1H NMR (600 MHz, DMSO-d6) δ ppm 1.97-2.57 (6 H, m), 3.86-4.00 (1 H, m), 4.38-4.64 (2 H, m), 7.50 (1 H, d, J = 8.3 Hz), 7.74-7.88 (1 H, m), 8.34 (1 H, d, J = 1.7 Hz) | 345 [M + H]+ |
| (II)-11 | 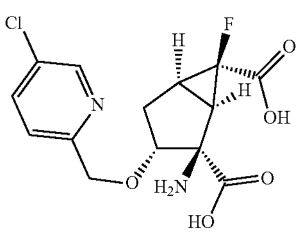 [SMILES: N[C@]1(C(=O)O)[C@H]2[C@@H](C[C@H]1OCc1ccc(Cl)cn1)[C@]2(F)C(=O)O] | (1R,2R,3R,5R,6R)-2-amino-3-[(5-chloropyridin-2-yl)methoxy]-6-fluorobicyclo-[3.1.0]hexane-2,6-dicarboxylic acid | 1H NMR (600 MHz, DMSO-d6) δ ppm 2.07 (2 H, br d, J = 2.5 Hz), 2.27-2.56 (4 H, m), 3.91-4.04 (1 H, m), 4.50 (1 H, d, J = 13.2 Hz), 4.63 (1 H, d, J = 13.2 Hz), 7.48 (1 H, d, J = 8.3 Hz), 7.94 (1 H, dd, J = 8.3, 2.5 Hz), 8.53 (1 H, d, J = 2.5 Hz) | 345 [M + H]+ |
| (II)-12 | 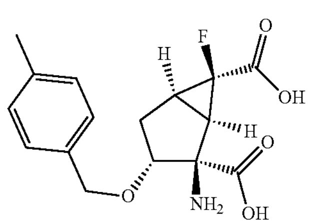 [SMILES: Cc1ccc(CO[C@@H]2C[C@@H]3[C@H]([C@]2(N)C(=O)O)[C@@]3(F)C(=O)O)cc1] | (1R,2R,3R,5R,6R)-2-amino-6-fluoro-3-[(4-methylphenyl)-methoxy]bicyclo-[3.1.0]-hexane-2,6-dicarboxylic acid | 1H NMR (400 MHz, DMSO-d6) δ ppm 2.05 (br d, J = 2.9 Hz, 2 H), 2.16-2.37 (m, 5 H), 3.79-3.99 (m, 1 H), 4.26-4.59 (m, 2 H), 7.01-7.29 (m, 4 H) | 324 [M + H]+ |

TABLE A-continued

| Compound No. | Structure | Chemical Name | 1H NMR | Detected MS |
|---|---|---|---|---|
| (II)-13 | 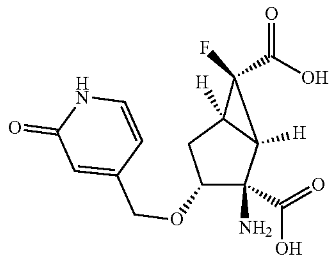 [SMILES: N[C@]1(C(=O)O)[C@H]2[C@@H](C[C@H]1OCc1cc[nH]c(=O)c1)[C@]2(F)C(=O)O] | (1R,2R,3R,5R,6R)-2-amino-6-fluoro-3-[(2-oxo-1,2-dihydro-pyridin-4-yl)methoxy]bicyclo-[3.1.0]hexane-2,6-dicarboxylic acid | 1H NMR (600 MHz, DMSO-d6) δ ppm 2.03-2.12 (2 H, m), 2.26-2.32 (1 H, m), 2.32-2.40 (1 H, m), 3.80-3.93 (1 H, m), 4.17-4.45 (2 H, m), 6.06 (1 H, d, J = 7.0 Hz), 6.22 (1 H, s), 7.28 (1 H, d, J = 7.0 Hz) | 327 [M + H]+ |
| (II)-14 | 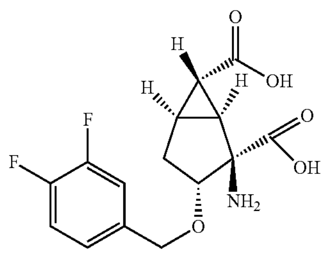 [SMILES: N[C@]1(C(=O)O)[C@H]2[C@@H](C[C@H]1OCc1ccc(F)c(F)c1)[C@@H]2C(=O)O] | (1S,2R,3R,5R,6S)-2-amino-3-[(3,4-difluorophenyl)-methoxy]bicyclo-[3.1.0]hexane-2,6-dicarboxylic acid | 1H NMR (400 MHz, DMSO-d6) δ ppm 1.65-1.73 (1 H, m), 1.74-1.81 (1 H, m), 1.81-1.88 (1 H, m), 2.05-2.21 (2 H, m), 3.51-3.62 (1 H, m), 4.34 (1 H, d, J = 12.0 Hz), 4.45 (1 H, d, J = 11.9 Hz), 7.11-7.17 (1 H, m), 7.33-7.43 (2 H, m) | 328 [M + H]+ |

The structural formulas, names and instrument data (1H NMR and detected MS spectrum data) of compounds synthesized in the same way as in Example 4 using the corresponding active forms described in [Table A] as starting materials are shown in Table B (Example Nos. 22 to 30).

TABLE B

| Example | Structure | Chemical Name | 1H NMR | Detected MS |
|---|---|---|---|---|
| 22 | 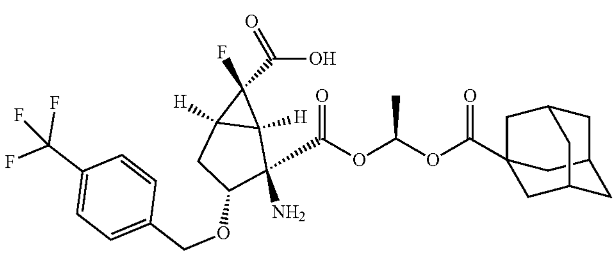 [SMILES: C[C@@H](OC(=O)C12CC3CC(CC(C3)C1)C2)OC(=O)[C@@]1(N)[C@H]2[C@@H](C[C@H]1OCc1ccc(C(F)(F)F)cc1)[C@]2(F)C(=O)O] | (1R,2R,3R,5R,6R)-2-amino-6-fluoro-2-({(1S)-1-[(tricyclo[3.3.1.1$^{3,7}$]decane-1-carbonyl)oxy]ethoxy}carbonyl)-3-{[4-(trifluoromethyl)phenyl]methoxy}bicyclo-[3.1.0]hexane-6-carboxylic acid | 1H NMR (600 MHz, DMSO-d6) δ ppm 1.43 (3 H, d, J = 5.4 Hz), 1.56-1.69 (6 H, m), 1.71-1.81 (6 H, m), 1.89-2.03 (5 H, m), 2.20-2.55 (4 H, m), 3.72-3.80 (1 H, m), 4.55-4.74 (2 H, m), 6.77 (1 H, q, J = 5.4 Hz), 7.47 (2 H, d, J = 7.8 Hz), 7.70 (2 H, d, J = 8.3 Hz) | 582 [M − H]− |
| 23 | 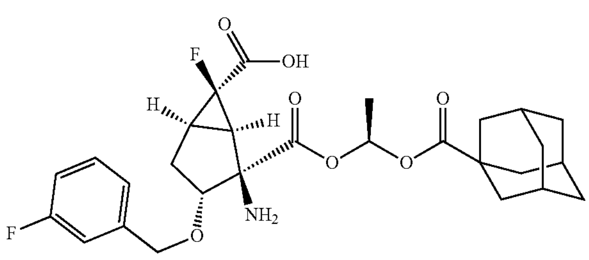 [SMILES: C[C@@H](OC(=O)C12CC3CC(CC(C3)C1)C2)OC(=O)[C@@]1(N)[C@H]2[C@@H](C[C@H]1OCc1cccc(F)c1)[C@]2(F)C(=O)O] | (1R,2R,3R,5R,6R)-2-amino-6-fluoro-3-[(3-fluorophenyl)-methoxy]-2-({(1S)-1-[(tricyclo[3.3.1.1$^{3,7}$]-decane-1-carbonyl)oxy]ethoxy}-carbonyl)bicyclo-[3.1.0]hexane-6-carboxylic acid | 1H NMR (600 MHz, DMSO-d6) δ ppm 1.42 (3 H, d, J = 5.4 Hz), 1.57-1.70 (6 H, m), 1.73-1.82 (6 H, m), 1.89-2.01 (5 H, m), 2.18-2.53 (4 H, m), 3.69-3.78 (1 H, m), 4.47-4.64 (2 H, m), 6.77 (1 H, q, J = 5.4 Hz), 7.02-7.14 (3 H, m), 7.33-7.41 (1 H, m) | 532 [M − H]− |

TABLE B-continued

| Example | Structure | Chemical Name | 1H NMR | Detected MS |
|---|---|---|---|---|
| 24 | 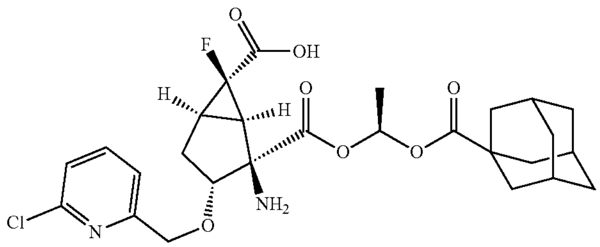 [SMILES: C[C@@H](OC(=O)C12CC3CC(CC(C3)C1)C2)OC(=O)[C@@]1(N)[C@H]2[C@@H](C[C@H]1OCc1cccc(Cl)n1)[C@]2(F)C(=O)O] | (1R,2R,3R,5R,6R)-2-amino-3-[(6-chloropyridin-2-yl)-methoxy]-6-fluoro-2-({(1S)-1-[(tricyclo-[3.3.1.1$^{3,7}$]decane-1-carbonyl)oxy]-ethoxy}-carbonyl)bicyclo-[3.1.0]hexane-6-carboxylic acid | 1H NMR (600 MHz, DMSO-d6) δ ppm 1.44 (3 H, d, J = 5.4 Hz), 1.56-1.81 (7 H, m), 1.85-2.05 (6 H, m), 2.26 (1 H, ddd, J = 13.2, 8.1, 4.7 Hz), 2.36-2.42 (1 H, m), 3.75-3.83 (1 H, m), 4.51-4.68 (2 H, m), 6.72-6.81 (1 H, m), 7.33 (1 H, d, J = 7.0 Hz), 7.41 (1 H, d, J = 7.8 Hz), 7.88 (1 H, t, J = 7.8 Hz) | 551 [M + H]+ |
| 25 | 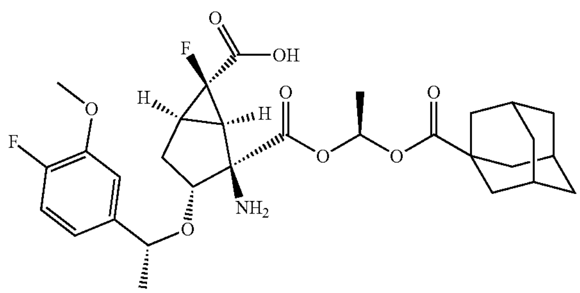 [SMILES: COc1cc([C@@H](C)O[C@@H]2C[C@@H]3[C@H]([C@]2(N)C(=O)O[C@@H](C)OC(=O)C24CC5CC(CC(C5)C2)C4)[C@@]3(F)C(=O)O)ccc1F] | (1R,2R,3R,5R,6R)-2-amino-6-fluoro-3-[(1R)-1-(4-fluoro-3-methoxyphenyl)-ethoxy]-2-({(1S)-1-[(tricyclo[3.3.1.1$^{3,7}$]-decane-1-carbonyl)oxy]-ethoxy}-carbonyl)bicyclo-[3.1.0]hexane-6-carboxylic acid | 1H NMR (400 MHz, CHLOROFORM-d) δ ppm 1.28 (d, J = 6.2 Hz, 3 H), 1.53 (d, J = 5.4 Hz, 3 H), 1.70 (br s, 6 H), 1.88 (br, s, 6 H), 2.01 (br s, 3 H), 2.05-2.11 (m, 1 H), 2.13-2.33 (m, 4 H), 3.87 (s, 3 H), 3.90-4.01 (m, 1 H), 4.50-4.64 (m, 1 H), 6.73-6.79 (m, 1 H), 6.83-7.07 (m, 3 H) | 578 [M + H]+ |
| 26 | 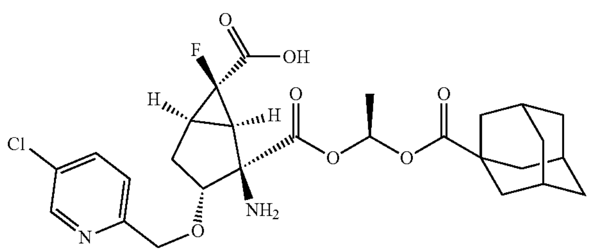 [SMILES: C[C@@H](OC(=O)C12CC3CC(CC(C3)C1)C2)OC(=O)[C@@]1(N)[C@H]2[C@@H](C[C@H]1OCc1ccc(Cl)cn1)[C@]2(F)C(=O)O] | (1R,2R,3R,5R,6R)-2-amino-3-[(5-chloropyridin-2-yl)-methoxy]-6-fluoro-2-({(1S)-1-[(tricyclo-[3.3.1.1$^{3,7}$]decane-1-carbonyl)oxy]-ethoxy}-carbonyl)bicyclo-[3.1.0]hexane-6-carboxylic acid | 1H NMR (600 MHz, DMSO-d6) δ ppm 1.43 (3 H, d, J = 5.4 Hz), 1.56-1.70 (6 H, m), 1.76 (6 H, br s), 1.88-2.03 (5 H, m), 2.26 (1 H, br, d, J = 8.3 Hz), 2.34-2.56 (3 H, m), 3.78 (1 H, br d, J = 5.8 Hz), 4.52-4.69 (2 H, m), 6.76 (1 H, q, J = 5.6 Hz), 7.36 (1 H, d, J = 8.3 Hz), 7.95 (1 H, dd, J = 8.3, 2.5 Hz), 8.55 (1 H, d, J = 2.1 Hz) | 551 [M + H]+ |
| 27 | 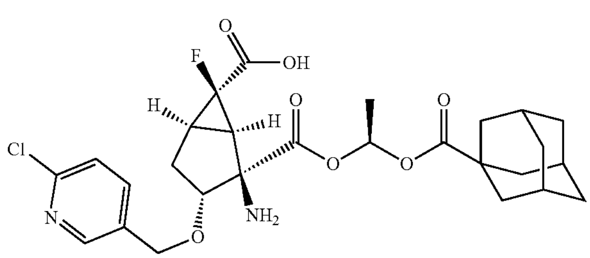 [SMILES: C[C@@H](OC(=O)C12CC3CC(CC(C3)C1)C2)OC(=O)[C@@]1(N)[C@H]2[C@@H](C[C@H]1OCc1ccc(Cl)nc1)[C@]2(F)C(=O)O] | (1R,2R,3R,5R,6R)-2-amino-3-[(6-chloropyridin-3-yl)-methoxy]-6-fluoro-2-({(1S)-1-[(tricyclo-[3.3.1.1$^{3,7}$]decane-1-carbonyl)oxy]-ethoxy}-carbonyl)bicyclo-[3.1.0]hexane-6-carboxylic acid | 1H NMR (600 MHz, DMSO-d6) δ ppm 1.40 (3 H, d, J = 5.4 Hz), 1.57-1.69 (6 H, m), 1.70-1.81 (6 H, m), 1.84-2.02 (5 H, m), 2.22 (1 H, ddd, J = 13.0, 8.1, 4.5 Hz), 2.31-2.54 (3 H, m), 3.71-3.79 (1 H, m), 4.51-4.66 (2 H, m), 6.75 (1 H, q, J = 5.4 Hz), 7.51 (1 H, d, J = 8.3 Hz), 7.73 (1 H, dd, J = 8.3, 2.5 Hz), 8.31 (1 H, d, J = 2.5 Hz) | 549 [M − H]− |

TABLE B-continued

| Example | Structure | Chemical Name | 1H NMR | Detected MS |
|---|---|---|---|---|
| 28 | 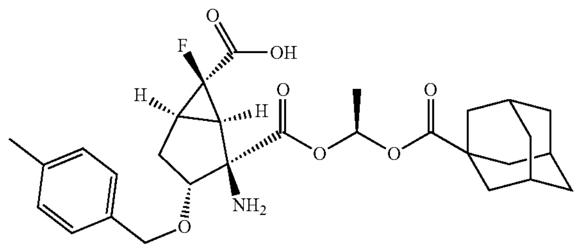 [SMILES: Cc1ccc(CO[C@@H]2C[C@@H]3[C@H]([C@]2(N)C(=O)O[C@@H](C)OC(=O)C24CC5CC(CC(C5)C2)C4)[C@@]3(F)C(=O)O)cc1] | (1R,2R,3R,5R,6R)-2-amino-6-fluoro-3-[(4-methylphenyl)methoxy]-2-({(1S)-1-[(tricyclo[3.3.1.1$^{3,7}$]-decane-1-carbonyl)-oxy]ethoxy}-carbonyl)-bicyclo[3.1.0]hexane-6-carboxylic acid | 1H NMR (400 MHz, DMSO-d6) δ ppm 1.41 (d, J = 5.4 Hz, 3 H), 1.56-1.69 (m, 6 H), 1.71-1.81 (m, 6 H), 1.87-2.02 (m, 3 H), 2.12-2.40 (m, 7 H), 3.67-3.79 (m, 1 H), 4.36-4.57 (m, 2 H), 6.77 (q, J = 5.4 Hz, 1 H), 7.14 (s, 4 H) | 528 [M − H]− |
| 29 | 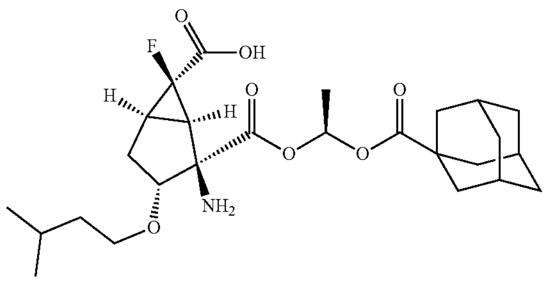 [SMILES: CC(C)CCO[C@@H]1C[C@@H]2[C@H]([C@]1(N)C(=O)O[C@@H](C)OC(=O)C13CC4CC(CC(C4)C1)C3)[C@@]2(F)C(=O)O] | (1R,2R,3R,5R,6R)-2-amino-6-fluoro-3-(3-methylbutoxy)-2-({(1S)-1-[(tricyclo[3.3.1.1$^{3,7}$]-decane-1-carbonyl)-oxy]ethoxy}-carbonyl)-bicyclo[3.1.0]hexane-6-carboxylic acid | 1H NMR (400 MHz, DMSO-d6) δ ppm 0.83 (6 H, d, J = 6.6 Hz), 1.24-1.38 (2 H, m), 1.44 (3 H, d, J = 5.4 Hz), 1.52-1.73 (7 H, m), 1.73-1.86 (6 H, m), 1.90-2.00 (3 H, m), 2.06-2.42 (4 H, m), 3.32-3.41 (1 H, m), 3.45-3.53 (1 H, m), 3.55-3.61 (1 H, m), 6.75 (1 H, q, J = 5.3 Hz) | 494 [M − H]− |
| 30 | 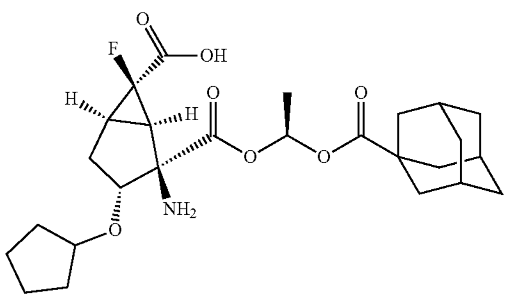 [SMILES: C[C@@H](OC(=O)C12CC3CC(CC(C3)C1)C2)OC(=O)[C@@]1(N)[C@H]2[C@@H](C[C@H]1OC1CCCC1)[C@]2(F)C(=O)O] | (1R,2R,3R,5R,6R)-2-amino-3-(cyclopentyloxy)-6-fluoro-2-({(1S)-1-[(tricyclo[3.3.1.1$^{3,7}$]-decane-1-carbonyl)-oxy]ethoxy}-carbonyl)-bicyclo[3.1.0]hexane-6-carboxylic acid | 1H NMR (400 MHz, CHLOROFORM-d) δ ppm 1.41-1.75 (m, 17 H), 1.88 (br s, 6 H), 2.01 (br s, 3 H), 2.20 (br s, 1 H), 2.26-2.37 (m, 2 H), 2.47 (br dd, J = 13.5, 7.5 Hz, 1 H), 3.99 (br s, 1 H), 4.08 (br, 1 H), 6.87 (q, J = 5.2 Hz, 1 H) | 492 [M − H]− |

The structural formulas, names and instrument data (1H NMR and detected MS spectrum data) of compounds synthesized in the same way as in Example 1 using the corresponding active forms described in [Table A] as starting materials are shown in Table C (Example Nos. 31 to 34).

TABLE C

| Example | Structure | Chemical Name | 1H NMR | Detected MS |
|---|---|---|---|---|
| 31 | 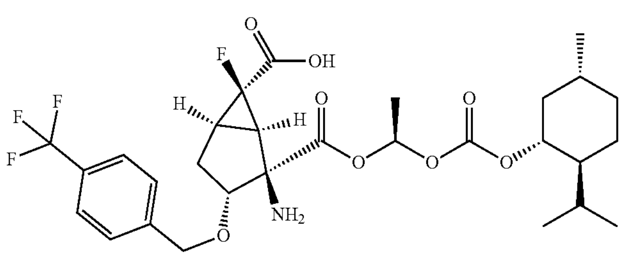 [SMILES: CC(C)[C@@H]1CC[C@@H](C)C[C@H]1OC(=O)O[C@H](C)OC(=O)[C@@]1(N)[C@H]2[C@@H](C[C@H]1OCc1ccc(C(F)(F)F)cc1)[C@]2(F)C(=O)O] | (1R,2R,3R,5R,6R)-2-amino-6-fluoro-2-({(1R)-1-[({[(1R,2S,5R)-5-methyl-2-(propan-2-yl)-cyclohexyl]oxy}-carbonyl)oxy]ethoxy}-carbonyl)-3-{[4-(trifluoromethyl)-phenyl]methoxy}-bicyclo[3.1.0]hexane-6-carboxylic acid | 1H NMR (600 MHz, DMSO-d6) δ ppm 0.67-1.10 (13H, m), 1.28-1.49 (5 H, m), 1.62 (2 H, br d, J = 12.0 Hz), 1.77-2.11 (5 H, m), 2.20-2.39 (2 H, m), 3.71-3.83 (1 H, m), 4.38-4.50 (1 H, m), 4.54-4.76 (2 H, m), 6.68 (1 H, q, J = 5.4 Hz), 7.47 (2 H, br d, J = 7.8 Hz), 7.70 (2 H, br d, J = 7.8 Hz) | 604 [M + H]+ |

TABLE C-continued

| Example | Structure | Chemical Name | 1H NMR | Detected MS |
|---|---|---|---|---|
| 32 | 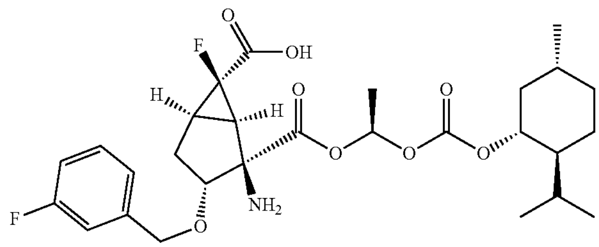 [SMILES: CC(C)[C@@H]1CC[C@@H](C)C[C@H]1OC(=O)O[C@H](C)OC(=O)[C@@]1(N)[C@H]2[C@@H](C[C@H]1OCc1cccc(F)c1)[C@]2(F)C(=O)O] | (1R,2R,3R,5R,6R)-2-amino-6-fluoro-3-[(3-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid | 1H NMR (600 MHz, DMSO-d6) δ ppm 0.71-1.08 (11 H, m), 1.35 (1 H, br t, J = 11.8 Hz), 1.43 (3 H, br d, J = 5.4 Hz), 1.62 (2 H, br d, J = 11.6 Hz), 1.76-2.08 (4 H, m), 2.21-2.41 (2 H, m), 3.69-3.79 (1 H, m), 4.43 (1 H, td, J = 10.8, 4.3 Hz), 4.48-4.65 (2 H, m), 6.68 (1 H, q, J = 5.4 Hz), 7.01-7.16 (3 H, m), 7.30-7.45 (1 H, m) | 553 [M + H]+ |
| 33 | 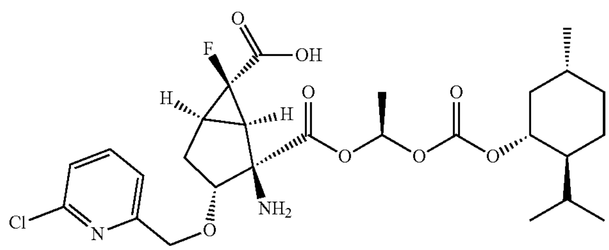 [SMILES: CC(C)[C@@H]1CC[C@@H](C)C[C@H]1OC(=O)O[C@H](C)OC(=O)[C@@]1(N)[C@H]2[C@@H](C[C@H]1OCc1cccc(Cl)n1)[C@]2(F)C(=O)O] | (1R,2R,3R,5R,6R)-2-amino-3-[(6-chloropyridin-2-yl)methoxy]-6-fluoro-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid | 1H NMR (600 MHz, DMSO-d6) δ ppm 0.73 (3 H, d, J = 6.6 Hz), 0.77-0.89 (7 H, m), 0.91-1.08 (2 H, m), 1.30-1.49 (5 H, m), 1.62 (2 H, br d, J = 11.1 Hz), 1.82 (1 H, dtd, J = 14.0, 6.9, 6.9, 2.7 Hz), 1.87-1.94 (1 H, m), 1.98-2.07 (2 H, m), 2.28 (1 H, ddd, J = 13.5, 7.9, 5.4 Hz), 2.36-2.53 (2 H, m), 3.76-3.83 (1 H, m), 4.43 (1 H, td, J = 10.9, 4.5 Hz), 4.52-4.66 (2 H, m), 6.68 (1 H, q, J = 5.4 Hz), 7.33 (1 H, d, J = 7.4 Hz), 7.41 (1 H, d, J = 7.8 Hz), 7.87 (1 H, t, J = 7.8 Hz) | 571 [M + H]+ |
| 34 | 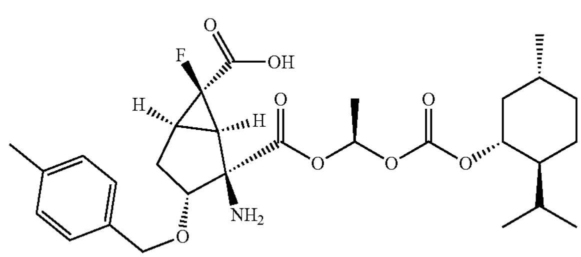 [SMILES: Cc1ccc(CO[C@@H]2C[C@@H]3[C@H]([C@]2(N)C(=O)O[C@@H](C)OC(=O)O[C@@H]2C[C@H](C)CC[C@H]2C(C)C)[C@@]3(F)C(=O)O)cc1] | (1R,2R,3R,5R,6R)-2-amino-6-fluoro-3-[(4-methylphenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic acid | 1H NMR (400 MHz, DMSO-d6) δ ppm 0.74 (d, J = 7.0 Hz, 3 H), 0.78-0.91 (m, 7 H), 0.92-1.12 (m, 2 H), 1.31-1.49 (m, 5 H), 1.57-1.67 (m, 2 H), 1.76-2.05 (m, 4 H), 2.16-2.37 (m, 5 H), 3.65-3.78 (m, 1 H), 4.32-4.61 (m, 3 H), 6.67 (q, J = 5.4 Hz, 1 H), 7.13 (s, 4 H) | 550 [M + H]+ |

The structural formulas, names and instrument data (1H NMR and detected MS spectrum data) of compounds synthesized in the same way as in Example 1 are shown in Table D (Example Nos. 35 to 37) except that steps corresponding to Example 1-(2) were carried out using a known compound chloromethyl cyclohexanecarboxylate, chloromethyl benzoate or chloromethyl 2,2-dimethylpropanoate instead of (1R)-1-chloroethyl (1R,2S,5R)-5-methyl-2-(propan-2-yl)cyclohexyl carbonate. (1R,2R,3R,5R,6R)-2-amino-2-({(1S)-1-[(2,2-dimethylpropanoyl)oxy]ethoxy}carbonyl)-6-fluoro-3-[(4-fluorophenyl)methoxy]bicyclo[3.1.0]hexane-6-carboxylic acid, (1R,2R,3R,5R,6R)-2-amino-2-{[(1S)-1-(benzoyloxy)ethoxy]carbonyl}-6-fluoro-3-[(4-fluorophenyl)methoxy]bicyclo[3.1.0]hexane-6-carboxylic acid, and, (1R,2R,3R,5R,6R)-2-amino-2-({(1S)-1-[(cyclohexanecarbonyl)oxy]ethoxy}carbonyl)-6-fluoro-3-[(4-fluorophenyl)methoxy]bicyclo[3.1.0]hexane-6-carboxylic acid may be synthesized in the same way.

TABLE D

| Example | Structure | Chemical Name | 1H NMR | Detected MS |
|---|---|---|---|---|
| 35 | 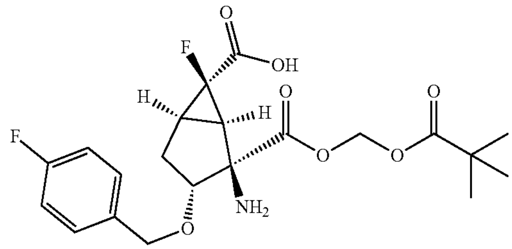 [SMILES: CC(C)(C)C(=O)OCOC(=O)[C@@]1(N)[C@H]2[C@@H](C[C@H]1OCc1ccc(F)cc1)[C@]2(F)C(=O)O] | (1R,2R,3R,5R,6R)-2-amino-2-({[(2,2-dimethylpropanoyl)oxy]methoxy}carbonyl)-6-fluoro-3-[(4-fluorophenyl)methoxy]bicyclo[3.1.0]hexane-6-carboxylic acid | 1H NMR (600 MHz, DMSO-d6) δ ppm 1.06 (9 H, d, J = 0.8 Hz), 1.93-2.01 (1 H, m), 2.05-2.11 (1 H, m), 2.11-2.21 (1 H, m), 2.23-2.32 (1 H, m), 3.68-3.78 (1 H, m), 4.42-4.60 (2 H, m), 5.77 (1 H, d, J = 5.8 Hz), 5.83 (1 H, d, J = 5.8 Hz), 7.15 (2 H, t, J = 8.7 Hz), 7.29 (2 H, dd, J = 8.3, 5.8 Hz) | 442 [M + H]+ |
| 36 | 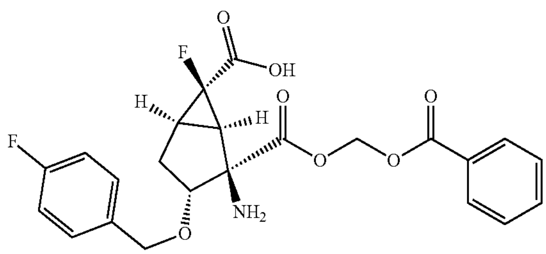 [SMILES: N[C@]1(C(=O)OCOC(=O)c2ccccc2)[C@H]2[C@@H](C[C@H]1OCc1ccc(F)cc1)[C@]2(F)C(=O)O] | (1R,2R,3R,5R,6R)-2-amino-2-{[(benzoyloxy)methoxy]carbonyl}-6-fluoro-3-[(4-fluorophenyl)methoxy]bicyclo[3.1.0]hexane-6-carboxylic acid | 1H NMR (600 MHz, DMSO-d6) δ ppm 2.00-2.05 (1 H, m), 2.13-2.29 (3 H, m), 3.65-3.78 (1 H, m), 4.32 (1 H, d, J = 12.0 Hz), 4.45 (1 H, d, J = 12.0 Hz), 5.98 (1 H, d, J = 5.8 Hz), 6.08 (1 H, d, J = 5.8 Hz), 6.92-7.04 (2 H, m), 7.08-7.18 (2 H, m), 7.42-7.52 (2 H, m), 7.60-7.73 (1 H, m), 7.90 (2 H, dd, J = 8.3, 1.2 Hz) | 462 [M + H]+ |
| 37 | 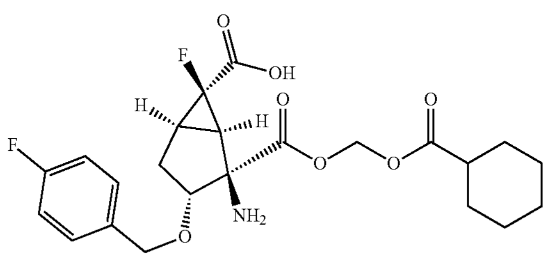 [SMILES: N[C@]1(C(=O)OCOC(=O)C2CCCCC2)[C@H]2[C@@H](C[C@H]1OCc1ccc(F)cc1)[C@]2(F)C(=O)O] | (1R,2R,3R,5R,6R)-2-amino-2-({[(cyclohexanecarbonyl)oxy]methoxy}carbonyl)-6-fluoro-3-[(4-fluorophenyl)methoxy]bicyclo[3.1.0]hexane-6-carboxylic acid | 1H NMR (600 MHz, DMSO-d6) δ ppm 1.00-1.28 (5 H, m), 1.46-1.75 (5 H, m), 1.99 (1 H, br s), 2.03-2.20 (3 H, m), 2.29 (1 H, dd, J = 13.6, 7.4 Hz), 2.45-2.54 (2 H, m), 3.70-3.78 (1 H, m), 4.43 (1 H, d, J = 12.0 Hz), 4.57 (1 H, d, J = 12.0 Hz), 5.74 (1 H, d, J = 5.8 Hz), 5.81 (1 H, d, J = 5.8 Hz), 7.16 (2 H, t, J = 8.9 Hz), 7.30 (2 H, dd, J = 8.3, 5.8 Hz) | 468 [M + H]+ |

Example 38 Synthesis of (1S,2R,3R,5R,6S)-2-amino-3-[(4-fluorophenyl)methoxy]-2-({[(1S)-1-[(tricyclo[3.3.1.1³,⁷]decane-1-carbonyl)oxy]ethoxy}carbonyl)bicyclo[3.1.0]hexane-6-carboxylic Acid

[Formula 82]

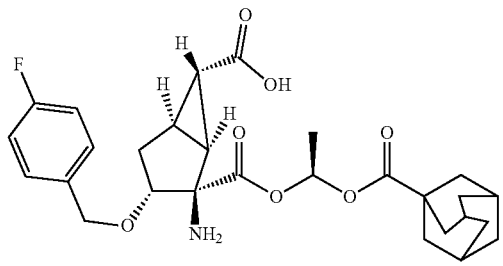

(1) Synthesis of Diethyl chloro[(1R)-3-oxocyclopentyl]propanedioate

[Formula 83]

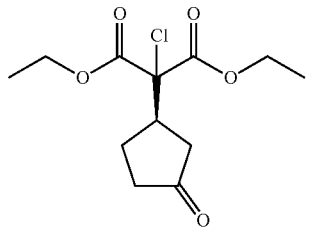

To a solution of lithium aluminum hydride (230 mg, 6.061 mmol) in THF (20 mL), a solution of (R)-(+)-1,1-bi-2-naphthol (3.72 g, 13.0 mmol) in THF (25 mL) was added at 1 to 4° C. The mixture was stirred at room temperature for 50 minutes, Molecular Sieves 4A (10.00 g), sodium carbonate (280 mg, 2.642 mmol) and diethyl 2-chloropropanedioate (130.35 g, 612 mmol) were added. The mixture was stirred at 40° C. for 30 minutes, cyclopent-2-en-1-one (60.00 g, 730.8 mmol) was added dropwise, and the resulting mixture was stirred at 40° C. for 4 hours. The insoluble was filtered at room temperature, the filtrate was concentrated under reduced pressure to obtain a mixture containing the title compound (202.39 g) (brown oil). The mixture containing the title compound was used in the next reaction without being purified. The optical purity was 90.85% ee in analysis by chiral column chromatography.
Retention time: (R) form; 6.58 min, (S) form; 15.38 min (CHIRAL PAK AY-3, flow rate: 1.0 mL/min, n-Hexane/EtOH=90/10)
1H NMR (400 MHz, CHLOROFORM-d) δ ppm 1.24-1.37 (6H, m), 1.88-2.07 (1H, m), 2.12-2.30 (2H, m), 2.32-2.46 (2H, m), 2.47-2.58 (1H, m), 3.16-3.32 (1H, m), 4.22-4.40 (4H, m)
MS m/z: 277 [M+H]+

(2) Synthesis of Ethyl (1S,5R,6S)-2-oxobicyclo[3.1.0]hexane-6-carboxylate

[Formula 84]

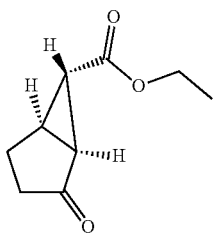

To a solution in N-methyl-2-pyrrolidinone (630 g) of the compound (202.39 g, 612 mmol) obtained in Example 38(1), lithium chloride (51.89 g, 1.224 mol) and acetic acid (36.75 g, 612 mmol) were added at 7 to 12° C., the mixture was stirred at 125° C. for 4 hours. The reaction solution was cooled to room temperature, and toluene and 10% saline were added, followed by liquid-liquid separation. The organic layer was washed twice with 10% saline. The organic layer was dried over anhydrous sodium sulfate and then filtered. The filtrate was concentrated under reduced pressure, followed by azeotropy twice using IPA. IPA (30 mL) was added to the residue, and the mixture was heated to 50° C. The heating of the mixed solution was stopped. Then, n-heptane (30 mL) was added, and the mixture was cooled with ice with stirring. The precipitating solids were collected by filtration. The solids were washed with an ice-cooled mixed solvent of IPA and n-heptane (1/1, 45 mL) and then dried by aeration using nitrogen to obtain the title compound (53.87 g) as a single enantiomer (light brown solid). The optical purity was >99% ee in analysis by chiral column chromatography. The spectrum data was confirmed to be consistent with that of a compound obtained by a documented method (see J. Med. Chem., 2000, 43, 4893-4909). Retention time: (1S,5R,6S) form; 8.52 min, (1R,5S,6R) form; 9.87 min (CHIRAL PAK AY-3, flow rate: 1.0 mL/min, n-Hexane/EtOH=90/10).
1H NMR (400 MHz, CHLOROFORM-d) δ ppm 1.27 (3H, t, J=7.1 Hz), 1.99-2.18 (4H, m), 2.19-2.26 (1H, m), 2.27-2.31 (1H, m), 2.49-2.54 (1H, m), 4.16 (2H, q, J=7.1 Hz)
MS m/z: 169[M+H]+

(3) Synthesis of Ethyl (1S,5R,6S)-2-[(trimethylsilyl)oxy]bicyclo[3.1.0]hex-2-ene-6-carboxylate

[Formula 85]

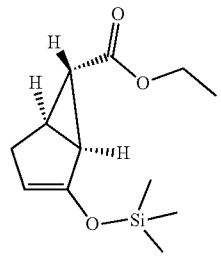

To a solution in toluene (23.1 mL) of ethyl (1S,5R,6S)-2-oxobicyclo[3.1.0]hexane-6-carboxylate (5.0 g, 29.73 mmol) obtained in Example 38(2), triethylamine (6.22 mL, 44.59 mmol) and trimethylsilyl triflate (7.93 g, 35.67 mmol) were added dropwise under cooling with ice, and the mixture was stirred for 1 hour. Water (60 mL) was added, and the mixture was stirred for 30 minutes. After separation between organic and aqueous layers, the obtained organic layer was washed with a saturated aqueous solution of sodium bicarbonate (20 mL) and brine (20 mL) in this order. The organic layer was dried over anhydrous sodium sulfate and then filtered. The filtrate was concentrated under reduced pressure to obtain the title compound (9.91 g, 28.7 mmol). The compound was used directly in the next reaction without being further purified.
¹H NMR (400 MHz, CHLOROFORM-d) δ ppm 0.22 (9H, s), 1.21-1.27 (3H, m), 2.08-2.19 (1H, m), 2.20-2.28 (1H, m), 2.28-2.41 (2H, m), 2.52-2.66 (1H, m), 4.11 (2H, q, J=7.2 Hz), 4.30-4.39 (1H, m)

(4) Synthesis of Ethyl (1S,3R,5R,6S)-3-hydroxy-2-oxobicyclo[3.1.0]hexane-6-carboxylate

[Formula 86]

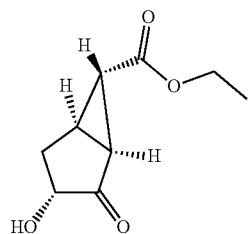

To a suspension of methyltrioxorhenium(VII) (35.8 mg, 0.144 mmol) in acetonitrile (28.7 mL) as cooled with ice water, acetic acid (173 mg, 2.87 mmol), pyridine (68.2 mg, 0.86 mmol) and an aqueous solution of 30% hydrogen peroxide (4.99 mL, 48.9 mmol) were added dropwise. A solution in acetonitrile (5.0 mL) of ethyl (1S,5R,6S)-2-[(trimethylsilyl)oxy]bicyclo[3.1.0]hex-2-ene-6-carboxylate (6.91 g, 28.7 mmol) obtained in Example 38(3) was added dropwise. The mixture was stirred at room temperature for 1 hour. Methyltrioxorhenium(VII) (17.9 mg, 0.0719 mmol)

was added, and the mixture was stirred at room temperature for 1 hour. A solution of sodium carbonate (609 mg, 5.75 mmol) in water (5.0 mL) and a solution of sodium thiosulfate pentahydrate (12.5 g, 50.3 mmol) in water (50 mL) were added under ice water, and the mixture was stirred for 10 minutes. The reaction mixture was extracted with ethyl acetate (100 mL) twice. Anhydrous sodium sulfate was added to the obtained organic layer, and the mixture was left standing at room temperature for 14 hours. After filtration, the filtrate was concentrated under reduced pressure. Isopropyl ether (50 mL) was added to the residue, and the mixture was stirred. The precipitating solids were collected by filtration to obtain the title compound (3.26 g) (colorless solid).

1H NMR (400 MHz, CHLOROFORM-d) δ ppm 1.22-1.33 (3H, m), 1.94-2.11 (1H, m), 2.20-2.27 (1H, m), 2.33-2.39 (1H, m), 2.48-2.56 (1H, m), 2.61-2.69 (1H, m), 3.90-4.02 (1H, m), 4.12-4.22 (3H, m)

MS m/z: 185[M+H]+

(5) Synthesis of Ethyl (1S,3R,5R,6S)-3-[(4-fluorophenyl)methoxy]-2-oxobicyclo[3.1.0]hexane-6-carboxylate

[Formula 87]

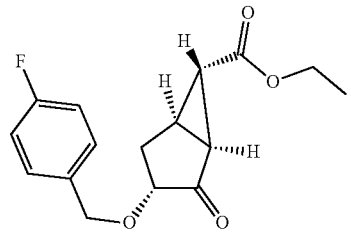

To a solution in tetrahydropyran (3.0 mL) of ethyl (1S,3R,5R,6S)-3-hydroxy-2-oxobicyclo[3.1.0]hexane-6-carboxylate (0.53 g, 2.88 mmol) obtained in Example 38(4) and (4-fluorophenyl)methyl 2,2,2-trichloroethanimidate (1.25 g, 4.60 mmol), trifluoromethanesulfonic acid (0.065 mL, 0.575 mmol) was added dropwise under cooling with ice, and the mixture was stirred for 1 hour. Water was added to the reaction solution, followed by extraction with ethyl acetate. Then, the organic layer was washed with brine. The obtained organic layer was dried over anhydrous sodium sulfate and filtered. The filtrate was concentrated under reduced pressure. The obtained residue was purified by silica gel column chromatography (Biotage SNAP Ultra 50 g, hexane:ethyl acetate=100:0 to 35:65) to obtain the title compound (0.59 g) (colorless oil).

1H NMR (400 MHz, CHLOROFORM-d) δ ppm 1.23-1.29 (3H, m), 2.06-2.20 (2H, m), 2.24-2.35 (1H, m), 2.40-2.53 (2H, m), 3.76 (1H, t, J=8.3 Hz), 4.08-4.18 (2H, m), 4.56 (1H, d, J=11.6 Hz), 4.83 (1H, d, J=11.7 Hz), 6.97-7.06 (2H, m), 7.31 (2H, t, J=6.1 Hz)

MS m/z: 315 [M+Na]+

(6) Synthesis of Ethyl (1S,3R,5R,6S)-3-[(4-fluorophenyl)methoxy]-2-{[(R)-2-methylpropane-2-sulfinyl]imino}bicyclo[3.1.0]hexane-6-carboxylate

[Formula 88]

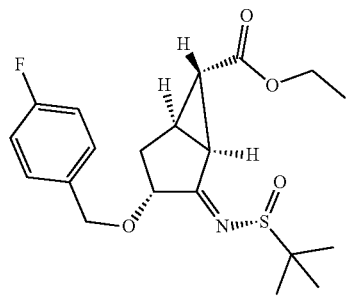

To a solution in tetrahydrofuran (6.8 mL) of ethyl (1S,3R,5R,6S)-3-[(4-fluorophenyl)methoxy]-2-oxobicyclo[3.1.0]hexane-6-carboxylate (1.00 g, 3.42 mmol) obtained in Example 38(5) and (R)-(+)-2-methyl-2-propanesulfinamide (0.83 g, 6.84 mmol), titanium(IV) ethoxide (2.12 mL, 10.26 mmol) was added at room temperature, and the mixture was stirred at 70° C. for 2 hours. A saturated aqueous solution of sodium bicarbonate was added, followed by extraction with chloroform. The obtained organic layer was dried over anhydrous magnesium sulfate and filtered. The filtrate was concentrated under reduced pressure. The obtained residue was purified by silica gel column chromatography (Biotage SNAP Ultra 50 g, hexane:ethyl acetate=100:0 to 30:70) to obtain the title compound (0.829 g) (colorless oil).

1H NMR (400 MHz, CHLOROFORM-d) δ ppm 1.14-1.31 (12H, m), 1.81-1.87 (1H, m), 2.02-2.09 (1H, m), 2.33-2.48 (2H, m), 3.64-3.69 (1H, m), 3.97 (1H, t, J=7.9 Hz), 4.08-4.17 (2H, m), 4.49-4.62 (1H, m), 4.92 (1H, d, J=11.7 Hz), 6.99-7.05 (2H, m), 7.24-7.30 (2H, m)

MS m/z: 396 [M+H]+

(7) Synthesis of Ethyl (1S,3R,5R,6S)-2-cyano-3-[(4-fluorophenyl)methoxy]-2-{[(R)-2-methylpropane-2-sulfinyl]amino}bicyclo[3.1.0]hexane-6-carboxylate

[Formula 89]

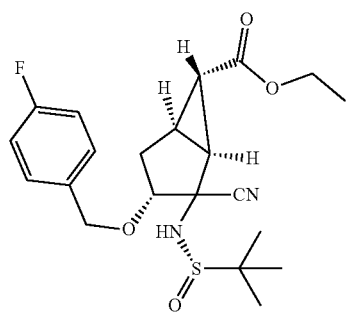

To a solution in tetrahydrofuran (4.2 mL) of ethyl (1S,3R,5R,6S)-3-[(4-fluorophenyl)methoxy]-2-{[(R)-2-methylpropane-2-sulfinyl]imino}bicyclo[3.1.0]hexane-6-carboxylate (0.83 g, 2.09 mmol) obtained in Example 38(6), cesium fluoride (1.59 g, 10.5 mmol) and trimethylsilyl cyanide (0.623 g, 6.28 mmol) were added under cooling with ice, and the mixture was stirred for 2 hours. A saturated aqueous solution of sodium bicarbonate was added, followed by extraction with chloroform. The organic layer was separated and then concentrated under reduced pressure. A mixed solution of hexane:ethyl acetate=9:1 was added to the residue, and the mixture was stirred. Then, the precipitate was collected by filtration to obtain the title compound (0.77 g) (colorless solid).

1H NMR (400 MHz, CHLOROFORM-d) δ ppm 1.19 (9H, s), 1.24 (3H, t, J=7.2 Hz), 1.69 (1H, t, J=3.0 Hz), 2.06-2.17 (2H, m), 2.25-2.33 (1H, m), 2.51 (1H, dd, J=6.6, 2.9 Hz), 3.48-3.59 (2H, m), 4.06-4.16 (2H, m), 4.52-4.63 (2H, m), 7.05 (2H, t, J=8.7 Hz), 7.31-7.37 (2H, m)

MS m/z: 445 [M+Na]+

(8) Synthesis of Ethyl (1S,2S,3R,5R,6S)-2-amino-2-cyano-3-[(4-fluorophenyl)methoxy]bicyclo[3.1.0]hexane-6-carboxylate

[Formula 90]

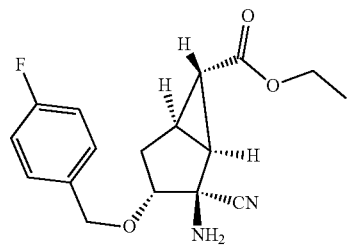

To a solution in tetrahydrofuran (1.8 mL) of ethyl (1S,3R,5R,6S)-2-cyano-3-[(4-fluorophenyl)methoxy]-2-{[(R)-2-methylpropane-2-sulfinyl]amino}bicyclo[3.1.0]hexane-6-carboxylate (0.77 g, 1.81 mmol) obtained in Example 38(7), a 2 mol/L solution of hydrochloric acid in ethanol (4.5 mL, 9.00 mmol) was added under cooling with ice, and the mixture was stirred at room temperature for 4 hours. A saturated aqueous solution of sodium bicarbonate was added, followed by extraction with chloroform. Aqueous and organic layers were separated, and the obtained organic layer was concentrated under reduced pressure. Isopropyl ether was added to the residue, and the mixture was stirred to obtain the title compound (0.51 g) (colorless solid).

1H NMR (400 MHz, CHLOROFORM-d) δ ppm 1.24 (3H, t, J=7.2 Hz), 1.75 (1H, t, J=3.1 Hz), 1.92-2.11 (4H, m), 2.27-2.34 (2H, m), 3.34 (1H, dd, J=9.1, 6.7 Hz), 4.07-4.15 (2H, m), 4.51 (1H, d, J=11.9 Hz), 4.60 (1H, d, J=12.0 Hz), 7.04 (2H, t, J=8.7 Hz), 7.31 (2H, dd, J=8.4, 5.5 Hz)

MS m/z: 319 [M+H]+

(9) Synthesis of (1S,2R,3R,5R,6S)-2-amino-3-[(4-fluorophenyl)methoxy]bicyclo[3.1.0]hexane-2,6-dicarboxylic Acid (Compound No. II-15)

[Formula 91]

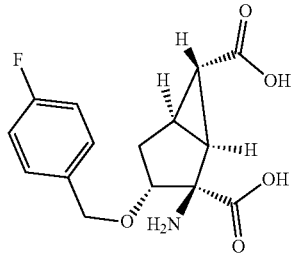

To a solution of sodium hydroxide (1.47 g, 7.36 mmol) in water (5.9 mL), an aqueous solution of 30% hydrogen peroxide (0.081 mL, 0.79 mmol) and a solution in dimethyl sulfoxide (0.53 mL) of ethyl (1S,2S,3R,5R,6S)-2-amino-2-cyano-3-[(4-fluorophenyl)methoxy]bicyclo[3.1.0]hexane-6-carboxylate (0.16 g, 0.53 mmol) obtained in Example 38(8) were added dropwise under cooling with ice. The temperature was raised to room temperature, and the mixture was stirred for 1 hour. The temperature was raised to 100° C., and the reaction mixture was stirred for 5 hours. The reaction mixture was stirred at room temperature for 16 hours. The reaction mixture was adjusted to pH=ca. 1 with 4 M hydrochloric acid, stirred for 1 hour, and then concentrated under reduced pressure. The residue was purified by preparative HPLC, and a fraction containing the compound of interest was concentrated under reduced pressure. EtOH was added to the solidified residue, and the mixture was stirred. Then, the precipitate was collected by filtration to obtain the title compound (Compound No. II-15) (0.046 g) (colorless solid).

1H NMR (400 MHz, DMSO-d6) δ ppm 1.65-1.73 (1H, m), 1.73-1.81 (1H, m), 1.85 (1H, dd, J=7.2, 2.8 Hz), 2.05-2.20 (2H, m), 3.42-3.71 (1H, m), 4.32 (1H, d, J=11.5 Hz), 4.48 (1H, d, J=11.4 Hz), 7.07-7.18 (2H, m), 7.34 (2H, dd, J=8.6, 5.7 Hz)

MS m/z: 310 [M+H]+

(10) Synthesis of (1S,2R,3R,5R,6S)-3-[(4-fluorophenyl)methoxy]-2-({[(prop-2-en-1-yl)oxy]carbonyl}amino)bicyclo[3.1.0]hexane-2,6-dicarboxylic Acid

[Formula 92]

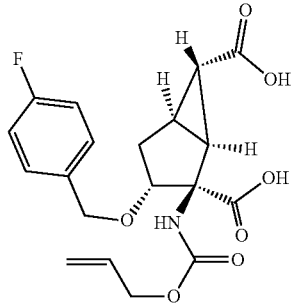

To a mixture of (1S,2R,3R,5R,6S)-2-amino-3-[(4-fluorophenyl)methoxy]bicyclo[3.1.0]hexane-2,6-dicarboxylic acid (0.49 mg, 1.58 mmol) obtained in Example 38(9), 1,4-dioxane (3.2 mL) and a saturated aqueous solution of sodium bicarbonate (5.6 mL), allyl chloroformate (0.34 mL, 3.17 mmol) was added dropwise at room temperature, and the mixture was stirred for 3 hours. Water and ethyl acetate were added, and the mixture was stirred for 10 minutes. Then, organic and aqueous layers were separated, and the obtained aqueous layer was adjusted to pH 1 by the addition of 2 M hydrochloric acid, followed by extraction with ethyl acetate. The organic layer was dried over anhydrous sodium sulfate, then filtered, and concentrated under reduced pressure to obtain a mixture containing the title compound (0.53 g) (amorphous). The mixture was used in the next reaction without being further purified.

MS m/z: 394 [M+H]+

(11) Synthesis of (1S,2R,3R,5R,6S)-3-[(4-fluorophenyl)methoxy]-6-{[(prop-2-en-1-yl)oxy]carbonyl}-2-({[(prop-2-en-1-yl)oxy]carbonyl}amino)bicyclo[3.1.0]hexane-2-carboxylic Acid

[Formula 93]

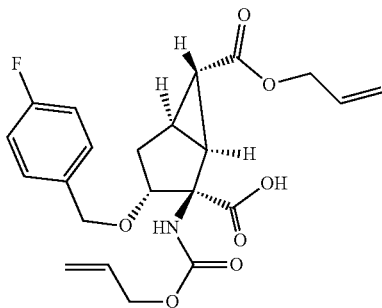

To a solution in tetrahydrofuran (0.64 mL) of (1S,2R,3R,5R,6S)-3-[(4-fluorophenyl)methoxy]-2-({[(prop-2-en-1-yl)oxy]carbonyl}amino)bicyclo[3.1.0]hexane-2,6-dicarboxylic acid (0.050 g, 0.12 mmol) obtained in Example 38(10), 4-dimethylaminopyridine (3.88 mg, 0.032 mmol), 4-methylmorpholine (0.021 mL, 0.19 mmol) and allyl chloroformate (0.015 mL, 0.14 mmol) were added at room temperature, and the mixture was stirred for 4 hours. A saturated aqueous solution of ammonium chloride was added, followed by extraction with chloroform. The obtained organic layer was concentrated under reduced pressure. The obtained residue was purified by silica gel column chromatography (Biotage SNAP Ultra 50 g, chloroform:methanol=100:0 to 90:10) to obtain the title compound (0.018 g) (brown amorphous).

MS m/z: 434 [M+H]+

(12) Synthesis of 6-prop-2-en-1-yl 2-[(1S)-1-{[(3R,5S)-tricyclo[3.3.1.1³,⁷]decane-1-carbonyl]oxy}ethyl] (1S,2R,3R,5R,6S)-3-[(4-fluorophenyl)methoxy]-2-({[(prop-2-en-1-yl)oxy]carbonyl}amino)bicyclo[3.1.0]hexane-2,6-dicarboxylate

[Formula 94]

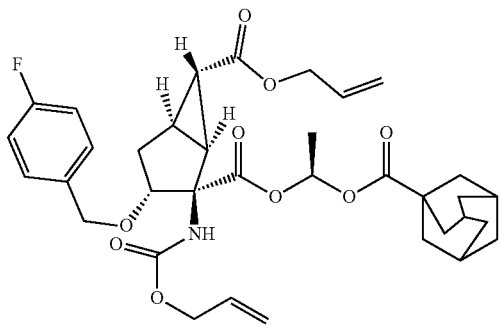

To a solution in dimethyl sulfoxide (3.3 mL) of (1S,2R,3R,5R,6S)-3-[(4-fluorophenyl)methoxy]-6-{[(prop-2-en-1-yl)oxy]carbonyl}-2-({[(prop-2-en-1-yl)oxy]carbonyl} amino)bicyclo[3.1.0]hexane-2-carboxylic acid (0.14 g, 0.33 mmol) obtained in Example 38(11), potassium carbonate (0.067 g, 0.48 mmol) was added at room temperature, and the mixture was stirred for 10 minutes. Then, (1R)-1-chloroethyl tricyclo[3.3.1.1³,⁷]decane-1-carboxylate (0.16 g, 0.65 mmol) was added, and the mixture was stirred for 16 hours. The reaction mixture was diluted with ethyl acetate and washed with a saturated aqueous solution of ammonium chloride and brine. The obtained residue was purified by silica gel column chromatography (Biotage SNAP Ultra 10 g, hexane:ethyl acetate=95:5 to 30:70) to obtain the title compound (0.15 g) (pale yellow oil).

1H NMR (400 MHz, CHLOROFORM-d) δ ppm 1.48 (3H, d, J=5.4 Hz), 1.55 (2H, d, J=4.4 Hz), 1.62-1.75 (6H, m), 1.82-1.91 (6H, m), 1.95-2.18 (5H, m), 2.23-2.33 (1H, m), 2.57 (1H, dd, J=6.9, 3.0 Hz), 4.39-4.62 (6H, m), 5.15-5.36 (5H, m), 5.83-5.95 (2H, m), 6.91 (1H, q, J=5.4 Hz), 6.99-7.06 (2H, m), 7.20-7.25 (2H, m)

MS m/z: 662 [M+Na]+

Example 38 Synthesis of (1S,2R,3R,5R,6S)-2-amino-3-[(4-fluorophenyl)methoxy]-2-({(1S)-1-[(tricyclo[3.3.1.1³,⁷]decane-1-carbonyl)oxy]ethoxy}carbonyl)bicyclo[3.1.0]hexane-6-carboxylic Acid

[Formula 95]

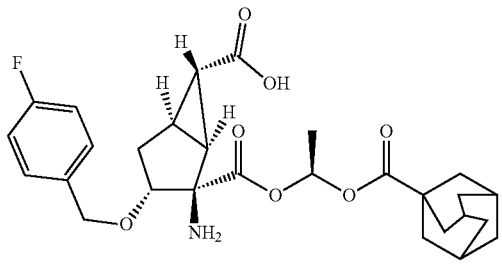

To a solution in chloroform (0.73 mL) of 6-prop-2-en-1-yl 2-[(1S)-1-{[(3R,5S)-tricyclo[3.3.1.1³,⁷]decane-1-carbonyl]oxy}ethyl] (1S,2R,3R,5R,6S)-3-[(4-fluorophenyl)meth- oxy]-2-({[(prop-2-en-1-yl)oxy]carbonyl}amino)bicyclo[3.1.0]hexane-2,6-dicarboxylate (0.14 g, 0.21 mmol) obtained in Example 38(12), 1,3-dimethylbarbituric acid (0.034 g, 0.22 mmol) and tetrakis(triphenylphosphine)palladium(0) (2.5 mg, 0.002 mmol) were added at room temperature, and the mixture was stirred for 3 hours. The reaction mixture was concentrated under reduced pressure. The obtained residue was purified by silica gel column chromatography (YMC C18 12 g, water:acetonitrile=95:5 to 5:95). A fraction containing the title compound was concentrated. Isopropyl ether was added to the obtained residue, and the mixture was stirred. The precipitate was collected by filtration to obtain the title compound (0.021 g) (colorless solid).

1H NMR (400 MHz, CHLOROFORM-d) δ ppm 1.46 (3H, d, J=5.4 Hz), 1.64-1.76 (7H, m), 1.87 (6H, s), 1.96-2.05 (5H, m), 2.10-2.19 (1H, m), 2.23-2.33 (1H, m), 3.59-3.69 (1H, m), 4.42 (2H, s), 6.88 (1H, q, J=5.4 Hz), 7.00 (2H, t, J=8.1 Hz), 7.20 (2H, t, J=6.4 Hz)

MS m/z: 514 [M−H]−

Example 39 Synthesis of (1S,2R,3R,5R,6S)-2-amino-3-[(4-fluorophenyl)methoxy]-2-({(1R)-1-[({[(1R,2S,5R)-5-methyl-2-(propan-2-yl)cyclohexyl]oxy}carbonyl)oxy]ethoxy}carbonyl)bicyclo[3.1.0]hexane-6-carboxylic Acid

[Formula 96]

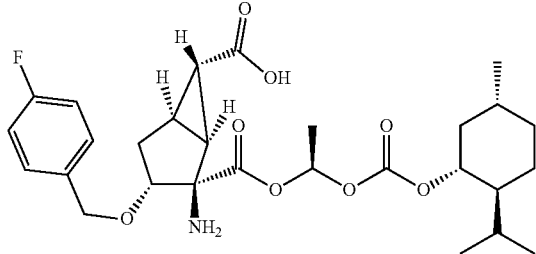

The title compound (Example No. 39) (0.010 g) was obtained (colorless solid) by the same procedure as in Example 38(12) and Example 38(13) using (1S,2R,3R,5R,6S)-3-[(4-fluorophenyl)methoxy]-6-{[(prop-2-en-1-yl)oxy]carbonyl}-2-({[(prop-2-en-1-yl)oxy]carbonyl}amino)bicyclo[3.1.0]hexane-2-carboxylic acid (0.20 g, 0.46 mmol) obtained in Example 38(11) and (1R)-1-chloroethyl (1R,2S,5R)-5-methyl-2-(propan-2-yl)cyclohexyl carbonate (0.29 g, 1.11 mmol).

1H NMR (400 MHz, DMSO-d6) δ ppm 0.67-1.13 (13H, m), 1.28-1.52 (3H, m), 1.56-1.77 (4H, m), 1.77-2.03 (4H, m), 2.17-2.29 (2H, m), 3.45-3.66 (1H, m), 4.33-4.54 (3H, m), 6.63-6.69 (1H, m), 7.11-7.37 (4H, m)

MS m/z: 534 [M−H]−

Reference Example 1 Synthesis of ((1S,2R,3R,5R,6S)-2-amino-3-[(4-fluorophenyl)methoxy]-6-({(1R)-1-[(tricyclo[3.3.1.1³,⁷]decane-1-carbonyl)oxy]ethoxy}carbonyl)bicyclo[3.1.0]hexane-2-carboxylic Acid

[Formula 97]

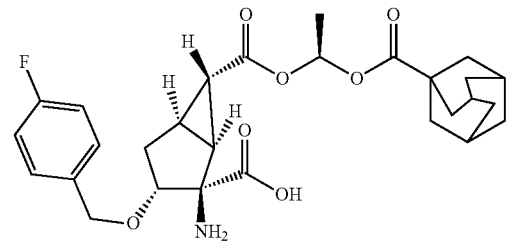

(1) Synthesis of (1S,2R,3R,5R,6S)-3-[(4-fluorophenyl)methoxy]-5'-oxo-3'-{[(prop-2-en-1-yl)oxy]carbonyl}spiro[bicyclo[3.1.0]hexane-2,4'-[1,3]oxazolidine]-6-carboxylic Acid

[Formula 98]

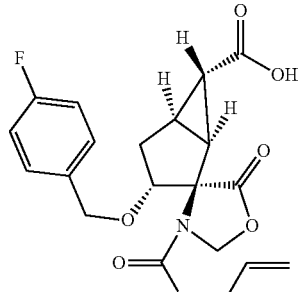

To a solution in toluene (2.3 mL) of (1S,2R,3R,5R,6S)-3-[(4-fluorophenyl)methoxy]-2-({[(prop-2-en-1-yl)oxy]carbonyl}amino)bicyclo[3.1.0]hexane-2,6-dicarboxylic acid (0.096 g, 0.24 mmol) obtained in Example 38(10), 37% formalin (0.06720 mL, 0.8968 mmol) and toluenesulfonic acid monohydrate (2.32 mg, 0.012 mmol) were added, and the mixture was stirred at 120° C. for 4 hours and then further stirred at room temperature for 16 hours. The reaction mixture was concentrated under reduced pressure to obtain a mixture containing the title compound (0.19 g) (pale yellow amorphous). The mixture was used in the next reaction without further purification.

MS m/z: 404 [M−H]−

(2) Synthesis of 3'-prop-2-en-1-yl 6-{(1R)-1-[(tricyclo[3.3.1.1^{3,7}]decane-1-carbonyl)oxy]ethyl}(1S,2R,3R,5R,6S)-3-[(4-fluorophenyl)methoxy]-5'-oxo-3'H-spiro[bicyclo[3.1.0]hexane-2,4'-[1,3]oxazolidine]-3',6-dicarboxylate

[Formula 99]

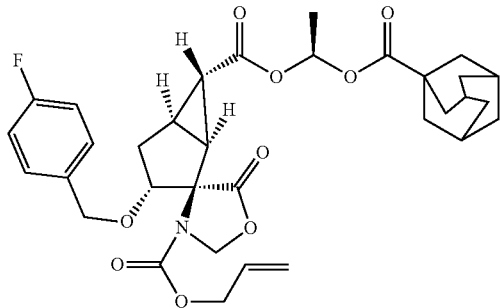

To a solution in dimethyl sulfoxide (1.6 mL) of (1S,2R,3R,5R,6S)-3-[(4-fluorophenyl)methoxy]-5'-oxo-3'-{[(prop-2-en-1-yl)oxy]carbonyl}spiro[bicyclo[3.1.0]hexane-2,4'-[1,3]oxazolidine]-6-carboxylic acid (0.19 g, 0.476 mmol) obtained in (1), potassium carbonate (0.714 mmol) was added at room temperature, and the mixture was stirred for 10 minutes. Then, (1R)-1-chloroethyl tricyclo[3.3.1.1^{3,7}]decane-1-carboxylate (0.16 g, 0.65 mmol) was added, and the mixture was stirred for 16 hours. The reaction mixture was diluted with ethyl acetate and washed with a saturated aqueous solution of ammonium chloride and brine. The obtained residue was purified by silica gel column chromatography (Biotage SNAP Ultra 10 g, hexane:ethyl acetate=95:5 to 50:50) to obtain a mixture containing the title compound (0.088 g) (brown oil).

1H NMR (400 MHz, CHLOROFORM-d) δ ppm 1.41-1.47 (3H, m), 1.63-2.10 (15H, m), 2.17-2.45 (5H, m), 4.01-4.21 (1H, m), 4.21-4.39 (1H, m), 4.45-4.62 (3H, m), 5.12-5.36 (4H, m), 5.84-5.94 (1H, m), 6.75-6.89 (1H, m), 6.90-7.08 (2H, m), 7.11-7.24 (2H, m)

(3) Synthesis of ((1S,2R,3R,5R,6S)-2-amino-3-[(4-fluorophenyl)methoxy]-6-({(1R)-1-[(tricyclo[3.3.1.1^{3,7}]decane-1-carbonyl)oxy]ethoxy}carbonyl)bicyclo[3.1.0]hexane-2-carboxylic Acid

[Formula 100]

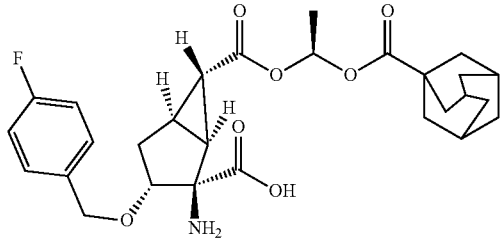

To a solution in chloroform (1.4 mL) of 3'-prop-2-en-1-yl 6-{(1R)-1-[(tricyclo[3.3.1.1^{3,7}]decane-1-carbonyl)oxy]ethyl}(1S,2R,3R,5R,6S)-3-[(4-fluorophenyl)methoxy]-5'-oxo-3'H-spiro[bicyclo[3.1.0]hexane-2,4'-[1,3]oxazolidine]-

3',6-dicarboxylate (0.088 g, 0.14 mmol) obtained in (2), 1,3-dimethylbarbituric acid (0.23 g, 0.14 mmol) and tetrakis(triphenylphosphine)palladium(0) (0.2 mg, 0.0001 mmol) were added at room temperature, and the mixture was stirred for 3 hours. The reaction solution was concentrated under reduced pressure. Then, acetonitrile (2.0 mL) was added, and the mixture was stirred at room temperature. The precipitate was collected by filtration and dried to obtain the title compound (0.014 g) (colorless solid).

1H NMR (400 MHz, DMSO-d6) δ ppm 1.38 (3H, d, J=5.4 Hz), 1.61-2.02 (18H, m), 2.07-2.20 (2H, m), 3.53-3.61 (1H, m), 4.31 (1H, d, J=11.5 Hz), 4.48 (1H, d, J=11.6 Hz), 6.64-6.70 (1H, m), 7.10-7.18 (2H, m), 7.31-7.39 (2H, m)

MS m/z: 516[M+H]+

Test 1 [$^{35}$S]GTPγS Binding Test

CHO cells stably expressing human metabotropic glutamate receptors mGluR2 and mGluR3 were cultured at 37° C. under 5% $CO_2$ using a Dulbecco's modified Eagle medium [1% proline, 1 mM sodium pyruvate, 1 mM succinic acid, 1 mM disodium succinate, 100 units/mL penicillin, 100 μg/mL streptomycin, 400 (mGluR2) or 300 (mGluR3) μg/mL hygromycin B, 2 mM L-glutamine (added just before use)] containing 10% dialyzed fetal bovine serum. The cells in a confluent state were washed with PBS(-), then dissociated using a cell scraper, and centrifuged at 1000 rpm for 5 minutes at 4° C. to recover the cells. The obtained pellet was suspended in a 20 mM HEPES buffer (pH 7.4) (mGluR2) or 20 mM HEPES buffer containing 1 mM EDTA (pH 7.4) (mGluR3), and the suspension was homogenized in a Teflon® homogenizer and then centrifuged at 48,000×g for 20 minutes at 4° C. to obtain a pellet again. The obtained pellet was subjected to two additional cycles of washing and centrifugation and then homogenized with the buffer described above to obtain a crude membrane fraction. The crude membrane fraction was diluted with a buffer for a binding test (final concentration: 20 mM HEPES, 100 mM NaCl, 10 mM $MgCl_2$, 10 μM GDP, 10 μg/mL saponin, 0.1% BSA) (mGluR2) or (final concentration: 20 mM HEPES, 1 mM EDTA, 100 mM NaCl, 10 mM $MgCl_2$, 10 μM GDP, 10 μg/mL saponin, 0.1% BSA) (mGluR3). To the crude membrane fraction containing 10 μg of membrane proteins/assay, Compounds (II)-1 to (II)-15 were each added, and the mixture was incubated at 30° C. for 20 minutes. Then, glutamate (final concentration: 20 (mGluR2) or 1 (mGluR3) μM) and [$^{35}$S]GTPγS (final concentration: 0.15 nM) were added thereto, and the mixture was incubated at 30° C. for 1 hour. The solution thus incubated was filtered by suction onto Whatman GF/C filter, and the filter was washed with 1000 μL of an ice-cooled 20 mM HEPES buffer (pH 7.4) (mGluR2) or 20 mM HEPES buffer containing 1 mM EDTA (pH 7.4) (mGluR3). A scintillation cocktail was added to the obtained filter, and the membrane binding radioactivity was measured using a liquid scintillation counter. The residual radioactivity in the absence of glutamate was defined as nonspecific binding, and the difference from the residual radioactivity in the presence of glutamate was defined as specific binding. From the percent inhibition of specific binding at varying concentrations of Compounds (II)-1 to (II)-15, an inhibition curve was obtained using nonlinear analysis. The concentrations at which Compounds (II)-1 to (II)-15 inhibited 50% of specific binding ($IC_{50}$) were calculated from the inhibition curve. The results are shown in the following Table 1.

TABLE 1

| Compound No. | mGluR2 IC$_{50}$ (nM) | mGluR3 IC$_{50}$ (nM) |
|---|---|---|
| Compound (II)-1 | 36.1 | 36.4 |
| Compound (II)-2 | 18.8 | 14.8 |
| Compound (II)-3 | 75.1 | 321 |
| Compound (II)-4 | 5.22 | 5.04 |
| Compound (II)-5 | 23.7 | 279 |
| Compound (II)-6 | 27.8 | 75.5 |
| Compound (II)-7 | 98.8 | 173 |
| Compound (II)-8 | 18.6 | 32.3 |
| Compound (II)-9 | 62.2 | 97.6 |
| Compound (II)-10 | 49.7 | 50.6 |
| Compound (II)-11 | 28.4 | 12.4 |
| Compound (II)-12 | 24.6 | 54.4 |
| Compound (II)-13 | 37.3 | 4.35 |
| Compound (II)-14 | 30.1 | 15.2 |
| Compound (II)-15 | 32.7 | 60.5 |

Test 2: Stability Test in Solution

A test to determine the stability of Inventive Compounds (I-A) or (I) in a hydrochloric acid solution (pH 1.2) and 20 mM phosphate buffer (pH 6.5) was conducted in accordance with the following method.

A compound was dissolved in a hydrochloric acid solution (pH 1.2) containing hydrochloric acid and sodium chloride or a 20 mM phosphate buffer (pH 6.5) containing disodium hydrogenphosphate, sodium dihydrogenphosphate and sodium chloride to prepare a solution with a concentration of about 50 μg/mL (near the saturated concentration when the compound was not dissolved). The solution was incubated at 37° C. for 1 hour and the compound's concentration before and after the incubation was quantified by high-performance liquid chromatography to calculate the percent residue of the compound. Compounds having low solubility were assessed as being not applicable.

The percent residues of representative compounds in the hydrochloric acid solution (pH 1.2) and the 20 mM phosphate buffer (pH 6.5) are shown in the following Table 2.

TABLE 2

| | Compound's percent residue (%) | |
|---|---|---|
| Compound No. | pH 1.2 | pH 6.5 |
| Example 1 | 109 | 103 |
| Example 2 | NA | 104 |
| Example 3 | 93 | NA |
| Example 4 | 98 | 98 |
| Example 5 | 100 | 98 |
| Example 6 | 99 | 11 |
| Example 7 | 101 | 106 |
| Example 8 | 97 | NA |
| Example 9 | 115 | 116 |
| Example 10 | 104 | 107 |
| Example 11 | 96 | 95 |
| Example 12 | 101 | 102 |
| Example 13 | 98 | 98 |
| Example 14 | 97 | 97 |
| Example 15-A | 104 | 104 |
| Example 15-B | 100 | 103 |
| Example 16-A | NA | NA |
| Example 16-B | 101 | 93 |
| Example 17-A | 104 | 97 |
| Example 17-B | 106 | 100 |
| Example 18-A | 107 | 103 |
| Example 18-B | NA | 112 |
| Example 19-A | 98 | 99 |
| Example 19-B | 100 | 106 |
| Example 20 | 106 | 100 |
| Example 21 | 101 | 98 |
| Example 22 | 96 | 94 |
| Example 23 | 101 | 100 |
| Example 24 | 95 | 96 |
| Example 25 | 98 | 99 |
| Example 26 | 97 | 94 |
| Example 27 | 100 | 101 |
| Example 28 | 100 | 99 |
| Example 29 | 102 | 103 |
| Example 30 | 100 | 102 |
| Example 31 | NA | NA |
| Example 32 | 96 | 94 |
| Example 33 | 96 | 97 |
| Example 34 | 100 | 94 |
| Example 35 | 100 | 97 |
| Example 36 | 100 | 99 |
| Example 37 | 102 | 96 |
| Example 38 | 97 | 94 |
| Example 39 | 97 | NA |

NA; Not applicable because of low solubility

As demonstrated above, Inventive Compounds were highly stable in the solutions simulating the stomach and the small intestine, so it could be assumed that they would exist as a prodrug form in the digestive tract.

Test 3: Test for Percent Formation of Compound (II)-A or (II) in Liver S9 Fractions The percent formation of Compound (II)-A or (II) in liver S9 fractions was confirmed for Inventive Compound (I-A) or (I) in accordance with the following method.

Each Inventive Compound was added to a sodium-potassium phosphate buffer (0.25 mol/L, pH 7.4) containing a liver S9 fraction (human: XenoTech, LLC/H0620.S9/Lot. 0810471, monkey: XenoTech, LLC/P2000.S9/Lot. 0910273), and the mixture was incubated (37° C.) for 15 minutes in the presence of a co-factor. The final concentration of the Inventive Compound and the protein concentration in the reaction mixture were adjusted to 1 μmol/L and 1 mg protein/mL, respectively. After the incubation, the reactions were terminated by adding the two volumes of dimethyl sulfoxide. The protein was removed by centrifugation (2150×g, 4° C., 10 min). The resulting supernatant was subjected to analysis by a liquid chromatography-tandem mass spectrometry (LC-MS/MS).

The analyte was eluted in a linear gradient mode using Shimadzu Shim-pack XR-ODS (2.2 μm, 30 mm×3.0 mm I.D.) as a separation column and 0.1% formic acid/acetonitrile solution (flow rate: 1.3 mL/min) as mobile phase. MS/MS analysis of Inventive Compound (I-A) or (I), and Compound (II)-A or (II) was performed using a Triple TOF 5600 or Triple Quad 5500 system with TurbolonSpray interface (both being products of AB SCIEX) in either positive or negative ion detection mode.

The percent formation of Compound (II)-A or (II) in the liver S9 fractions is shown in the following Table 3 with respect to Inventive Compounds.

TABLE 3

| | | Percent formation (%) of active form in liver S9 fraction | |
|---|---|---|---|
| Compound No. | active form | human | monkey |
| Example 4 | Compound (II)-1 | 88.2 | 105.3 |
| Example 7 | Compound (II)-1 | 68.1 | 108.7 |
| Example 17-A | Compound (II)-1 | 31.9 | 10.3 |
| Example 19-B | Compound (II)-1 | 40.3 | 18.7 |

TABLE 3-continued

| Compound No. | active form | Percent formation (%) of active form in liver S9 fraction | |
|---|---|---|---|
| | | human | monkey |
| Example 11 | Compound (II)-2 | 101.1 | 94.1 |
| Example 12 | Compound (II)-2 | 65.2 | 103.2 |
| Example 13 | Compound (II)-3 | 63.9 | 30.3 |
| Example 15-B | Compound (II)-3 | 23.7 | 15.3 |
| Example 18-A | Compound (II)-3 | 51.9 | 36.1 |
| Example 22 | Compound (II)-5 | 96.3 | 81.3 |
| Example 23 | Compound (II)-6 | 99.3 | 87.8 |
| Example 24 | Compound (II)-8 | 98.1 | 109.7 |
| Example 25 | Compound (II)-4 | 107.3 | 98.1 |
| Example 26 | Compound (II)-11 | 86.4 | 77.2 |
| Example 27 | Compound (II)-10 | 95.8 | 117.0 |
| Example 28 | Compound (II)-12 | 93.0 | 104.7 |
| Example 29 | Compound (II)-7 | 75.4 | 70.0 |
| Example 30 | Compound (II)-9 | 100.9 | 101.7 |
| Example 32 | Compound (II)-6 | 11.6 | 19.8 |
| Example 33 | Compound (II)-8 | 28.7 | 12.5 |
| Example 35 | Compound (II)-1 | 98.5 | 71.4 |
| Example 36 | Compound (II)-1 | 101.7 | 68.8 |
| Example 37 | Compound (II)-1 | 103.7 | 108.3 |
| Example 38 | Compound (II)-15 | 99.1 | 87.4 |

Inventive Compound (I-A) or (I) was converted to Compound (II)-A or (II), thus permitting assumption of the conversion from the prodrugs to their active forms in both the human and monkey livers.

Test 4: Measurement of Plasma Concentrations of Compound (II)-A or (II) in Monkeys Upon Oral Administration The plasma concentrations of Compound (II)-A or (II) after oral administration of Compound (II)-A or (II), and Inventive Compound (I-A) or (I) were measured in accordance with the following method.

Compound (II)-A or (II), and Inventive Compound (I-A) or (I) were orally administered to male cynomolgus monkeys (fasted condition) at a dose of 1 mg/kg in terms of Compound (II)-A or (II) (vehicle: 0.5% methyl cellulose solution; administered at 5 mL/kg).

Before the oral administration and 0.5 hours, 1 hour, 2 hours, 4 hours, 8 hours and 24 hours after the oral administration, approximately 0.6 mL of blood was taken from the forelimb cephalic vein (anticoagulant: EDTA-2K). The plasma collected by centrifugation (2000×g, 4° C., 15 min) was stored frozen at −30° C. until use for analysis. In the case of analysis, 50 μL of the plasma sample was thawed under cooling conditions with ice and after adding 200 μL of acetonitrile/methanol mixture containing an internal standard substance, the resulting mixture was stirred and centrifuged (3639×g, 4° C., 10 min) to remove the protein. The resulting supernatant was subjected to LC-MS/MS analysis. The lower limit of quantitation for Compound (II)-A or (II) was 1 ng/mL for all the samples.

The peak plasma concentration ($C_{max}$) and bioavailability (BA) data of Compound (II)-A or (II) after oral administration of representative compounds to monkeys are shown in the following Table 4. BA was calculated on the basis of the plasma concentration of Compound (II)-A or (II) after intravenous administration of Compound (II)-A or (II).

TABLE 4

| Administered compound and active form thereof | | $C_{max}$ and BA of Compound (II)-A or (II) in monkeys upon oral administration | |
|---|---|---|---|
| Administered compound | Active form | $C_{max}$ (ng/mL) | BA (%) |
| Compound (II)-1 | — | 15.3 | 5.4 |
| Compound (II)-3 | — | 29.0 | 6.3 |
| Example 4 | Compound (II)-1 | 247 | 68.6 |
| Example 11 | Compound (II)-2 | 423 | 58.2 |
| Example 13 | Compound (II)-3 | 284 | 50.0 |

The oral administration of Inventive Compound (I-A) or (I) drastically improved exposure of Compound (II)-A or (II), demonstrating an excellent prodrug effect.

INDUSTRIAL APPLICABILITY

It has been revealed that Inventive Compounds are very useful as prodrugs of Compound (II)-A or (II) which has a strong action on group 2 metabotropic glutamate receptors. Hence, Inventive Compounds or pharmaceutically acceptable salts thereof can be used as agents for prevention or treatment of conditions that are controlled by group 2 metabotropic glutamate receptor antagonists, such as mood disorders (including depression and bipolar disorder), anxiety disorder, cognitive disorders, developmental disorders, Alzheimer's disease, Parkinson's disease, movement disorders associated with muscular rigidity, sleep disorders, Huntington's chorea, eating disorders, drug dependence, epilepsy, brain infarction, cerebral ischemia, cerebral insufficiency, cerebral edema, spinal cord disorders, head trauma, inflammation and immune-related diseases.

The invention claimed is:
1. A compound represented by formula (I-A):

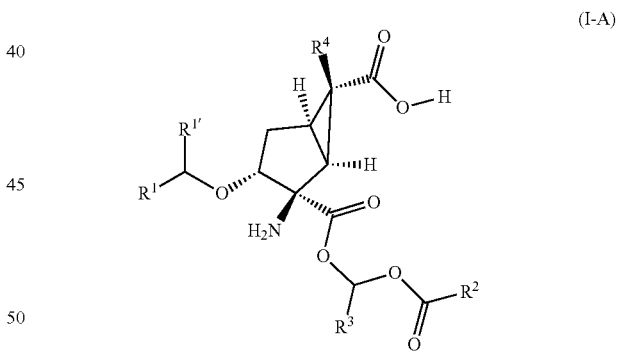

(I-A)

or pharmaceutically acceptable salt thereof,
wherein
$R^1$ represents a $C_{1-6}$ alkyl group, a heteroaryl group optionally substituted by one halogen atom, or the following formula (IIIA):

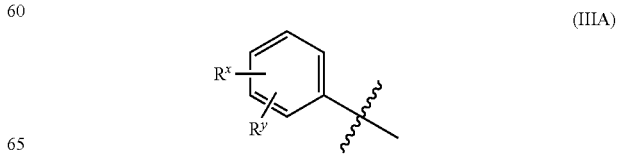

(IIIA)

where $R^x$ represents a hydrogen atom, a halogen atom, a $C_{1-6}$ alkyl group, or a $C_{1-6}$ alkoxy group, wherein the $C_{1-6}$ alkyl group and the $C_{1-6}$ alkoxy group are each optionally substituted by one to three halogen atoms, and $R^y$ represents a hydrogen atom, a fluorine atom, a $C_{1-6}$ alkyl group, or a $C_{1-6}$ alkoxy group, wherein the $C_{1-6}$ alkyl group and the $C_{1-6}$ alkoxy group are each optionally substituted by one to three halogen atoms, $R^{1'}$ represents a hydrogen atom or a $C_{1-6}$ alkyl group, or $R^1$ and $R^{1'}$ optionally form a $C_{3-6}$ cycloalkane together with the carbon atom adjacent thereto, $R^2$ represents a $C_{3-6}$ alkyl group, a $C_{3-8}$ cycloalkyl group optionally substituted by one to three $C_{1-6}$ alkyl groups, a $C_{3-8}$ cycloalkoxy group optionally substituted by one to three $C_{1-6}$ alkyl groups and optionally having a $C_{1-5}$ alkylene group crosslinking two different carbon atoms in the ring, an adamantyl group optionally substituted by one to three $C_{1-6}$ alkyl groups, or a phenyl group, $R^3$ represents a hydrogen atom or a $C_{1-6}$ alkyl group, and $R^4$ represents a hydrogen atom or a fluorine atom.

2. The compound or pharmaceutically acceptable salt thereof according to claim 1, wherein $R^4$ is a fluorine atom.

3. The compound or pharmaceutically acceptable salt thereof according to claim 2, wherein $R^1$ is an ethyl group, a 4-fluorophenyl group, a 3,4-difluorophenyl group, a 4-fluoro-3-methoxyphenyl group, a 4-(trifluoromethyl)phenyl group, a 3-fluorophenyl group, a 4-methylphenyl group, a 6-chloropyridin-2-yl group, a 6-chloropyridin-3-yl group, a 5-chloropyridin-2-yl group, or a 2-methylpropyl group, $R^{1'}$ represents a hydrogen atom or a methyl group, or $R^1$ and $R^{1'}$ optionally form a cyclopentane together with the carbon atom adjacent thereto, $R^2$ represents any structure of the following formula group (IIIB):

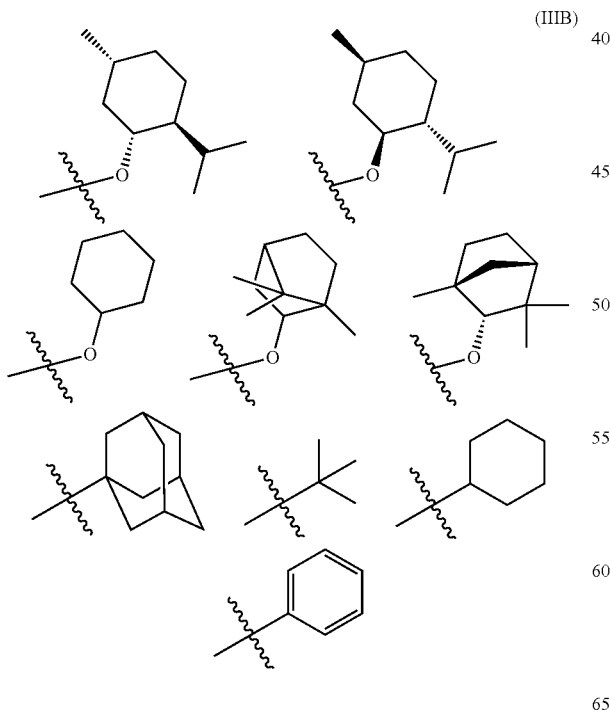

and $R^3$ is a hydrogen atom or a $C_{1-6}$ alkyl group.

4. The compound or pharmaceutically acceptable salt thereof according to claim 1, wherein $R^4$ is a hydrogen atom.

5. The compound or pharmaceutically acceptable salt thereof according to claim 4, wherein $R^1$ is an ethyl group, a 4-fluorophenyl group, a 3,4-difluorophenyl group, a 4-fluoro-3-methoxyphenyl group, a 4-(trifluoromethyl)phenyl group, a 3-fluorophenyl group, a 4-methylphenyl group, a 6-chloropyridin-2-yl group, a 6-chloropyridin-3-yl group, a 5-chloropyridin-2-yl group or a 2-methylpropyl, $R^{1'}$ represents a hydrogen atom or a methyl group, or $R^1$ and $R^{1'}$ optionally form a cyclopentane together with the carbon atom adjacent thereto, $R^2$ represents any structure of the following formula group (IIIB):

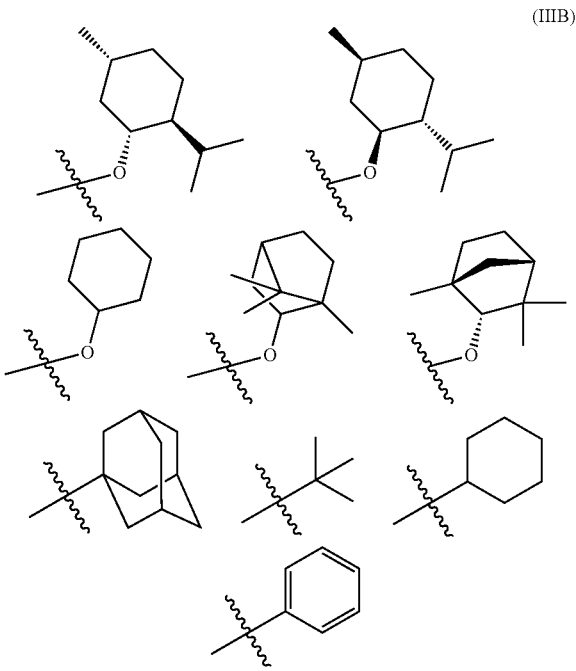

and $R^3$ is a hydrogen atom or a $C_{1-6}$ alkyl group.

6. The compound or pharmaceutically acceptable salt thereof according to claim 4, wherein $R^1$ is a 4-fluorophenyl group or a 3,4-difluorophenyl group.

7. The compound or pharmaceutically acceptable salt thereof according to claim 4, wherein $R^1$ is a 4-fluorophenyl group, $R^{1'}$ is a hydrogen atom, and $R^2$ represents any structure of the following formula group (IIIb):

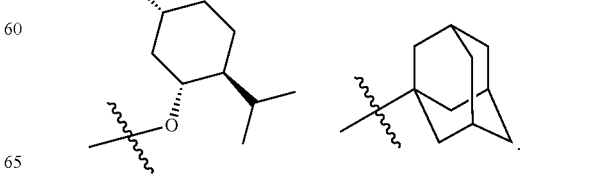

8. The compound or pharmaceutically acceptable salt thereof according to claim 4, wherein $R^3$ is a methyl group.

9. A compound or pharmaceutically acceptable salt thereof represented by formula (I):

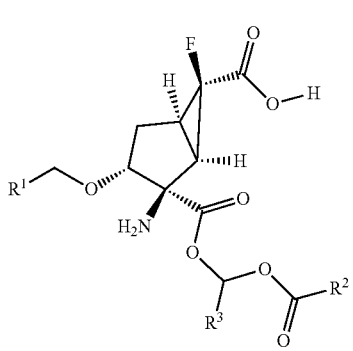

or pharmaceutically acceptable salt thereof,
wherein
$R^1$ represents an ethyl group, a 4-fluorophenyl group or a 3,4-difluorophenyl group,
$R^2$ represents any structure of the following formula group (IIIa'):

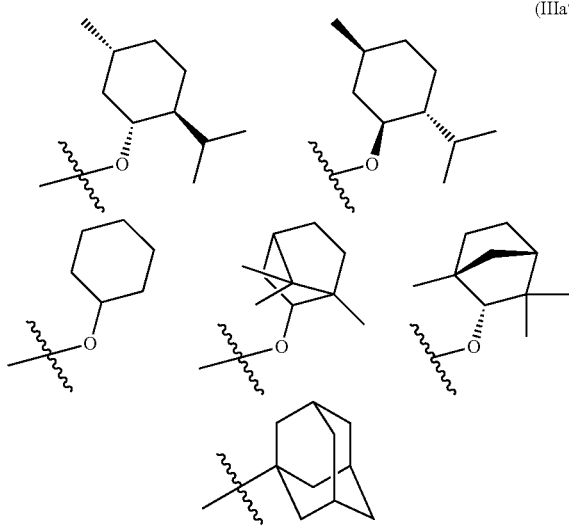

and
$R^3$ represents a hydrogen atom or a $C_{1-6}$ alkyl group.

10. The compound or pharmaceutically acceptable salt thereof according to claim 9, wherein $R^2$ represents any structure of the following formula group (111b):

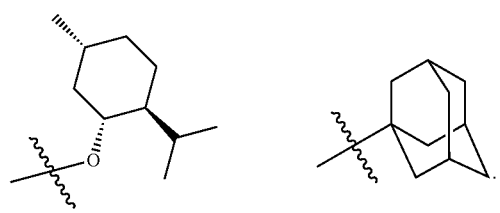

11. The compound or pharmaceutically acceptable salt thereof according to claim 9, wherein $R^3$ is a methyl group.

12. The compound or pharmaceutically acceptable salt thereof according to claim 1, wherein the compound or pharmaceutically acceptable salt thereof is any of the following compounds:

(1R,2R,3R,5R,6R)-2-amino-6-fluoro-3-[(4-fluorophenyl) methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-6-fluoro-3-[(4-fluorophenyl) methoxy]-2-({[(tricyclo[3.3.1.1$^{3,7}$]decane-1-carbonyl) oxy]methoxy}carbonyl)bicyclo[3.1.0]hexane-6-carboxylic acid, (1R,2R,3R,5R,6R)-2-amino-3-[(3,4-difluorophenyl) methoxy]-6-fluoro-2-({(1S)-1 [(tricyclo[3.3.1.1$^{3,7}$]decane-1-carbonyl)oxy]ethoxy}carbonyl)bicyclo[3.1.0] hexane-6-carboxylic acid, (1R,2R,3R,5R,6R)-2-amino-3-[(3,4-difluorophenyl) methoxy]-6-fluoro-2-({[(tricyclo[3.3.1.1$^{3,7}$]decane-1-carbonyl)oxy]methoxy}carbonyl)bicyclo[3.1.0] hexane-6-carboxylic acid, (1R,2R,3R,5R,6R)-2-amino-6-fluoro-2-({(1R)-1-[({[(1R,2S,5R)-5-methyl-2-(propan-2-yl)cyclohexyl] oxy}carbonyl)oxy]ethoxy}carbonyl)-3-propoxybicyclo[3.1.0]hexane-6-carboxylic acid, (1R,2R,3R,5R,6R)-2-amino-6-fluoro-2-({1-[({[(1S,2R,5S)-5-methyl-2-(propan-2-yl)cyclohexyl] oxy}carbonyl)oxy]ethoxy}carbonyl)-3-propoxybicyclo[3.1.0]hexane-6-carboxylic acid, (1R,2R,3R,5R,6R)-2-amino-6-fluoro-3-[(4-fluorophenyl) methoxy]-2-({1-[({[(1S,2R,4S)-1,7,7-trimethylbicyclo [2.2.1]heptan-2-yl]oxy}carbonyl)oxy] ethoxy}carbonyl)bicyclo[3.1.0]hexane-6-carboxylic acid, (1R,2R,3R,5R,6R)-2-amino-6-fluoro-3-propoxy-2-({1-[({[(1S,2R,4S)-1,7,7-trimethylbicyclo[2.2.1]heptan-2-yl]oxy}carbonyl)oxy]ethoxy}carbonyl)bicyclo[3.1.0] hexane-6-carboxylic acid, (1R,2R,3R,5R,6R)-2-amino-6-fluoro-3-[(4-fluorophenyl) methoxy]-2-({1-[({[(1R,2S,4R)-1,7,7-trimethylbicyclo [2.2.1]heptan-2-yl]oxy}carbonyl)oxy] ethoxy}carbonyl)bicyclo[3.1.0]hexane-6-carboxylic acid, (1R,2R,3R,5R,6R)-2-amino-6-fluoro-2-({(1S)-1-[(tricyclo[3.3.1.1$^{3,7}$]decane-1-carbonyl)oxy] ethoxy}carbonyl)-3{[4-(trifluoromethyl)phenyl] methoxy}bicyclo[3.1.0]hexane-6-carboxylic acid, (1R,2R,3R,5R,6R)-2-amino-6-fluoro-3-[(3-fluorophenyl) methoxy]-2-({(1S)-1-[(tricyclo[3.3.1.1$^{3,7}$]decane-1-carbonyl)oxy]ethoxy}carbonyl)bicyclo[3.1.0]hexane-6-carboxylic acid, (1R,2R,3R,5R,6R)-2-amino-3-[(6-chloropyridin-2-yl) methoxy]-6-fluoro-2-({(1S)-1-[(tricyclo[3.3.1.1$^{3,7}$]decane-1-carbonyl)oxy]ethoxy}carbonyl)bicyclo[3.1.0] hexane-6-carboxylic acid, (1R,2R,3R,5R,6R)-2-amino-6-fluoro-3-[(1R)-1-(4-fluoro-3-methoxyphenyl)ethoxy]-2-({(1S)-1-[(tricyclo [3.3.1.1$^{3,7}$]decane-1-carbonyl)oxy]ethoxy}carbonyl) bicyclo[3.1.0]hexane-6-carboxylic acid, (1R,2R,3R,5R,6R)-2-amino-3-[(5-chloropyridin-2-yl) methoxy]-6-fluoro-2-({(1S)-1-[(tricyclo[3.3.1.1$^{3,7}$]decane-1-carbonyl)oxy]ethoxy}carbonyl)bicyclo[3.1.0] hexane-6-carboxylic acid, (1R,2R,3R,5R,6R)-2-amino-3-[(6-chloropyridin-3-yl)
methoxy]-6-fluoro-2-({(1S)-1-[(tricyclo[3.3.1.1$^{3,7}$]de-
cane-1-carbonyl)oxy]ethoxy}carbonyl)bicyclo[3.1.0]
hexane-6-carboxylic acid, (1R,2R,3R,5R,6R)-2-amino-6-fluoro-3-[(4-methylphe-
nyl)methoxy]-2-({(1S)-1-[(tricyclo[3.3.1.1$^{3,7}$]decane-
1-carbonyl)oxy]ethoxy}carbonyl)bicyclo[3.1.0]
hexane-6-carboxylic acid, (1R,2R,3R,5R,6R)-2-amino-6-fluoro-3-(3-methylbu-
toxy)-2-({(1S)-1-[(tricyclo[3.3.1.1$^{3,7}$]decane-1-carbo-
nyl)oxy]ethoxy}carbonyl)bicyclo[3.1.0]hexane-6-car-
boxylic acid, (1R,2R,3R,5R,6R)-2-amino-3-(cyclopentyloxy)-6-
fluoro-2-({(1S)-1-[(tricyclo[3.3.1.1$^{3,7}$]decane-1-carbo-
nyl)oxy]ethoxy}carbonyl)bicyclo[3.1.0]hexane-6-car-
boxylic acid, (1R,2R,3R,5R,6R)-2-amino-6-fluoro-3-[(3-fluorophenyl)
methoxy]-2-({(1R)-1-[({[(1R,2S,5R)-5-methyl-2-(pro-
pan-2-yl)cyclohexyl]oxy}carbonyl)oxy]
ethoxy}carbonyl)bicyclo[3.1.0]hexane-6-carboxylic
acid, (1R,2R,3R,5R,6R)-2-amino-34(6-chloropyridin-2-yl)
methoxyl-6-fluoro-2-({(1R)-1-[({[(1R,2S,5R)-5-
methyl-2-(propan-2-yl)cyclohexyl]oxy}carbonyl)oxy]
ethoxy}carbonyl)bicyclo[3.1.0]hexane-6-carboxylic
acid, (1R,2R,3R,5R,6R)-2-amino-2-({[(2,2-dimethylpro-
panoyl)oxy]methoxy}carbonyl)-6-fluoro-3-[(4-fluoro-
phenyl)methoxy]bicyclo[3.1.0]hexane-6-carboxylic
acid, (1R,2R,3R,5R,6R)-2-amino-2-{[(benzoyloxy)methoxy]
carbonyl}-6-fluoro-3-[(4-fluorophenyl)methoxy]bicy-
clo[3.1.0]hexane-6-carboxylic acid, (1R,2R,3R,5R,6R)-2-amino-2-({[(cyclohexanecarbonyl)
oxy]methoxy}carbonyl)-6-fluoro-3-[(4-fluorophenyl)
methoxy]bicyclo[3.1.0]hexane-6-carboxylic acid, and (1S,2R,3R,5R,6S)-2-amino-3-[(4-fluorophenyl)
methoxy]-2-({(1S)-1-[(tricyclo[3.3.1.1$^{3,7}$]decane-1-
carbonyl)oxy]ethoxy}carbonyl)bicyclo[3.1.0]hexane-
6-carboxylic acid, or a pharmaceutically acceptable salt thereof.

13. The compound or pharmaceutically acceptable salt thereof according to claim 1, wherein the compound or pharmaceutically acceptable salt thereof is any of the following compounds:

(1R,2R,3R,5R,6R)-2-amino-6-fluoro-3-[(4-fluorophenyl)
methoxy]-2-({(1S)-1-[(tricyclo[3.3.1.1$^{3,7}$]decane-1-
carbonyl)oxy]ethoxy}carbonyl)bicyclo[3.1.0]hexane-
6-carboxylic acid, (1R,2R,3R,5R,6R)-2-amino-6-fluoro-3-[(4-fluorophenyl)
methoxy]-2-({[(tricyclo[3.3.1.1$^{3,7}$]decane-1-carbonyl)
oxy]methoxy}carbonyl)bicyclo[3.1.0]hexane-6-car-
boxylic acid, (1R,2R,3R,5R,6R)-2-amino-3-[(3,4-difluorophenyl)
methoxy]-6-fluoro-2-({(1S)-1-[(tricyclo[3.3.1.1$^{3,7}$]de-
cane-1-carbonyl)oxy]ethoxy}carbonyl)bicyclo[3.1.0]
hexane-6-carboxylic acid, (1R,2R,3R,5R,6R)-2-amino-3-[(3,4-difluorophenyl)
methoxy]-6-fluoro-2-({[(tricyclo[3.3.1.1$^{3,7}$]decane-1-
carbonyl)oxy]methoxy}carbonyl)bicyclo[3.1.0]
hexane-6-carboxylic acid, (1R,2R,3R,5R,6R)-2-amino-6-fluoro-2-({(1R)-1-[({[(1R,
2S,5R)-5-methyl-2-(propan-2-yl)cyclohexyl]
oxy}carbonyl)oxy]ethoxy}carbonyl)-3-propoxybicy-
clo[3.1.0]hexane-6-carboxylic acid, (1R,2R,3R,5R,6R)-2-amino-6-fluoro-2-({(1S)-1-[(tricy-
clo[3.3.1.1$^{3,7}$]decane-1-carbonyl)oxy]
ethoxy}carbonyl)-3-{[4-(trifluoromethyl)phenyl]
methoxy}bicyclo[3.1.0]hexane-6-carboxylic acid, (1R,2R,3R,5R,6R)-2-amino-6-fluoro-3-[(3-fluorophenyl)
methoxy]-2-({(1S)-1-[(tricyclo[3.3.1.1$^{3,7}$]decane-1-
carbonyl)oxy]ethoxy}carbonyl)bicyclo[3.1.0]hexane-
6-carboxylic acid, (1R,2R,3R,5R,6R)-2-amino-3-[(6-chloropyridin-2-yl)
methoxy]-6-fluoro-2-({(1S)-1-[(tricyclo[3.3.1.1$^{3,7}$]de-
cane-1-carbonyl)oxy]ethoxy}carbonyl)bicyclo[3.1.0]
hexane-6-carboxylic acid, (1R,2R,3R,5R,6R)-2-amino-6-fluoro-3-[(1R)-1-(4-
fluoro-3-methoxyphenyl)ethoxy]-2-({(1S)-1-[(tricyclo
[3.3.1.1$^{3,7}$]decane-1-carbonyl)oxy]ethoxy}carbonyl)
bicyclo[3.1.0]hexane-6-carboxylic acid, (1R,2R,3R,5R,6R)-2-amino-3-[(5-chloropyridin-2-yl)
methoxy]-6-fluoro-2-({(1S)-1-[(tricyclo[3.3.1.1$^{3,7}$]de-
cane-1-carbonyl)oxy]ethoxy}carbonyl)bicyclo[3.1.0]
hexane-6-carboxylic acid, (1R,2R,3R,5R,6R)-2-amino-3-[(6-chloropyridin-3-yl)
methoxy]-6-fluoro-2-({(1S)-1-[(tricyclo[3.3.1.1$^{3,7}$]de-
cane-1-carbonyl)oxy]ethoxy}carbonyl)bicyclo[3.1.0]
hexane-6-carboxylic acid, (1R,2R,3R,5R,6R)-2-amino-6-fluoro-3-[(4-methylphe-
nyl)methoxy]-2-({(1S)-1-[(tricyclo[3.3.1.1$^{3,7}$]decane-
1-carbonyl)oxy]ethoxy}carbonyl)bicyclo[3.1.0]
hexane-6-carboxylic acid, (1R,2R,3R,5R,6R)-2-amino-6-fluoro-3-(3-methylbu-
toxy)-2-({(1S)-1-[(tricyclo[3.3.1.1$^{3,7}$]decane-1-carbo-
nyl)oxy]ethoxy}carbonyl)bicyclo[3.1.0]hexane-6-car-
boxylic acid, (1R,2R,3R,5R,6R)-2-amino-3-(cyclopentyloxy)-6-
fluoro-2-({(1S)-1-[(tricyclo[3.3.1.1$^{3,7}$]decane-1-carbo-
nyl)oxy]ethoxy}carbonyl)bicyclo[3.1.0]hexane-6-car-
boxylic acid, and (1S,2R,3R,5R,6S)-2-amino-3-[(4-fluorophenyl)
methoxy]-2-({(1S)-1-[(tricyclo[3.3.1.1$^{3,7}$]decane-1-
carbonyl)oxy]ethoxy}carbonyl)bicyclo[3.1.0]hexane-
6-carboxylic acid, or a pharmaceutically acceptable salt thereof.

14. The compound or pharmaceutically acceptable salt thereof according to claim 1, wherein the compound is the following compound:

(1R,2R,3R,5R,6R)-2-amino-6-fluoro-3-[(4-fluorophenyl)
methoxy]-2-({(1S)-1-[(tricyclo[3.3.1.1$^{3,7}$]decane-1-
carbonyl)oxy]ethoxy}carbonyl)bicyclo[3.1.0]hexane-
6-carboxylic acid

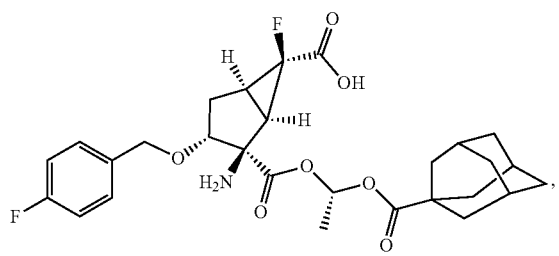 [SMILES: C[C@@H](OC(=O)C12CC3CC(CC(C3)C1)C2)OC(=O)[C@@]1(N)[C@H]2[C@@H](C[C@H]1OCc1ccc(F)cc1)[C@]2(F)C(=O)O]

or a pharmaceutically acceptable salt thereof.

15. The compound or pharmaceutically acceptable salt thereof according to claim 1, wherein the compound or pharmaceutically acceptable salt thereof is the following compound:

(1R,2R,3R,5R,6R)-2-amino-3-[(3,4-difluorophenyl)
methoxy]-6-fluoro-2-({(1S)-1-[(tricyclo[3.3.1.1³,⁷]de-
cane-1-carbonyl)oxy]ethoxy}carbonyl)bicyclo[3.1.0]
hexane-6-carboxylic acid

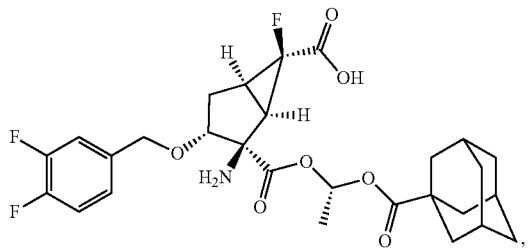 [SMILES: C[C@@H](OC(=O)C12CC3CC(CC(C3)C1)C2)OC(=O)[C@@]1(N)[C@H]2[C@@H](C[C@H]1OCc1ccc(F)c(F)c1)[C@]2(F)C(=O)O]

or a pharmaceutically acceptable salt thereof.

16. The compound or pharmaceutically acceptable salt thereof according to claim 1, wherein the compound or pharmaceutically acceptable salt thereof is the following compound:

(1R,2R,3R,5R,6R)-2-amino-6-fluoro-2-({(1R)-1-[({[(1R,2S,5R)-5-methyl-2-(propan-2-yl)cyclohexyl]oxy}carbonyl)oxy]ethoxy}carbonyl)-3-propoxybicyclo[3.1.0]hexane-6-carboxylic acid

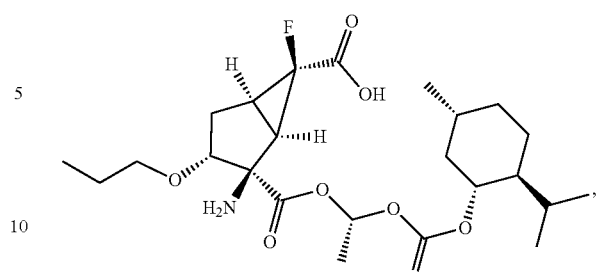

or a pharmaceutically acceptable salt thereof.

17. A pharmaceutical composition comprising the compound or pharmaceutically acceptable salt thereof according to claim 1 and a pharmaceutically acceptable carrier, excipient, or diluent.

18. A pharmaceutical composition comprising the compound or pharmaceutically acceptable salt thereof according to claim 9 and a pharmaceutically acceptable carrier, excipient, or diluent.

\* \* \* \* \*

UNITED STATES PATENT AND TRADEMARK OFFICE
CERTIFICATE OF CORRECTION

PATENT NO. : 10,464,884 B2  
APPLICATION NO. : 15/765903  
DATED : November 5, 2019  
INVENTOR(S) : Norikazu Otake et al.

Page 1 of 1

It is certified that error appears in the above-identified patent and that said Letters Patent is hereby corrected as shown below:

In the Claims

Claim 12, Column 95, Line 22, "(1R,2R,3R,5R,6R)-2-amino-34(6-chloropyridin-2-yl)" should read -- "(1R,2R,3R,5R,6R)-2-amino-3-[(6-chloropyridin-2-yl) --.

Signed and Sealed this  
Fourth Day of February, 2020

Andrei Iancu  
*Director of the United States Patent and Trademark Office*